(12) United States Patent
Kim et al.

(10) Patent No.: US 10,957,862 B2
(45) Date of Patent: Mar. 23, 2021

(54) CONDENSED CYCLIC COMPOUND FOR ORGANIC LIGHT-EMITTING DEVICE, AND ORGANIC LIGHT-EMITTING DEVICE INCLUDING THE COMPOUND

(71) Applicants: SAMSUNG ELECTRONICS CO., LTD., Suwon-si (KR); Samsung SDI Co., Ltd., Yongin-si (KR)

(72) Inventors: Sangmo Kim, Hwaseong-si (KR); Dalho Huh, Suwon-si (KR); Jhunmo Son, Suwon-si (KR); Miyoung Chae, Suwon-si (KR); Eunsuk Kwon, Suwon-si (KR); Hyunjung Kim, Suwon-si (KR); Saeyoun Lee, Suwon-si (KR); Soonok Jeon, Seoul (KR); Yeonsook Chung, Seoul (KR); Yongsik Jung, Yongin-si (KR); Youngmok Son, Hwaseong-si (KR); Namheon Lee, Suwon-si (KR)

(73) Assignees: SAMSUNG ELECTRONICS CO., LTD., Gyeonggi-do (KR); SAMSUNG SDI CO., LTD., Gyeonggi-do (KR)

( * ) Notice: Subject to any disclaimer, the term of this patent is extended or adjusted under 35 U.S.C. 154(b) by 170 days.

(21) Appl. No.: 15/597,771

(22) Filed: May 17, 2017

(65) Prior Publication Data
US 2017/0365796 A1    Dec. 21, 2017

(30) Foreign Application Priority Data
Jun. 16, 2016    (KR) .................. 10-2016-0075313

(51) Int. Cl.
*H01L 29/08*    (2006.01)
*H01L 51/00*    (2006.01)
(Continued)

(52) U.S. Cl.
CPC ........ *H01L 51/0072* (2013.01); *C07D 209/86* (2013.01); *C07D 209/88* (2013.01);
(Continued)

(58) Field of Classification Search
USPC .......................................................... 257/40
See application file for complete search history.

(56) References Cited

U.S. PATENT DOCUMENTS 7,597,967 B2    10/2009    Kondakova et al.
9,530,970 B2    12/2016    Jung et al.
(Continued)

FOREIGN PATENT DOCUMENTS

JP    2007-091719 A    4/2007
JP    2011-044365 A    3/2011
(Continued)

*Primary Examiner* — Caleb E Henry
(74) *Attorney, Agent, or Firm* — Cantor Colburn LLP

(57) ABSTRACT

A condensed cyclic compound represented by Formula 1:

Formula 1

(Continued)

wherein, in Formula 1, groups and variables are the same as described in the specification.

19 Claims, 1 Drawing Sheet

(51) Int. Cl.

| | |
|---|---|
| *C07D 209/86* | (2006.01) |
| *C07D 209/88* | (2006.01) |
| *C07D 401/10* | (2006.01) |
| *C07D 403/10* | (2006.01) |
| *C07D 471/04* | (2006.01) |
| *C07D 487/04* | (2006.01) |
| *C07D 491/048* | (2006.01) |
| *C07D 495/04* | (2006.01) |
| *C09K 11/06* | (2006.01) |
| *H01L 51/50* | (2006.01) |

(52) U.S. Cl.
CPC ......... *C07D 401/10* (2013.01); *C07D 403/10* (2013.01); *C07D 471/04* (2013.01); *C07D 487/04* (2013.01); *C07D 491/048* (2013.01); *C07D 495/04* (2013.01); *C09K 11/06* (2013.01); *H01L 51/0067* (2013.01); *H01L 51/0071* (2013.01); *C09K 2211/1007* (2013.01); *C09K 2211/1029* (2013.01); *C09K 2211/1044* (2013.01); *C09K 2211/1059* (2013.01); *C09K 2211/1088* (2013.01); *C09K 2211/1092* (2013.01); *H01L 51/508* (2013.01); *H01L 51/5016* (2013.01); *H01L 51/5064* (2013.01); *H01L 51/5092* (2013.01); *H01L 51/5096* (2013.01)

(56) References Cited

U.S. PATENT DOCUMENTS

| | | | | |
|---|---|---|---|---|
| 2014/0336379 | A1* | 11/2014 | Adachi | C07D 403/14 |
| | | | | 544/209 |
| 2015/0171342 | A1* | 6/2015 | Jung | C07D 405/14 |
| | | | | 257/40 |
| 2016/0013423 | A1* | 1/2016 | Huh | H01L 51/0072 |
| | | | | 257/40 |
| 2017/0069853 | A1 | 3/2017 | Kim et al. | |

FOREIGN PATENT DOCUMENTS

| | | |
|---|---|---|
| JP | 2012-033892 A | 6/2011 |
| KR | 10-2007-0091291 A | 9/2007 |
| KR | 10-2010-0041690 A | 4/2010 |
| KR | 10-2011-0088427 A | 8/2011 |
| KR | 10-2015-0087045 A | 7/2015 |

\* cited by examiner

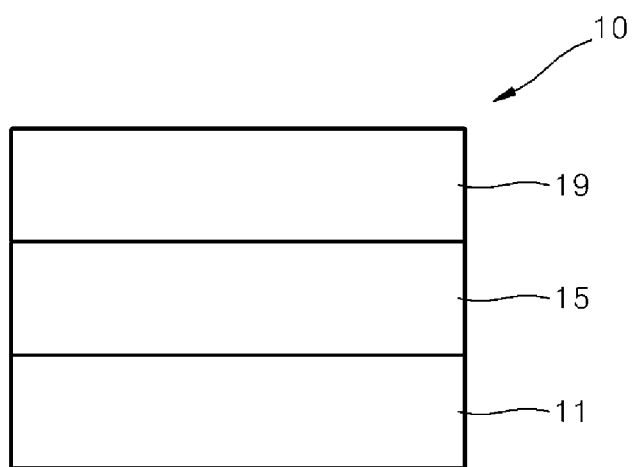

CONDENSED CYCLIC COMPOUND FOR ORGANIC LIGHT-EMITTING DEVICE, AND ORGANIC LIGHT-EMITTING DEVICE INCLUDING THE COMPOUND

CROSS-REFERENCE TO RELATED APPLICATION

This application claims priority to Korean Patent Application No. 10-2016-0075313, filed on Jun. 16, 2016, in the Korean Intellectual Property Office, and all the benefits accruing therefrom under 35 U.S.C. § 119, the content of which is incorporated herein in its entirety by reference.

BACKGROUND

1. Field

The present disclosure relates to a condensed cyclic compound and an organic light-emitting device including the same.

2. Description of the Related Art

Organic light-emitting devices are self-emission devices that have wide viewing angles, high contrast ratios, and short response times. In addition, OLEDs display excellent brightness, driving voltage, and response speed characteristics, and product full-color images.

In an example, an organic light-emitting device includes an anode, a cathode, and an organic layer that is disposed between the anode and the cathode, wherein the organic layer includes an emission layer. A hole transport region may be disposed between the anode and the emission layer, and an electron transport region may be disposed between the emission layer and the cathode. Holes provided from the anode may move toward the emission layer through the hole transport region, and electrons provided from the cathode may move toward the emission layer through the electron transport region. Carriers, such as holes and electrons, recombine in the emission layer to produce excitons. These excitons are changed from an excited state to a ground state, thereby generating light.

Various types of organic light emitting devices are known. However, there still remains a need in OLEDs having low driving voltage, high efficiency, high brightness, and long lifespan.

SUMMARY

Provided are a novel condensed cyclic compound and an organic light-emitting device including the same.

Additional aspects will be set forth in part in the description which follows and, in part, will be apparent from the description, or may be learned by practice of the presented embodiments.

According to an aspect of an embodiment, a condensed cyclic compound is represented by Formula 1:

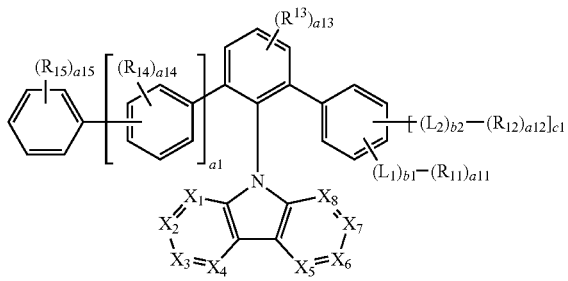

Formula 1

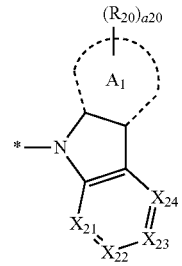

Formula 2-1

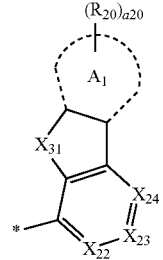

Formula 2-2

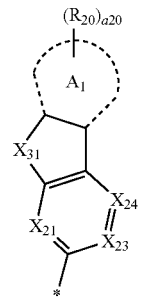

Formula 2-3

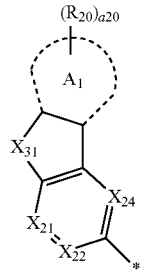

Formula 2-4

Formula 2-5

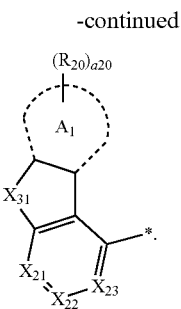

In Formula 1, $X_1$ may be N or $C(R_1)$, $X_2$ may be N or $C(R_2)$, $X_3$ may be N or $C(R_3)$, $X_4$ may be N or $C(R_4)$, $X_5$ may be N or $C(R_5)$, $X_6$ may be N or $C(R_6)$, $X_7$ may be N or $C(R_7)$, and $X_8$ may be N or $C(R_8)$, wherein at least one selected from $X_1$ to $X_8$ is not N, in Formula 1, a1 may be an integer selected from 0 to 3, in Formulae 2-1 to 2-5, $X_{21}$ may be N or $O(R_{21})$, $X_{22}$ may be N or $C(R_{22})$, $X_{23}$ may be N or $C(R_{23})$, and $X_{24}$ may be N or $C(R_{24})$, wherein at least one selected from $X_{21}$ to $X_{24}$ in Formula 2-1 is not N, in Formulae 2-1 to 2-5, ring $A_1$ may be a benzene group, a pyridine group, a pyrimidine group, a pyridazine group, a pyrazine group, a triazine group, a fluorene group, a carbazole group, a dibenzofuran group, a dibenzothiophene group, a dibenzosilol group, an azafluorene group, an azacarbazole group, an azadibenzofuran group, an azadibenzothiophene group, or an azadibenzosilol group, in Formulae 2-2 to 2-5, $X_{31}$ may be O, S, $N(R_{31})$, $C(R_{32})(R_{33})$, or $Si(R_{32})(R_{33})$, in Formulae 2-2 to 2-5, $X_{31}$ may be $N(R_{31})$, or ring $A_1$ may be a carbazole group or an azacarbazole group, in Formula 1, $R_{11}$ may be selected from:

a group represented by one selected from Formulae 2-1 to 2-5;

an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an indazolyl group, a quinolinyl group, an isoquinolinyl group, a benzoquinolinyl group, a phthalazinyl group, a naphthyridinyl group, a quinoxalinyl group, a quinazolinyl group, a cinnolinyl group, a phenanthridinyl group, an acridinyl group, a phenanthrolinyl group, a phenazinyl group, a benzimidazolyl group, an isobenzothiazolyl group, a benzoxazolyl group, an isobenzoxazolyl group, a triazolyl group, a tetrazolyl group, an oxadiazolyl group, a triazinyl group, a thiadiazolyl group, an imidazopyridinyl group, and an imidazopyrimidinyl group; and an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an indazolyl group, a quinolinyl group, an isoquinolinyl group, a benzoquinolinyl group, a phthalazinyl group, a naphthyridinyl group, a quinoxalinyl group, a quinazolinyl group, a cinnolinyl group, a phenanthridinyl group, an acridinyl group, a phenanthrolinyl group, a phenazinyl group, a benzimidazolyl group, an isobenzothiazolyl group, a benzoxazolyl group, an isobenzoxazolyl group, a triazolyl group, a tetrazolyl group, an oxadiazolyl group, a triazinyl group, a thiadiazolyl group, an imidazopyridinyl group, and an imidazopyrimidinyl group, each substituted with at least one selected from deuterium, $—CD_3$, $—CD_2H$, $—CDH_2$, $—F$, $—Cl$, $—Br$, $—I$, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, a biphenyl group, and a terphenyl group, in Formula 1, a11 may be an integer selected from 1 to 3, wherein, when a11 is 2 or more, 2 or more groups $R_{11}$ may be identical to or different from each other, in Formula 1, $R_{12}$ may be hydrogen, deuterium, $—F$, $—Cl$, $—Br$, $—I$, a hydroxyl group, a nitro group, an amino group, an amidino group, a hydrazine group, a hydrazone group, a carboxylic acid group or a salt thereof, a sulfonic acid group or a salt thereof, a phosphoric acid group or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted heterocycloalkyl group, a substituted or unsubstituted $C_3$-$C_{10}$ cycloalkenyl group, a substituted or unsubstituted heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, a substituted or unsubstituted monovalent non-aromatic condensed heteropolycyclic group, $—Si(Q_1)(Q_2)(Q_3)$, $—N(Q_4)(Q_5)$, and $—B(Q_6)(Q_7)$, wherein $R_{12}$ does not a cyano group, in Formula 1, a12 may be an integer selected from 0 to 3, wherein, when a12 is 2 or more, 2 or more groups $R_{12}$ may be identical to or different from each other, in Formulae 1 and 2-1 to 2-5, $R_1$ to $R_5$, $R_{13}$ to $R_{15}$, $R_{20}$ to $R_{24}$, and $R_{31}$ to $R_{33}$ may each independently be selected from:

hydrogen, deuterium, a cyano group, a $C_1$-$C_{20}$ alkyl group, a $C_1$-$C_{20}$ alkoxy group, a phenyl group, a biphenyl group, a terphenyl group, a naphthyl group, a fluorenyl group, a pyridinyl group, a pyrimidinyl group, a pyrazinyl group, a pyridazinyl group, a triazinyl group, a dibenzofuranyl group, a dibenzothiophenyl group, and a dibenzosilolyl group;

a $C_1$-$C_{20}$ alkyl group and a $C_1$-$C_{20}$ alkoxy group, each substituted with at least one of deuterium and a cyano group; and a phenyl group, a biphenyl group, a terphenyl group, a naphthyl group, a fluorenyl group, a pyridinyl group, a pyrimidinyl group, a pyrazinyl group, a pyridazinyl group, a triazinyl group, a dibenzofuranyl group, a dibenzothiophenyl group, and a dibenzosilolyl group, each substituted with at least one selected from deuterium, a cyano group, a $C_1$-$C_{20}$ alkyl group, a $C_1$-$C_{20}$ alkoxy group, a phenyl group, a biphenyl group, a terphenyl group, a naphthyl group, a fluorenyl group, a pyridinyl group, a pyrimidinyl group, a pyrazinyl group, a pyridazinyl group, a triazinyl group, a dibenzofuranyl group, a dibenzothiophenyl group, and a dibenzosilolyl group, wherein $R_{13}$ does not include a cyano group, in Formula 1, a13 may be an integer selected from 0 to 3, wherein, when a13 is 2 or more, 2 or more groups $R_{13}$ may be identical to or different from each other, in Formula 1, a14 may be an integer selected from 0 to 4, wherein, when a14 is 2 or more, 2 or more groups $R_{14}$ may be identical to or different from each other, in Formula 1, a15 may be an integer selected from 0 to 5, wherein, when a15 is 2 or more, 2 or more groups $R_{15}$ may be identical to or different from each other, in Formulae 2-1 to 2-5, a20 may be an integer selected from 0 to 8, wherein, when a20 is 2 or more, 2 or more groups $R_{20}$ may be identical to or different from each other, in Formula 1, $L_1$ and $L_2$ may each independently be selected from a substituted or unsubstituted $C_3$-$C_{10}$ cycloalkylene group, a substituted or unsubstituted $C_1$-$C_{10}$ heterocycloalkylene group, a substituted or unsubstituted $C_3$-$C_{10}$ cycloalkenylene group, a substituted or unsubstituted $C_1$-$C_{10}$ heterocycloalkenylene group, a substituted or unsubstituted $C_6$-$C_{60}$ arylene group, a substituted or unsubstituted $C_1$-$C_{60}$ heteroarylene group, a substituted or unsubstituted divalent non-aromatic condensed polycyclic group, and a substituted or unsubstituted divalent non-aromatic condensed heteropolycyclic group, wherein $L_2$ does not include a cyano group, in Formula 1, b1 and b2 may each independently be an integer selected from 0 to 5, wherein, when b1 is 2 or more, 2 or more groups $L_1$ may be identical to or different from each other, and when b2 is 2 or more, 2 or more groups $L_2$ may be identical to or different from each other, in Formula 1, c1 may be an integer selected from 0 to 4, the number of carbazole ring(s) in the condensed cyclic compound represented by Formula 1 may be 0, 1, or 2, the condensed cyclic compound represented by Formula 1 may have an asymmetrical structure, in Formulae 2-1 to 2-5, * indicates a binding site to a neighboring atom, at least one substituent selected from substituent(s) of the substituted $C_3$-$C_{10}$ cycloalkylene group, the substituted $C_1$-$C_{10}$ heterocycloalkylene group, the substituted $C_3$-$C_{10}$ cycloalkenylene group, the substituted $C_1$-$C_{10}$ heterocycloalkenylene group, the substituted $C_6$-$C_{10}$ arylene group, the substituted $C_1$-$C_{60}$ heteroarylene group, the substituted divalent non-aromatic condensed polycyclic group, the substituted divalent non-aromatic condensed heteropolycyclic group, the substituted $C_1$-$C_{60}$ alkyl group, the substituted $C_2$-$C_{60}$ alkenyl group, the substituted $C_2$-$C_{60}$ alkynyl group, the substituted $C_3$-$C_{10}$ cycloalkyl group, the substituted $C_1$-$C_{10}$ heterocycloalkyl group, the substituted $C_3$-$C_{10}$ cycloalkenyl group, the substituted $C_1$-$C_{10}$ heterocycloalkenyl group, the substituted $C_6$-$C_{60}$ aryl group, the substituted $C_6$-$C_{60}$ aryloxy group, the substituted $C_6$-$C_{60}$ arylthio group, the substituted $C_1$-$C_{60}$ heteroaryl group, the substituted monovalent non-aromatic condensed polycyclic group, and the substituted monovalent non-aromatic condensed heteropolycyclic group may be selected from:

deuterium, —F, —Cl, —Br, —I, —CD$_3$, —CD$_2$H, —CDH$_2$, —CF$_3$, —CF$_2$H, —CFH$_2$, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, and a $C_1$-$C_{60}$ alkoxy group;

a $C_1$-$C_{60}$ alkyl group, a $C_2$-$C_{60}$ alkenyl group, a $C_2$-$C_{60}$ alkynyl group, and a $C_1$-$C_{60}$ alkoxy group, each substituted with at least one selected from deuterium, —F, —Cl, —Br, —I, —CD$_3$, —CD$_2$H, —CDH$_2$, —CF$_3$, —CF$_2$H, —CFH$_2$, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —Si($Q_{11}$)($Q_{12}$)($Q_{13}$), —N($C)_{14}$)($Q_{15}$), and —B($Q_{16}$)($Q_{17}$);

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group;

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group, each substituted with at least one selected from deuterium, —F, —Cl, —Br, —I, —CD$_3$, —CD$_2$H, —CDH$_2$, —CF$_3$, —CF$_2$H, —CFH$_2$, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —Si($Q_{21}$)($Q_{22}$)($Q_{23}$), —N($Q_{24}$)($Q_{25}$), and —B($Q_{26}$)($Q_{27}$); and —Si($Q_{31}$)($Q_{32}$)($Q_{33}$), —N($Q_{34}$)($Q_{35}$), and —B($Q_{36}$)($Q_{37}$), and $Q_1$ to $Q_7$, $Q_{11}$ to $Q_{17}$, $Q_{21}$ to $Q_{27}$, and $Q_{31}$ to $Q_{37}$ may each independently be selected from hydrogen, deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted heterocycloalkyl group, a substituted or unsubstituted $C_3$-$C_{10}$ cycloalkenyl group, a substituted or unsubstituted heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, and a substituted or unsubstituted monovalent non-aromatic condensed heteropolycyclic group.

According to an aspect of another embodiment, an organic light-emitting device includes:

a first electrode;

a second electrode; and an organic layer that is disposed between the first electrode and the second electrode, wherein the organic layer includes an emission layer, and wherein the organic layer includes at least one condensed cyclic compound represented by Formula 1.

BRIEF DESCRIPTION OF THE DRAWING

These and/or other aspects will become apparent and more readily appreciated from the following description of the embodiments, taken in conjunction with FIG. 1 which is a schematic cross-section of an organic light-emitting device according to an embodiment

DETAILED DESCRIPTION

Reference will now be made in detail to embodiments, examples of which are illustrated in the accompanying drawings, wherein like reference numerals refer to like elements throughout. In this regard, the present embodiments may have different forms and should not be construed as being limited to the descriptions set forth herein. Accordingly, the embodiments are merely described below, by referring to the figures, to explain aspects of the present inventive concept. As used herein, the term "and/or" includes any and all combinations of one or more of the associated listed items. Expressions such as "at least one of," when preceding a list of elements, modify the entire list of elements and do not modify the individual elements of the list.

It will be understood that when an element is referred to as being "on" another element, it can be directly in contact with the other element or intervening elements may be present therebetween. In contrast, when an element is referred to as being "directly on" another element, there are no intervening elements present.

It will be understood that, although the terms first, second, third etc. may be used herein to describe various elements, components, regions, layers, and/or sections, these elements, components, regions, layers, and/or sections should not be limited by these terms. These terms are only used to distinguish one element, component, region, layer, or section from another element, component, region, layer, or section. Thus, a first element, component, region, layer, or section discussed below could be termed a second element, component, region, layer, or section without departing from the teachings of the present embodiments.

The terminology used herein is for the purpose of describing particular embodiments only and is not intended to be limiting. As used herein, the singular forms "a," "an," and "the" are intended to include the plural forms as well, unless the context clearly indicates otherwise.

The term "or" means "and/or." It will be further understood that the terms "comprises" and/or "comprising," or "includes" and/or "including" when used in this specification, specify the presence of stated features, regions, integers, steps, operations, elements, and/or components, but do not preclude the presence or addition of one or more other features, regions, integers, steps, operations, elements, components, and/or groups thereof.

Unless otherwise defined, all terms (including technical and scientific terms) used herein have the same meaning as commonly understood by one of ordinary skill in the art to which this general inventive concept belongs. It will be further understood that terms, such as those defined in commonly used dictionaries, should be interpreted as having a meaning that is consistent with their meaning in the context of the relevant art and the present disclosure, and will not be interpreted in an idealized or overly formal sense unless expressly so defined herein.

Exemplary embodiments are described herein with reference to cross section illustrations that are schematic illustrations of idealized embodiments. As such, variations from the shapes of the illustrations as a result, for example, of manufacturing techniques and/or tolerances, are to be expected. Thus, embodiments described herein should not be construed as limited to the particular shapes of regions as illustrated herein but are to include deviations in shapes that result, for example, from manufacturing. For example, a region illustrated or described as flat may, typically, have rough and/or nonlinear features. Moreover, sharp angles that are illustrated may be rounded. Thus, the regions illustrated in the figures are schematic in nature and their shapes are not intended to illustrate the precise shape of a region and are not intended to limit the scope of the present claims.

"About" or "approximately" as used herein is inclusive of the stated value and means within an acceptable range of deviation for the particular value as determined by one of ordinary skill in the art, considering the measurement in question and the error associated with measurement of the particular quantity (i.e., the limitations of the measurement system). For example, "about" can mean within one or more standard deviations, or within ±30%, 20%, 10%, 5% of the stated value.

According to an aspect of the present disclosure, a condensed cyclic compound is represented is represented by Formula 1:

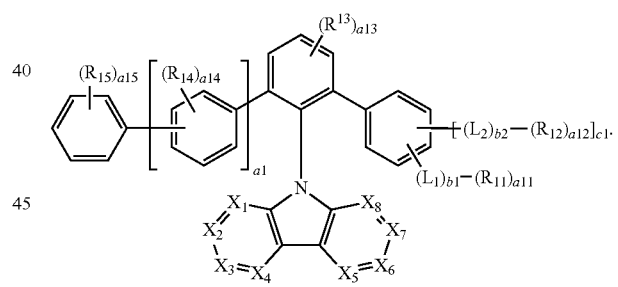

Formula 1

In Formula 1, $R_{11}$ may be selected from groups represented by Formulae 2-1 to 2-5, or electron-transporting groups. $R_{11}$ the same as described elsewhere herein in the present specification:

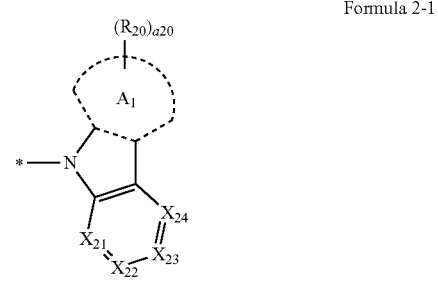

Formula 2-1

-continued

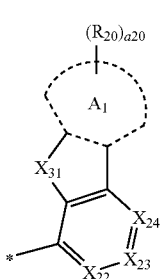

Formula 2-2

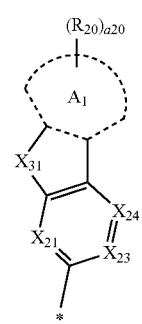

Formula 2-3

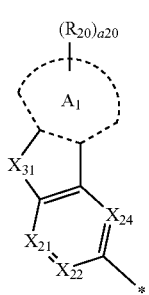

Formula 2-4

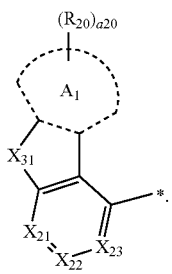

Formula 2-5

In Formula 1, $X_1$ may be N or $C(R_1)$, $X_2$ may be N or $C(R_2)$, $X_3$ may be N or $C(R_3)$, $X_4$ may be N or $C(R_4)$, $X_5$ may be N or $C(R_5)$, $X_6$ may be N or $C(R_6)$, $X_7$ may be N or $C(R_7)$, and $X_8$ may be N or $C(R_8)$. Here, at least one selected from $X_1$ to $X_8$ may not be N. That is, $X_1$ to $X_8$ in Formula 1 may not all be N at the same time.

In an embodiment, 0, 1, or 2 selected among $X_1$ to $X_8$ in Formula 1 may be N.

In various embodiments, in Formula 1, $X_1$ may be $C(R_1)$, $X_2$ may be $C(R_2)$, $X_3$ may be $C(R_3)$, $X_4$ may be $C(R_4)$, $X_5$ may be $C(R_5)$, $X_6$ may be $C(R_6)$, $X_7$ may be $C(R_7)$, and $X_8$ may be $C(R_8)$.

In various embodiments, in Formula 1, $X_1$ may be $C(R_1)$, $X_2$ may be $C(R_2)$, $X_3$ may be N, $X_4$ may be $C(R_4)$, $X_5$ may be $C(R_5)$, $X_5$ may be $C(R_6)$, $X_7$ may be $C(R_7)$, and $X_5$ may be $C(R_8)$.

In various embodiments, in Formula 1, $X_1$ may be $C(R_1)$, $X_2$ may be $C(R_2)$, $X_3$ may be $C(R_3)$, $X_4$ may be $C(R_4)$, $X_5$ may be $C(R_5)$, $X_5$ may be N, $X_7$ may be $C(R_7)$, and $X_8$ may be $C(R_8)$.

In Formula 1, a1 may be an integer selected from 0 to 3. When a1 in Formula 1 is 2 or more, 2 or more phenylene group(s) shown in "[ ]" in Formula 1 may be identical to or different from each other.

For example, a1 in Formula 1 may be 0 or 1, but embodiments are not limited thereto.

In Formulae 2-1 to 2-5, $X_{21}$ may be N or $C(R_{21})$, $X_{22}$ may be N or $C(R_{22})$, $X_{23}$ may be N or $C(R_{23})$, and $X_{24}$ may be N or $C(R_{24})$. Here, at least one selected from $X_{21}$ to $X_{24}$ in Formula 2-1 may not be N. That is, $X_{21}$ to $X_{24}$ in Formula 2-1 may not all be N at the same time.

In an embodiment, 0, 1, or 2 selected among $X_{21}$ to $X_{24}$ in Formulae 2-1 to 2-5 may be N.

In Formulae 2-1 to 2-5, ring $A_1$ may be a benzene group, a pyridine group, a pyrimidine group, a pyridazine group, a pyrazine group, a triazine group, a fluorene group, a carbazole group, a dibenzofuran group, a dibenzothiophene group, a dibenzosilol group, an azafluorene group, an azacarbazole group, an azadibenzofuran group, an azadibenzothiophene group, or an azadibenzosilol group. An "azafluorene group" used herein may refer to a group prepared by substituting 'a nitrogen atom' for at least one of a plurality of "carbon atoms" consisting 2 benzo-rings of "a fluorene group". The terms "an azacarbazole group, an azadibenzofuran group, an azadibenzothiophene group, and an azadibenzosilol group" as used here may each independently be understood likewise.

For example, in Formulae 2-1 to 2-5, ring $A_1$ may be a benzene group, a pyridine group, a carbazole group, a dibenzofuran group, a dibenzothiophene group, or an azacarbazole group, but embodiments are not limited thereto.

In Formulae 2-2 to 2-5, $X_{31}$ may be O, S, $N(R_{31})$, $C(R_{32})(R_{33})$, or $Si(R_{32})(R_{33})$. In Formulae 2-2 to 2-5, $R_{31}$ to $R_{33}$ may each independently be the same as described elsewhere herein in connection with those provided in the present specification.

In Formulae 2-2 to 2-5, $X_{31}$ may be $N(R_{31})$, and ring $A_1$ may be a carbazole group or an azacarbazole group.

In Formula 1, $R_{11}$ may be selected from:
a group represented by one selected from Formulae 2-1 to 2-5;
an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an indazolyl group, a quinolinyl group, an isoquinolinyl group, a benzoquinolinyl group, a phthalazinyl group, a naphthyridinyl group, a quinoxalinyl group, a quinazolinyl group, a cinnolinyl group, a phenanthridinyl group, an acridinyl group, a phenanthrolinyl group, a phenazinyl group, a benzimidazolyl group, an isobenzothiazolyl group, a benzoxazolyl group, an isobenzoxazolyl group, a triazolyl group, a tetrazolyl group, an oxadiazolyl group, a triazinyl group, a thiadiazolyl group, an imidazopyridinyl group, and an imidazopyrimidinyl group; and
an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an indazolyl group, a quinolinyl group, an isoquinolinyl group, a benzoquinolinyl group, a phthalazinyl group, a naphthyridinyl group, a quinoxalinyl group, a quinazolinyl group, a cinnolinyl group, a phenanthridinyl group, an acridinyl group, a phenanthrolinyl group, a phenazinyl group, a benzimidazolyl group, an isobenzothiazolyl group, a benzoxazolyl group, an isobenzoxazolyl group, a triazolyl group, a tetrazolyl group, an oxadiazolyl group, a triazinyl group, a thiadiazolyl group, an imidazopyridinyl group, and an imidazopyrimidinyl group, each substituted with at least one selected from deuterium, —$CD_3$, —$CD_2H$, —$CDH_2$, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, a biphenyl group, and a terphenyl group.

In an embodiment, $R_{11}$ in Formula 1 may be represented by one selected from groups represented by Formulae 2-1A to 2-5A, 2-1B to 2-5B, 2-1C to 2-5C, 2-1D to 2-5D, 2-1E to 2-5E, 2-1F to 2-5F, and 2-1G to 2-5G:

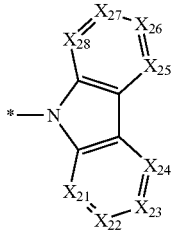

Formula 2-1A

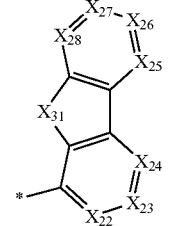

Formula 2-2A

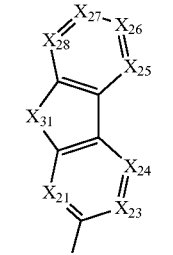

Formula 2-3A

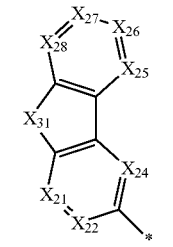

Formula 2-4A

-continued

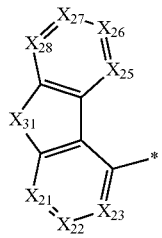

Formula 2-5A

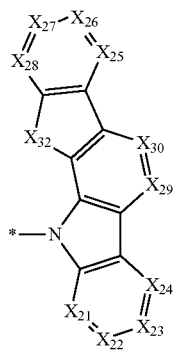

Formula 2-1B

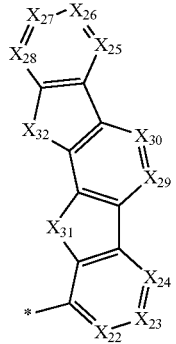

Formula 2-2B

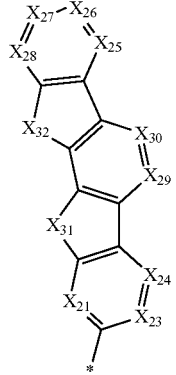

Formula 2-3B

Formula 2-4B
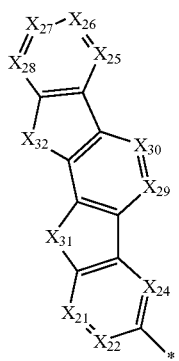
Formula 2-5B
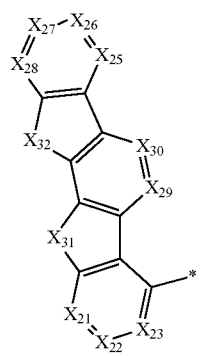
Formula 2-1C
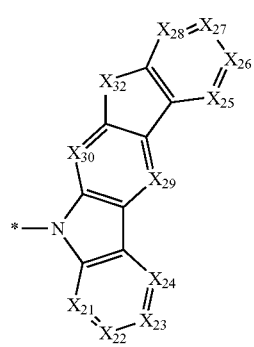
Formula 2-2C
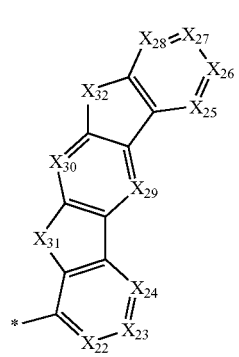
Formula 2-3C
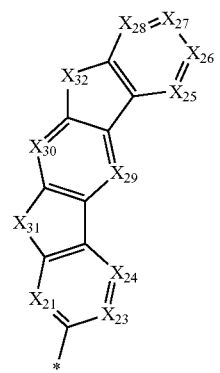
Formula 2-4C
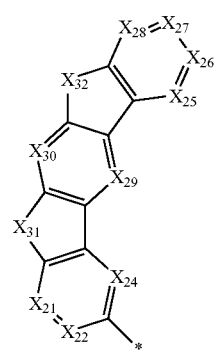
Formula 2-5C
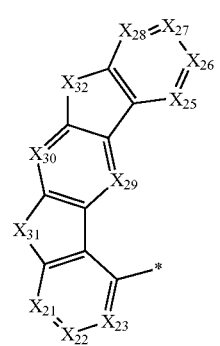
Formula 2-1D
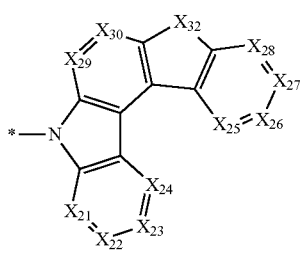
Formula 2-2D
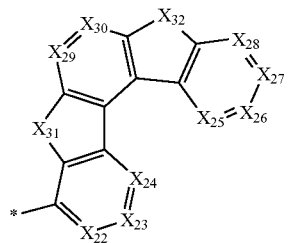

-continued
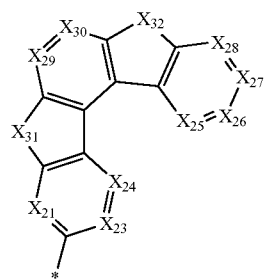
Formula 2-3D
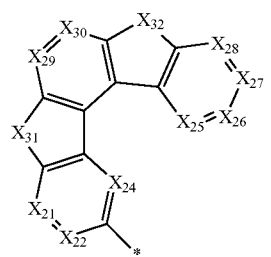
Formula 2-4D
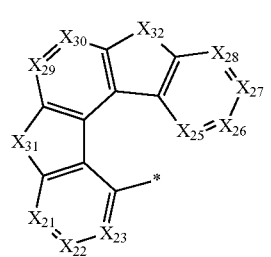
Formula 2-5D
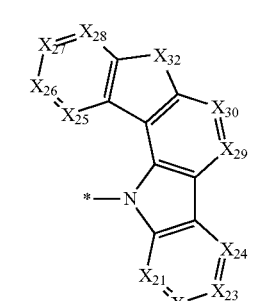
Formula 2-1E
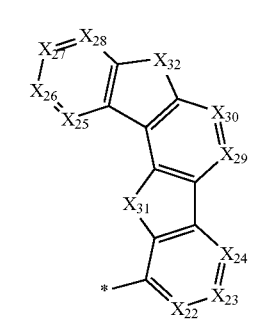
Formula 2-2E
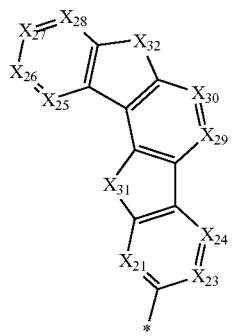
Formula 2-3E
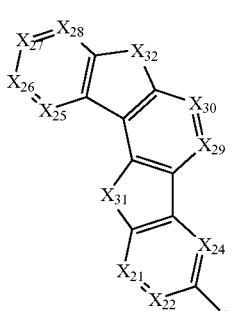
Formula 2-4E
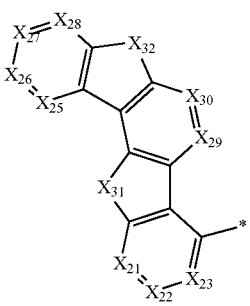
Formula 2-5E
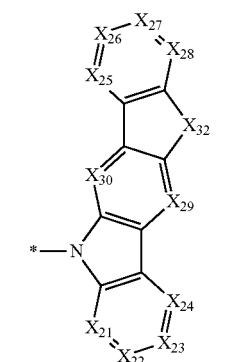
Formula 2-1F -continued
Formula 2-2F
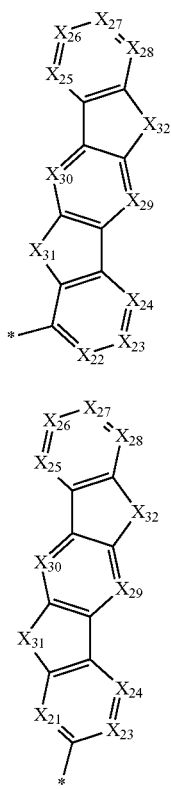
Formula 2-3F
Formula 2-4F
Formula 2-5F
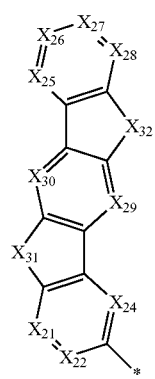
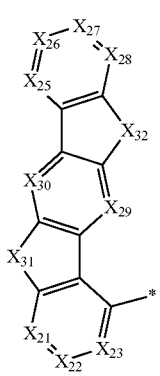
Formula 2-1G
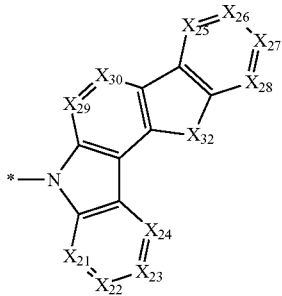
Formula 2-2G
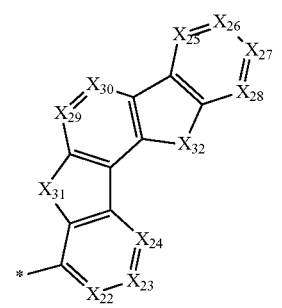
Formula 2-3G
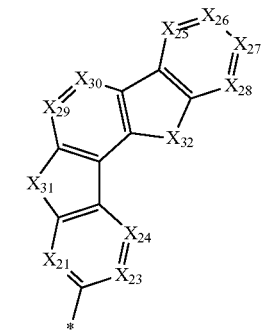
Formula 2-4G
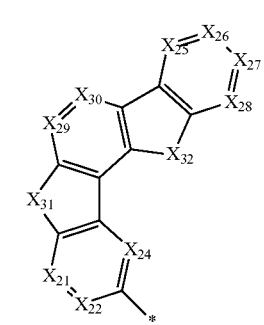
Formula 2-5G
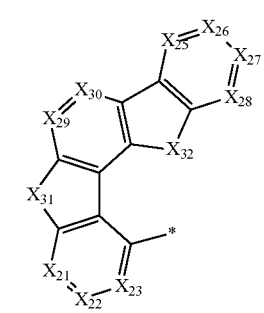
In Formulae 2-1A to 2-5A, 2-1B to 2-5B, 2-1C to 2-5C, 2-1D to 2-5D, 2-1E to 2-5E, 2-1F to 2-5F, and 2-1G to 2-5G, $X_{21}$ to $X_{24}$ and $X_{31}$ may each independently be the same as described elsewhere herein in connection with those provided in the present specification, $X_{25}$ may be N or $C(R_{25})$, $X_{26}$ may be N or $C(R_{26})$, $X_{27}$ may be N or $C(R_{27})$, $X_{28}$ may be N or $C(R_{28})$, $X_{29}$ may be N or $C(R_{29})$, and $X_{30}$ may be N or $C(R_{30})$. Here, at least one selected from $X_{25}$ to $X_{30}$ may not be N. That is, $X_{25}$ to $X_{30}$ may not be N at the same time.

$R_{25}$ to $R_{30}$ may each independently be the same as described herein in connection with $R_{20}$ provided in the present specification, $X_{32}$ may be O, S, $N(R_{34})$, $C(R_{35})(R_{36})$, or $Si(R_{35})(R_{36})$, $R_{34}$ may be the same as described herein in connection with $R_{31}$ provided in the present specification, $R_{35}$ and $R_{36}$ may each independently be the same as described herein in connection with $R_{32}$ provided in the present specification, in Formulae 2-2A to 2-5A, 2-2B to 2-5B, 2-2C to 2-5C, 2-2D to 2-5D, 2-2E to 2-5E, 2-2F to 2-5F, and 2-2G to 2-5G, i) when $X_{31}$ is O, S, $C(R_{32})(R_{33})$, or $Si(R_{32})(R_{33})$, $X_{32}$ may be $N(R_{34})$, and ii) when $X_{32}$ is O, S, $C(R_{35})(R_{36})$, or $Si(R_{35})(R_{36})$, $X_{31}$ may be $N(R_{31})$, and

* indicates a binding site to a neighboring atom.

For example, 0, 1, or 2 selected among $X_{21}$ to $X_{28}$ in Formulae 2-1A to 2-5A, 2-1B to 2-5B, 2-1C to 2-5C, 2-1D to 2-5D, 2-1E to 2-5E, 2-1F to 2-5F, and 2-1G to 2-5G may be N.

In various embodiments, in Formulae 2-1A to 2-5A, 2-1B to 2-5B, 2-1C to 2-5C, 2-1D to 2-5D, 2-1E to 2-5E, 2-1F to 2-5F, and 2-1G to 2-5G, $X_{21}$ may be $C(R_{21})$, $X_{22}$ may be $C(R_{22})$, $X_{23}$ may be $C(R_{23})$, $X_{24}$ may be $C(R_{24})$, $X_{25}$ may be $C(R_{25})$, $X_{26}$ may be $C(R_{26})$, $X_{27}$ may be $C(R_{27})$, $X_{28}$ may be $C(R_{28})$, $X_{29}$ may be $C(R_{29})$, and $X_{30}$ may be $C(R_{30})$.

In various embodiments, in Formulae 2-1A to 2-5A, 2-1B to 2-5B, 2-1C to 2-5C, 2-1D to 2-5D, 2-1E to 2-5E, 2-1F to 2-5F, and 2-1G to 2-5G, $X_{21}$ may be $C(R_{21})$, $X_{22}$ may be $C(R_{22})$, $X_{23}$ may be N, $X_{24}$ may be $C(R_{24})$, $X_{25}$ may be $C(R_{25})$, $X_{26}$ may be $C(R_{26})$, $X_{27}$ may be $C(R_{27})$, $X_{28}$ may be $C(R_{28})$, $X_{29}$ may be $C(R_{29})$, and $X_{30}$ may be $C(R_{30})$.

In various embodiments, in Formulae 2-1A to 2-5A, 2-1B to 2-5B, 2-1C to 2-5C, 2-1D to 2-5D, 2-1E to 2-5E, 2-1F to 2-5F, and 2-1G to 2-5G, $X_{21}$ may be $C(R_{21})$, $X_{22}$ may be $C(R_{22})$, $X_{23}$ may be N, $X_{24}$ may be $C(R_{24})$, $X_{25}$ may be $C(R_{25})$, $X_{26}$ may be N, $X_{27}$ may be $C(R_{27})$, $X_{28}$ may be $C(R_{28})$, $X_{29}$ may be $C(R_{29})$, and $X_{30}$ may be $C(R_{30})$.

In various embodiments, $R_{11}$ in Formula 1 may be selected from:

an imidazolyl group, a pyridinyl group, a pyrazinyl group, a pyrimidinyl group, a pyridazinyl group, a quinolinyl group, an isoquinolinyl group, a quinoxalinyl group, a quinazolinyl group, a phenanthrolinyl group, a benzimidazolyl group, a triazinyl group, an imidazopyridinyl group, and an imidazopyrimidinyl group; and an imidazolyl group, a pyridinyl group, a pyrazinyl group, a pyrimidinyl group, a pyridazinyl group, a quinolinyl group, an isoquinolinyl group, a quinoxalinyl group, a quinazolinyl group, a phenanthrolinyl group, a benzimidazolyl group, a triazinyl group, an imidazopyridinyl group, and an imidazopyrimidinyl group, each substituted with at least one selected from deuterium, —$CD_3$, —$CD_2H$, —$CDH_2$, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a biphenyl group, a terphenyl group, an imidazolyl group, a pyridinyl group, a pyrazinyl group, a pyrimidinyl group, a pyridazinyl group, a quinolinyl group, an isoquinolinyl group, a quinoxalinyl group, a quinazolinyl group, a phenanthrolinyl group, a benzimidazolyl group, a triazinyl group, an imidazopyridinyl group, and an imidazopyrimidinyl group.

For example, $R_{11}$ in Formula 1 may be selected from groups represented by Formulae 5-1 to 5-55, but embodiments are not limited thereto:

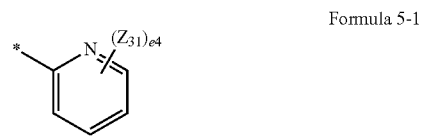

Formula 5-1

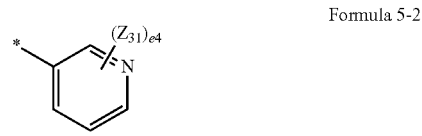

Formula 5-2

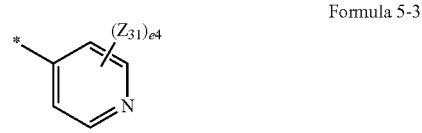

Formula 5-3

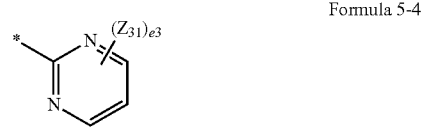

Formula 5-4

Formula 5-5

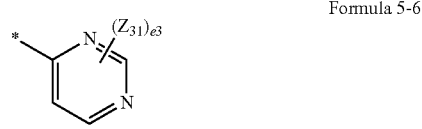

Formula 5-6

Formula 5-7

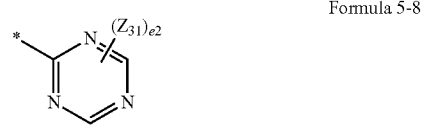

Formula 5-8

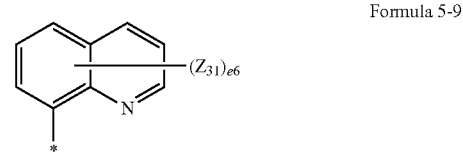

Formula 5-9

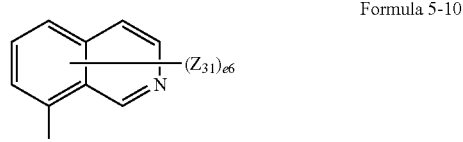

Formula 5-10

Formula 5-11
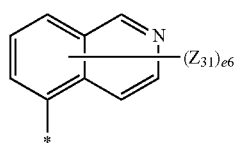
Formula 5-12
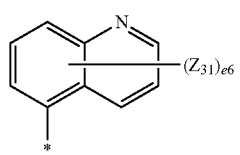
Formula 5-13
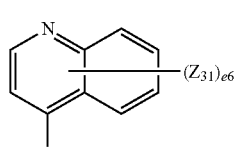
Formula 5-14
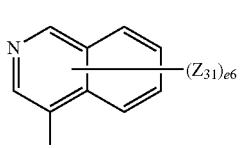
Formula 5-15
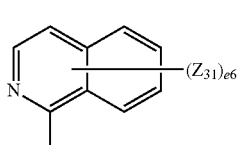
Formula 5-16
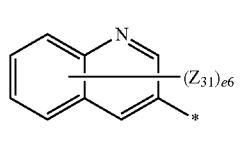
Formula 5-17
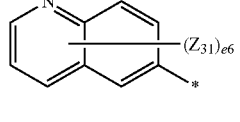
Formula 5-18
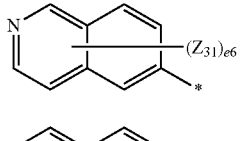
Formula 5-19
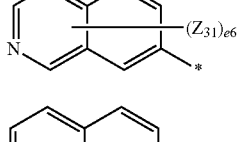
Formula 5-20
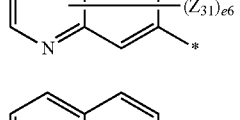
Formula 5-21
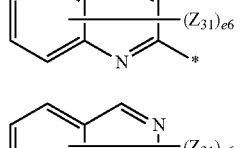
Formula 5-22
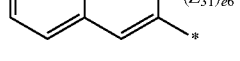
Formula 5-23
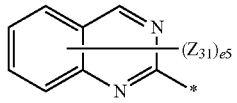
Formula 5-24
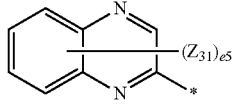
Formula 5-25
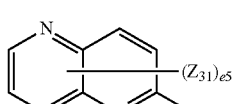
Formula 5-26
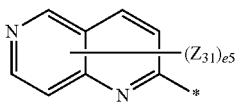
Formula 5-27
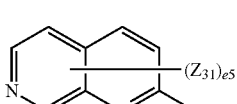
Formula 5-28
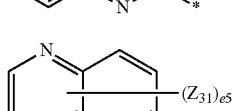
Formula 5-29
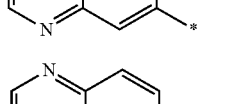
Formula 5-30
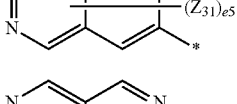
Formula 5-31
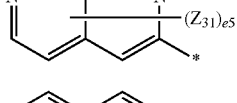
Formula 5-32
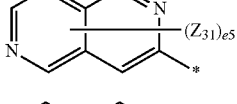
Formula 5-33
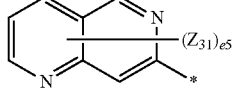
Formula 5-34
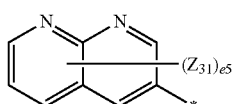
Formula 5-35
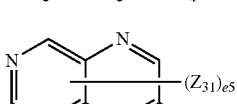
Formula 5-36
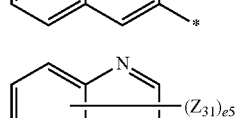

-continued

Formula 5-37
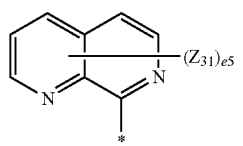

Formula 5-38
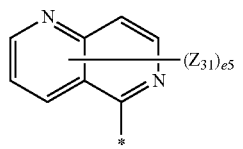

Formula 5-39
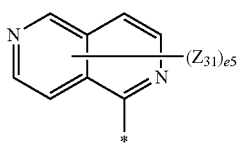

Formula 5-40
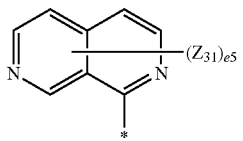

Formula 5-41
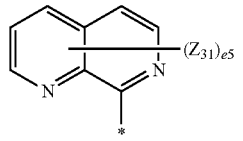

Formula 5-42
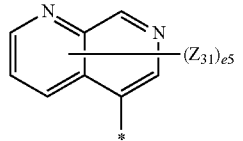

Formula 5-43
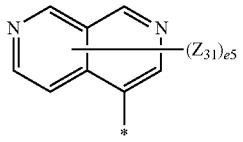

Formula 5-44
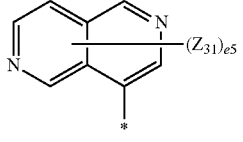

Formula 5-45
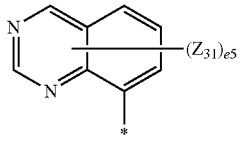

Formula 5-46
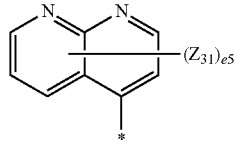

-continued

Formula 5-47
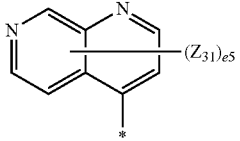

Formula 5-48
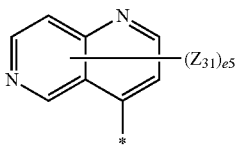

Formula 5-49
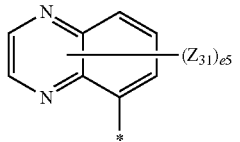

Formula 5-50
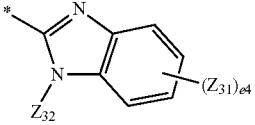

Formula 5-51
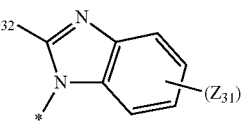

Formula 5-52
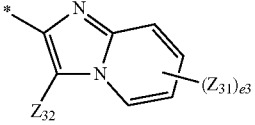

Formula 5-53
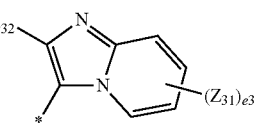

Formula 5-54
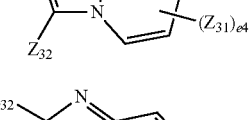

Formula 5-55
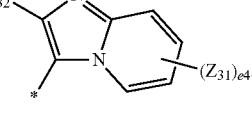

In Formulae 5-1 to 5-55, $Z_{31}$ to $Z_{33}$ may each independently be selected from hydrogen, deuterium, —$CD_3$, —$CD_2H$, —$CDH_2$, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a biphenyl group, and a terphenyl group, e2 may be an integer selected from 0 to 2, e3 may be an integer selected from 0 to 3, e4 may be an integer selected from 0 to 4, and

* indicates a binding site to a neighboring atom.

In Formula 1, a11 indicates the number of groups $R_{11}$, and may be an integer selected from 1 to 3, wherein, when a11 is 2 or more, 2 or more groups $R_{11}$ may be identical to or different from each other. That is, the condensed cyclic compound represented by Formula 1 must include at least one "$R_{11}$".

In an embodiment, a11 in Formula 1 may be 1 or 2, and for example, may be 1.

In Formula 1, $R_{12}$ may be selected from hydrogen, deuterium, —F, —Cl, —Br, —I, a hydroxyl group, a nitro group, an amino group, an amidino group, a hydrazine group, a hydrazone group, a carboxylic acid group or a salt thereof, a sulfonic acid group or a salt thereof, a phosphoric acid group or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted heterocycloalkyl group, a substituted or unsubstituted $C_3$-$C_{10}$ cycloalkenyl group, a substituted or unsubstituted heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, a substituted or unsubstituted monovalent non-aromatic condensed heteropolycyclic group, —Si($Q_1$)($Q_2$)($Q_3$), —N($Q_4$)($Q_5$), and —B($Q_6$)($Q_7$), wherein $R_{12}$ does not include a cyano group.

In Formula 1, a12 indicates the number of groups $R_{12}$, and may be an integer selected from 0 to 3, wherein, when a12 is 2 or more, 2 or more groups $R_{12}$ may be identical to or different from each other. For example, a12 may be 0, 1, or 2, and for example, may be 0 or 1. However, embodiments are not limited thereto.

In Formulae 1 and 2-1 to 2-5, $R_1$ to $R_8$, $R_{13}$ to $R_{15}$, $R_{20}$ to $R_{24}$, and $R_{31}$ to $R_{33}$ may each independently be selected from:

hydrogen, deuterium, a cyano group, a $C_1$-$C_{20}$ alkyl group, a $C_1$-$C_{20}$ alkoxy group, a phenyl group, a biphenyl group, a terphenyl group, a naphthyl group, a fluorenyl group, a pyridinyl group, a pyrimidinyl group, a pyrazinyl group, a pyridazinyl group, a triazinyl group, a dibenzofuranyl group, a dibenzothiophenyl group, and a dibenzosilolyl group;

a $C_1$-$C_{20}$ alkyl group and a $C_1$-$C_{20}$ alkoxy group, each substituted with at least one of deuterium and a cyano group; and a phenyl group, a biphenyl group, a terphenyl group, a naphthyl group, a fluorenyl group, a pyridinyl group, a pyrimidinyl group, a pyrazinyl group, a pyridazinyl group, a triazinyl group, a dibenzofuranyl group, a dibenzothiophenyl group, and a dibenzosilolyl group, each substituted with at least one selected from deuterium, a cyano group, a $C_1$-$C_{20}$ alkyl group, a $C_1$-$C_{20}$ alkoxy group, a phenyl group, a biphenyl group, a terphenyl group, a naphthyl group, a fluorenyl group, a pyridinyl group, a pyrimidinyl group, a pyrazinyl group, a pyridazinyl group, a triazinyl group, a dibenzofuranyl group, a dibenzothiophenyl group, and a dibenzosilolyl group, wherein $R_{13}$ does not include a cyano group.

In Formula 1, a13 indicates the number of groups $R_{13}$, and may be an integer selected from 0 to 3, wherein, when a13 is 2 or more, 2 or more groups $R_{13}$ may be identical to or different from each other. In Formula 1, a14 indicates the number of groups $R_{14}$, and may be an integer selected from 0 to 4, wherein, when a14 is 2 or more, 2 or more groups $R_{14}$ may be identical to or different from each other. In Formula 1, a15 indicates the number of groups $R_{15}$, and may be an integer selected from 0 to 5, wherein, when a15 is 2 or more, 2 or more groups $R_{15}$ may be identical to or different from each other. In Formulae 2-1 to 2-5, a20 indicates the number of groups $R_{20}$, and may be an integer selected from 0 to 8, wherein, when a20 is 2 or more, 2 or more groups $R_{20}$ may be identical to or different form each other.

For example, a13 to a15 in Formula 1 may each independently be 0 or 1, but embodiments are not limited thereto.

In an embodiment, in Formulae 1 and 2-1 to 2-5, $R_1$ to $R_8$, $R_{12}$ to $R_{15}$, $R_{20}$ to $R_{24}$, and $R_{31}$ to $R_{33}$ may each independently be selected from:

hydrogen, deuterium, a cyano group, a $C_1$-$C_{10}$ alkyl group, a $C_1$-$C_{10}$ alkoxy group, a phenyl group, a biphenyl group, a terphenyl group, and a pyridinyl group;

a $C_1$-$C_{10}$ alkyl group and a $C_1$-$C_{10}$ alkoxy group, each substituted with at least one of deuterium and a cyano group; and a phenyl group, a biphenyl group, a terphenyl group, and a pyridinyl group, each substituted with at least one selected from deuterium, a cyano group, a $C_1$-$C_{10}$ alkyl group, a $C_1$-$C_{10}$ alkoxy group, a phenyl group, a biphenyl group, a terphenyl group, and a pyridinyl group, but embodiments are not limited thereto.

In various embodiments, in Formula 1, at least one of $X_3$ and $X_6$ may be C(CN) or N.

In various embodiments, in Formulae 2-1A to 2-5A, 2-1B to 2-5B, 2-1C to 2-5C, 2-1D to 2-5D, 2-1E to 2-5E, 2-1F to 2-5F, and 2-1G to 2-5G, at least one of $X_{23}$ and $X_{26}$ may be C(CN) or N, but embodiments are not limited thereto.

In Formula 1, $L_1$ and $L_2$ may each independently be selected from a substituted or unsubstituted $C_3$-$C_{10}$ cycloalkylene group, a substituted or unsubstituted heterocycloalkylene group, a substituted or unsubstituted $C_3$-$C_{10}$ cycloalkenylene group, a substituted or unsubstituted heterocycloalkenylene group, a substituted or unsubstituted $C_6$-$C_{60}$ arylene group, a substituted or unsubstituted $C_1$-$C_{60}$ heteroarylene group, a substituted or unsubstituted divalent non-aromatic condensed polycyclic group, and a substituted or unsubstituted divalent non-aromatic condensed heteropolycyclic group, wherein $L_2$ does not include a cyano group.

For example, $L_1$ and $L_2$ may each independently be selected from:

a phenylene group, a pentalenylene group, an indenylene group, a naphthylene group, an azulenylene group, a heptalenylene group, an indacenylene group, an acenaphthylene group, a fluorenylene group, a spiro-bifluorenylene group, a phenalenylene group, a phenanthrenylene group, an anthracenylene group, a fluoranthrenylene group, a triphenylenylene group, a pyrenylene group, a chrysenylene group, a naphthacenylene group, a picenylene group, a perylenylene group, a pentaphenylene group, a hexacenylene group, a pyrrolylene group, an imidazolylene group, a pyrazolylene group, a pyridinylene group, a pyrazinylene group, a pyrimidinylene group, a pyridazinylene group, an isoindolylene group, an indolylene group, an indazolylene group, a purinylene group, a quinolinylene group, an isoquinolinylene group, a benzoquinolinylene group, a phthalazinylene group, a naphthyridinylene group, a quinoxalinylene group, a quinazolinylene group, a cinnolinylene group, a carbazolylene group, a phenanthridinylene group, an acridinylene group, a phenanthrolinylene group, a phenazinylene group, a benzoxazolylene group, a benzimidazolylene group, a furanylene group, a benzofuranylene group, a thiophenylene group, a benzothiophenylene group, a thiazolylene group, an isothiazolylene group, a benzothiazolylene group, an isoxazolylene group, an oxazolylene group, a triazolyl group, a tetrazolyl group, an oxadiazolylene group, a triazinylene group, a dibenzofuranylene group, a dibenzothiophenylene group, a benzocarbazolylene group, a dibenzocarbazolylene group, an imidazopyridimidinylene group, an imidazopyridinylene group, a pyridoindolylene group, a benzofuropyridinylene group, a benzothienopyridinylene group, a pyrimidoindolylene group, a benzofuropyrimidinylene group, a benzothienopyrimidinylene group, a phenoxazinylene group, a pyridobenzoxazinylene group, and a pyridobenzothiazinylene group; and a phenylene group, a pentalenylene group, an indenylene group, a naphthylene group, an azulenylene group, a heptalenylene group, an indacenylene group, an acenaphthylene group, a fluorenylene group, a spiro-bifluorenylene group, a phenalenylene group, a phenanthrenylene group, an anthracenylene group, a fluoranthrenylene group, a triphenylenylene group, a pyrenylene group, a chrysenylene group, a naphthacenylene group, a picenylene group, a perylenylene group, a pentaphenylene group, a hexacenylene group, a pyrrolylene group, an imidazolylene group, a pyrazolylene group, a pyridinylene group, a pyrazinylene group, a pyrimidinylene group, a pyridazinylene group, an isoindolylene group, an indolylene group, an indazolylene group, a purinylene group, a quinolinylene group, an isoquinolinylene group, a benzoquinolinylene group, a phthalazinylene group, a naphthyridinylene group, a quinoxalinylene group, a quinazolinylene group, a cinnolinylene group, a carbazolylene group, a phenanthridinylene group, an acridinylene group, a phenanthrolinylene group, a phenazinylene group, a benzoxazolylene group, a benzimidazolylene group, a furanylene group, a benzofuranylene group, a thiophenylene group, a benzothiophenylene group, a thiazolylene group, an isothiazolylene group, a benzothiazolylene group, an isoxazolylene group, an oxazolylene group, a triazolyl group, a tetrazolyl group, an oxadiazolylene group, a triazinylene group, a dibenzofuranylene group, a dibenzothiophenylene group, a benzocarbazolylene group, a dibenzocarbazolylene group, an imidazopyridimidinylene group, an imidazopyridinylene group, a pyridoindolylene group, a benzofuropyridinylene group, a benzothienopyridinylene group, a pyrimidoindolylene group, a benzofuropyrimidinylene group, a benzothienopyrimidinylene group, a phenoxazinylene group, a pyridobenzoxazinylene group, and a pyridobenzothiazinylene group, each substituted with at least one selected from deuterium, a cyano group, a hydroxyl group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_2$-$C_{20}$ alkenyl group, a $C_2$-$C_{20}$ alkynyl group, a $C_1$-$C_{20}$ alkoxy group, a phenyl group, a biphenyl group, a terphenyl group, a naphthyl group, an anthracenyl group, a pyrenyl group, a phenanthrenyl group, a fluorenyl group, a carbazolyl group, a benzocarbazolyl group, a dibenzocarbazolyl group, a pyridinyl group, a pyrimidinyl group, a pyrazinyl group, a pyridazinyl group, a triazinyl group, a quinolinyl group, an isoquinolinyl group, a phthalazinyl group, a quinoxalinyl group, a cinnolinyl group, a quinazolinyl group, and —Si($Q_{31}$)($Q_{32}$)($Q_{33}$), and $Q_{31}$ to $Q_{33}$ may each independently be selected from hydrogen, $C_1$-$C_{20}$ alkyl group, a $C_1$-$C_{20}$ alkoxy group, a phenyl group, a biphenyl group, a terphenyl group, a naphthyl group, a fluorenyl group, a carbazolyl group, a dibenzofuranyl group, and a dibenzothiophenyl group.

In various embodiments, $L_1$ and $L_2$ may each independently be selected from:

a phenylene group, a fluorenylene group, a spiro-bifluorenylene group, a pyridinylene group, a carbazolylene group, a dibenzofuranylene group, and a dibenzothiophenylene group; and a phenylene group, a fluorenylene group, a spiro-bifluorenylene group, a pyridinylene group, a carbazolylene group, a dibenzofuranylene group, and a dibenzothiophenylene group, each substituted with at least one selected from deuterium, a cyano group, a $C_1$-$C_{10}$ alkyl group, a phenyl group, a biphenyl group, and a terphenyl group.

In various embodiments, $L_1$ and $L_2$ may each independently be selected from groups represented by Formulae 3-1 to 3-15:

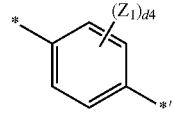

Formula 3-1

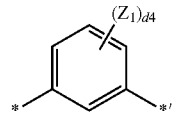

Formula 3-2

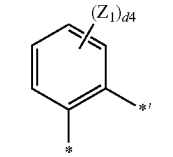

Formula 3-3

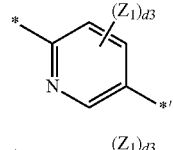

Formula 3-4

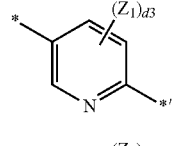

Formula 3-5

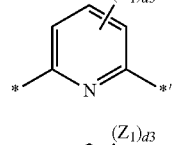

Formula 3-6

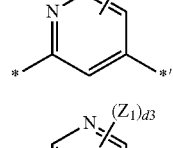

Formula 3-7

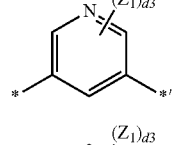

Formula 3-8

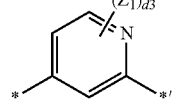

Formula 3-9

-continued

Formula 3-10
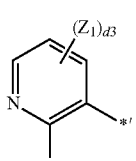

Formula 3-11
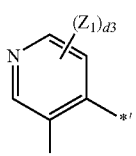

Formula 3-12
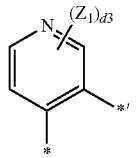

Formula 3-13
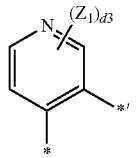

Formula 3-14
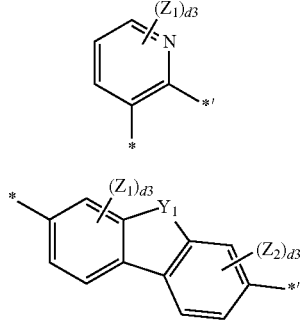

Formula 3-15
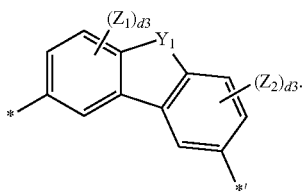

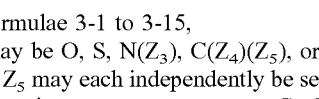

In Formulae 3-1 to 3-15, $Y_1$ may be O, S, $N(Z_3)$, $C(Z_4)(Z_5)$, or $Si(Z_4)(Z_5)$, $Z_1$ to $Z_5$ may each independently be selected from hydrogen, deuterium, a cyano group, a $C_1$-$C_{10}$ alkyl group, a phenyl group, a biphenyl group, and a terphenyl group, d3 may be an integer selected from 0 to 3, d4 may be an integer selected from 0 to 4, and

* and *' each independently indicate a binding site to a neighboring atom.

In Formula 1, b1 and b2 may respectively indicate the number of groups $L_1$ and the number of groups $L_2$, and may each independently be an integer selected from 0 to 5, wherein, when b1 is 0, *-$(L_1)_{b1}$-*' may be a single bond, when b1 is 2 or more, 2 or more groups $L_1$ may be identical to or different from each other, when b2 is 0, *-$(L_2)_{b2}$-*' may be a single bond, and when b2 is 2 or more, 2 or more groups $L_2$ may be identical to or different from each other.

For example, b1 and b2 may each independently be 0 or 1, but embodiments are not limited thereto.

In Formula 1, c1 indicates the number of groups *-$(L_2)_{b2}$-$(R_{12})_{a12}$, and may be an integer selected from 0 to 4. For example, c1 may be 0, 1, or 2, and for example, may be 0 or 1. However, embodiments are not limited thereto.

In the condensed cyclic compound represented by Formula 1, the number of carbazole ring(s) may be 0, 1, or 2.

In an embodiment, in Formula 1, a group represented by

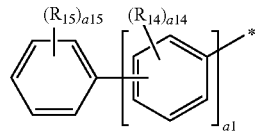

may be represented by one selected from Formulae 6-1 to 6-4:

Formula 6-1
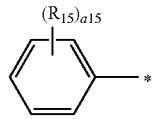

Formula 6-2
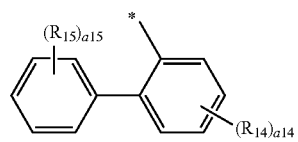

Formula 6-3
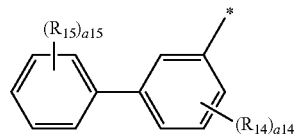

Formula 6-4
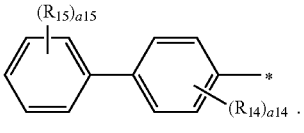

In Formulae 6-1 to 6-4, $R_{14}$, $R_{15}$, a14, and a15 may each independently be the same as described elsewhere herein in connection with those provided in the present specification, and * indicates a binding site to a neighboring atom.

The condensed cyclic compound represented by Formula 1 has an asymmetrical structure. The term "asymmetrical structure" used herein may refer to a molecular structure not having a symmetrical line or point, which makes the molecular structure in a "symmetrical" structure.

For example, Compounds A, A', and A" each have a symmetrical line shown in a "broken line", and that is, Compounds A, A', and A" has not an "asymmetrical structure", but a "symmetrical structure":

A

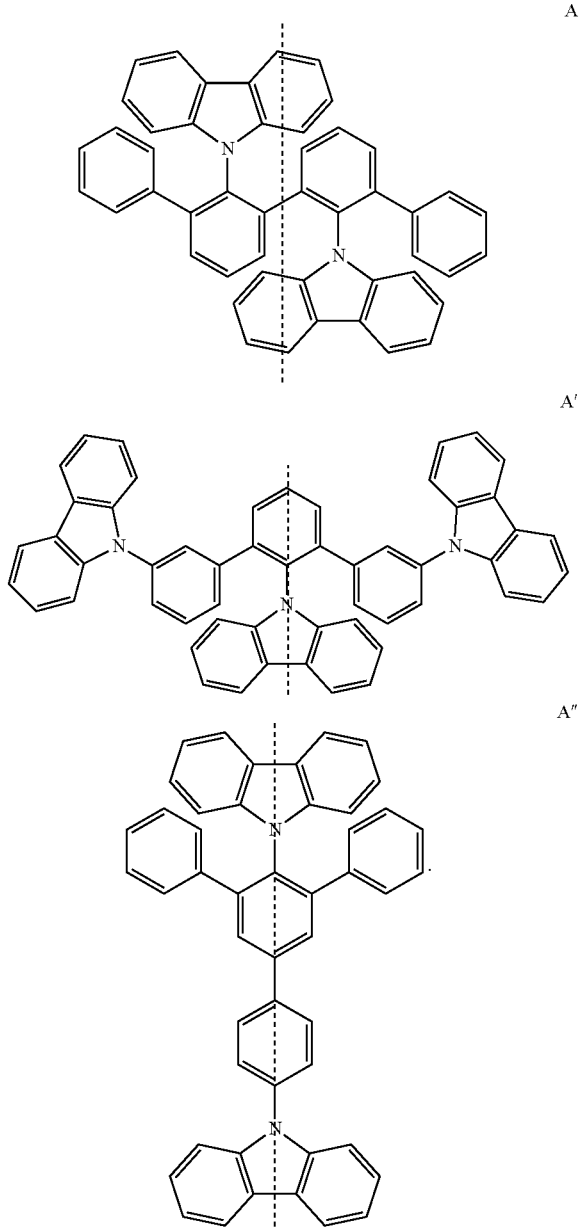

A'

A"

In an embodiment, the condensed cyclic compound represented by Formula 1 may be represented by one selected from Formulae 1-1 to 1-3:

Formula 1-1

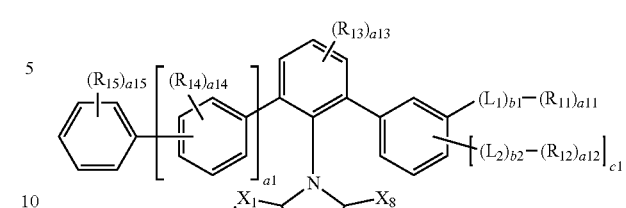

Formula 1-2

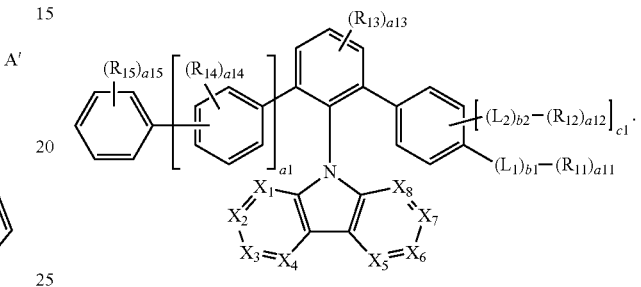

Formula 1-3

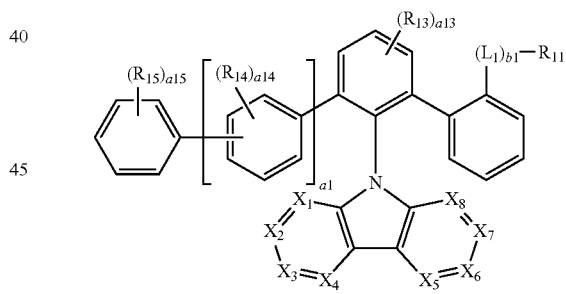

In Formulae 1-1 to 1-3, $X_1$ to $X_8$, a1, $R_{11}$ to $R_{15}$, a11 to a15, $L_1$, $L_2$, b1, b2, and c1 may each independently be the same as described elsewhere herein in connection with those provided in the present specification.

In various embodiments, the condensed cyclic compound represented by Formula 1 may be represented by one selected from Formulae 1-1A to 1-1D, 1-2A to 1-2D, and 1-3A to 1-3D, but embodiments are not limited thereto:

Formula 1-1A

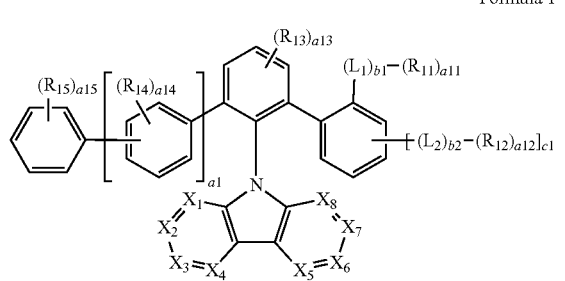

Formula 1-1B

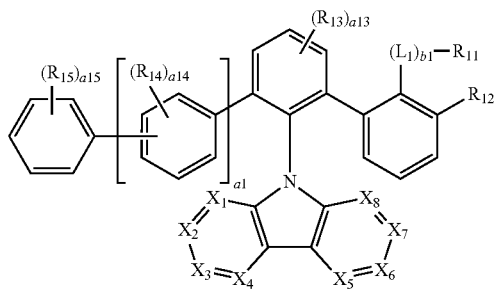

Formula 1-1C
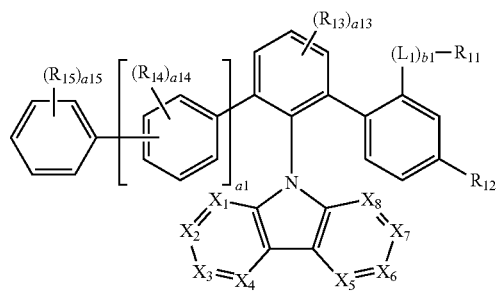
Formula 1-1D
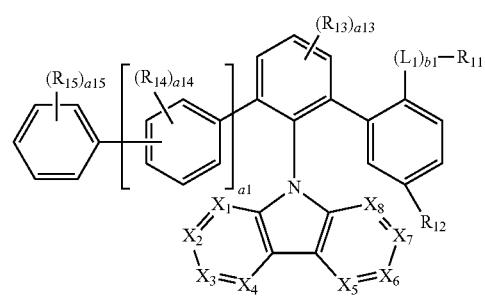
Formula 1-2A
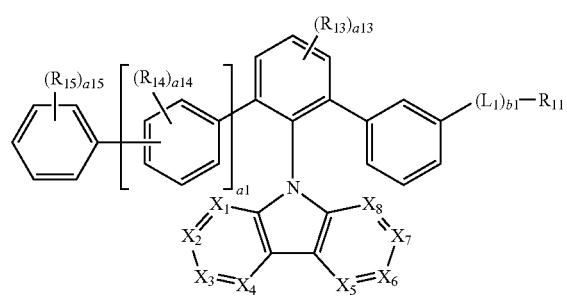
Formula 1-2B
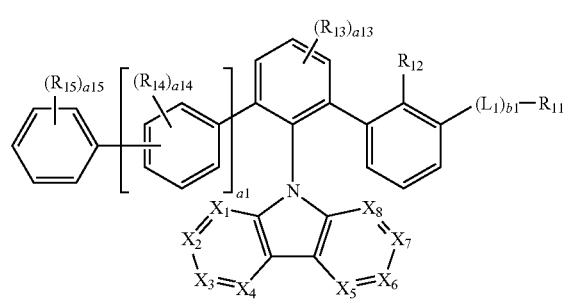
Formula 1-2C
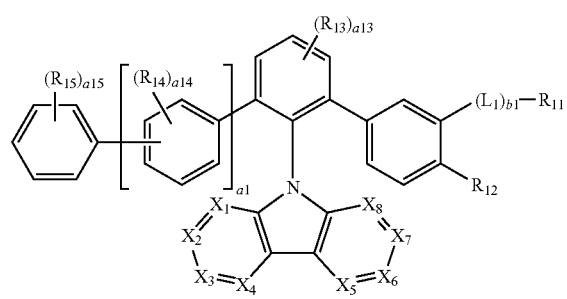
Formula 1-2D
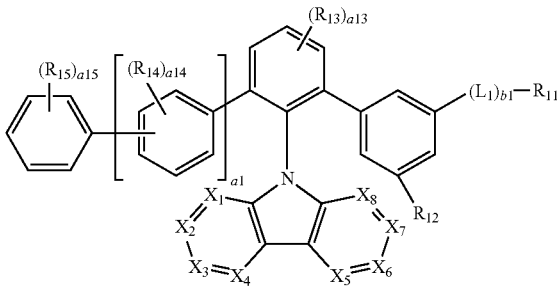
Formula 1-3A
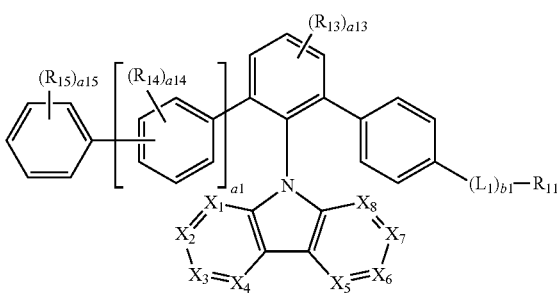
Formula 1-3B
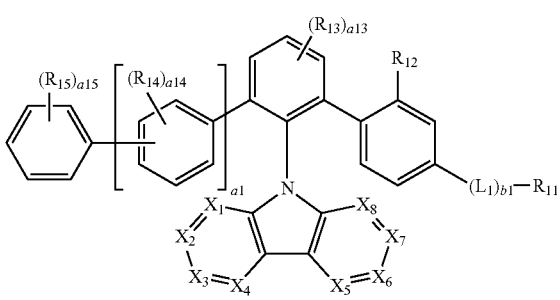
Formula 1-3C
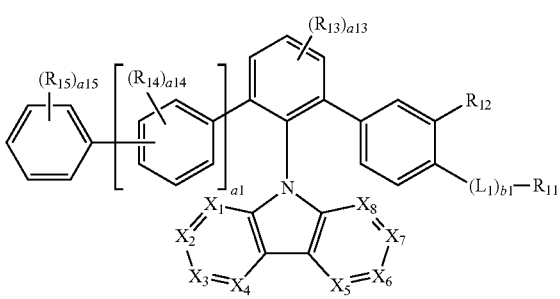
Formula 1-3D
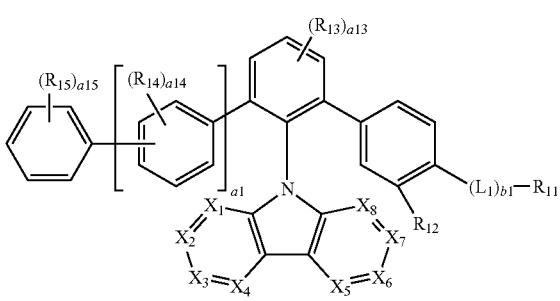
In Formulae 1-1A to 1-1D, 1-2A to 1-2D, and 1-3A to 1-3D, $X_1$ to $X_8$, a1, $R_{11}$ to $R_{15}$, a13 to a15, $L_1$, b1, and c1 may each independently be the same as described elsewhere herein in connection with those provided in the present specification, wherein $R_{12}$ is not hydrogen.

In the condensed cyclic compound represented by Formula 1, the number of cyano group(s) may be 0, 1, 2, 3, or 4, and for example, may be 0, 1, 2, or 3. For example, in the condensed cyclic compound represented by Formula 1, the number of cyano group(s) may be 0, 1, or 2.

For example, the condensed cyclic compound represented by Formula 1 may be one selected from Compounds 1 to 135, but embodiments are not limited thereto:

1
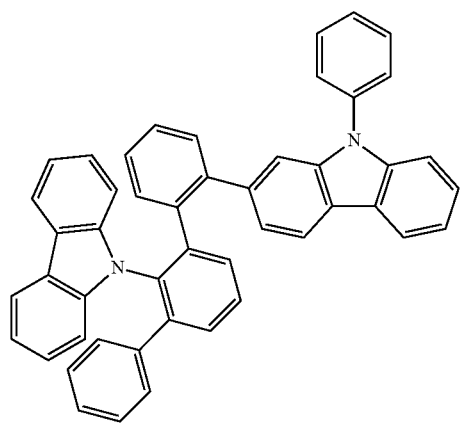

2
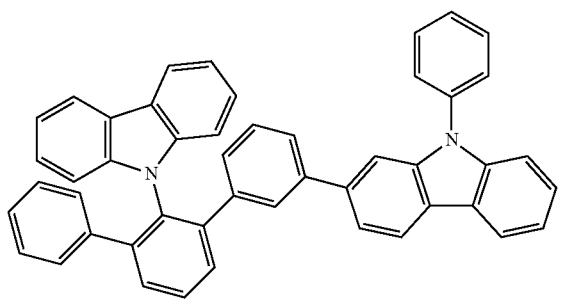

3
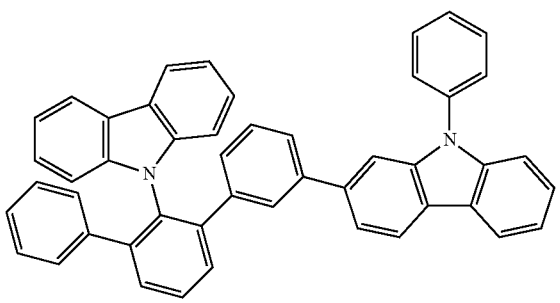

4
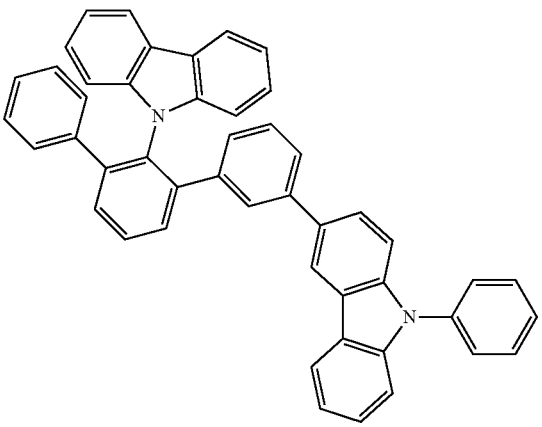

5
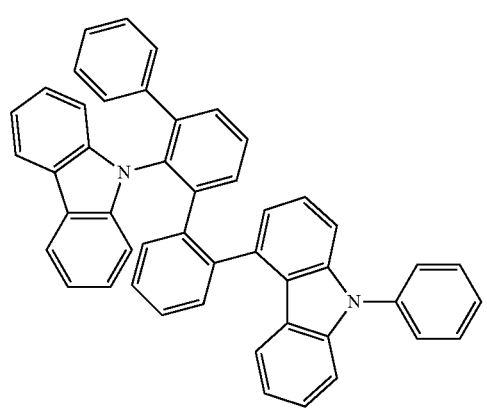

6
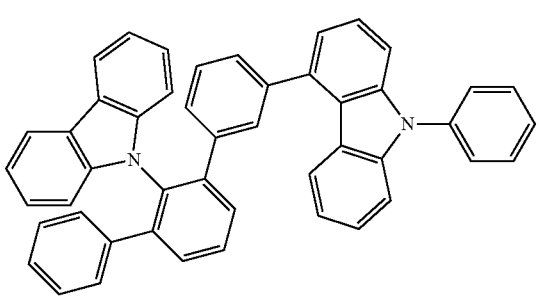

7
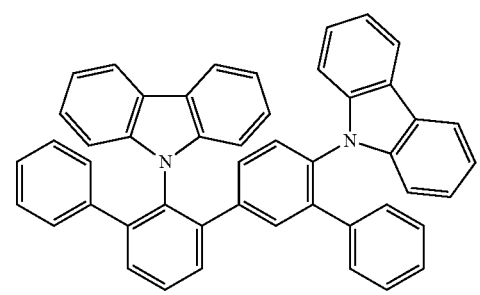

8
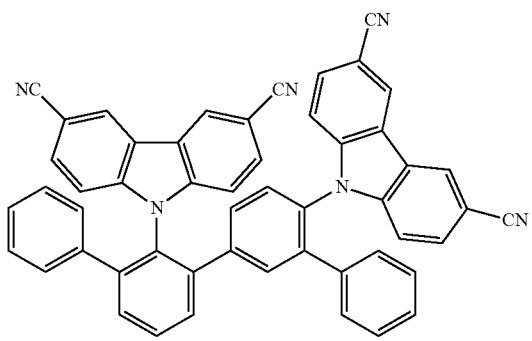
9
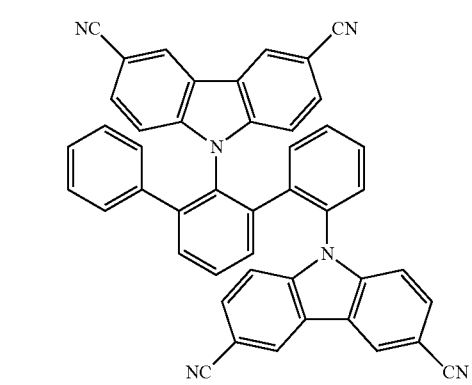
10
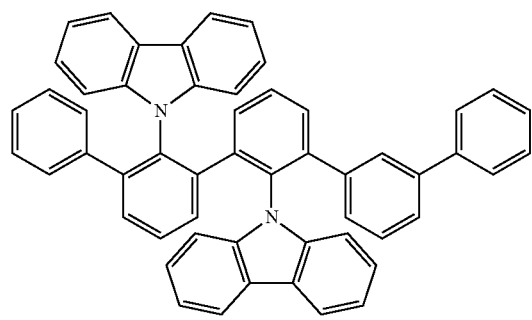
11
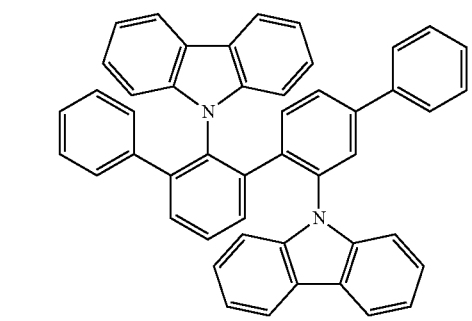
12
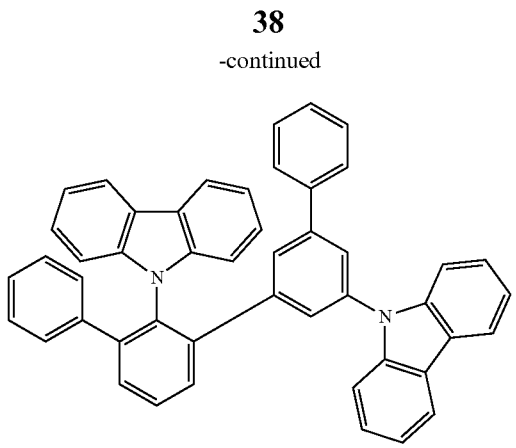
13
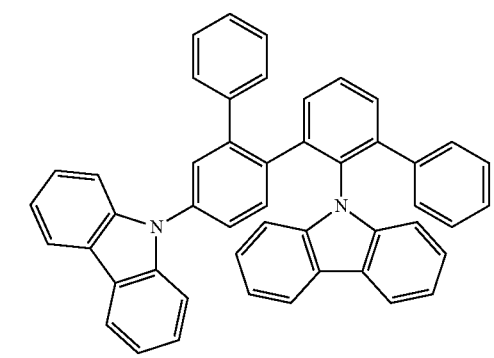
14
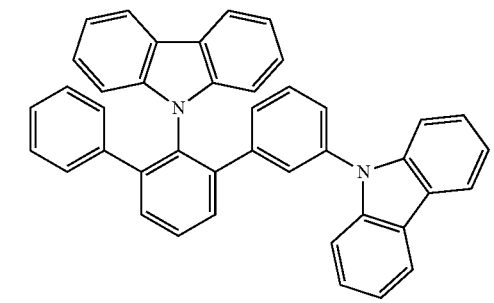
15
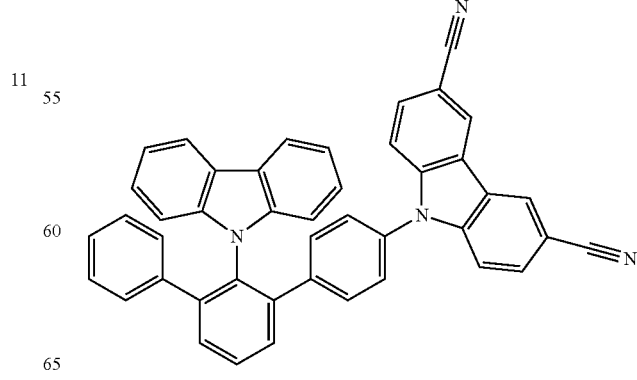

16
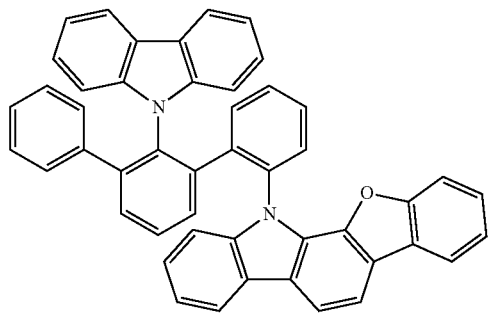
17
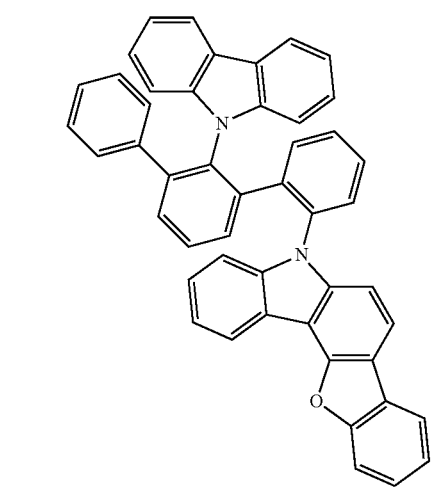
18
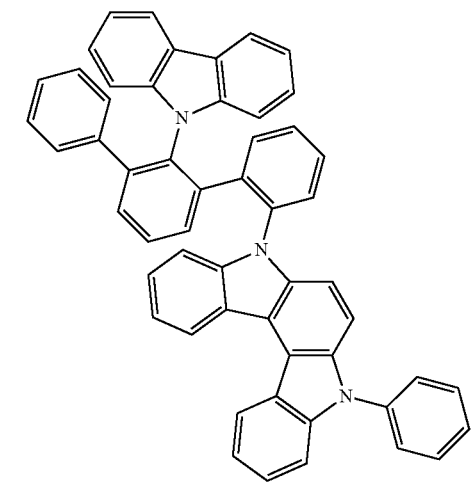
19
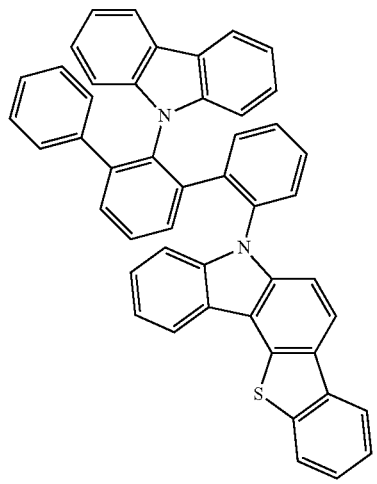
20
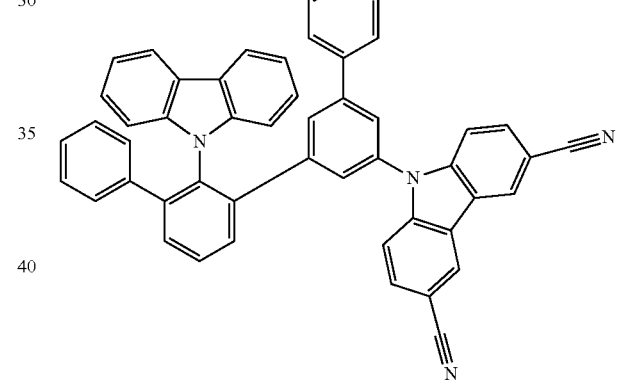
21

22
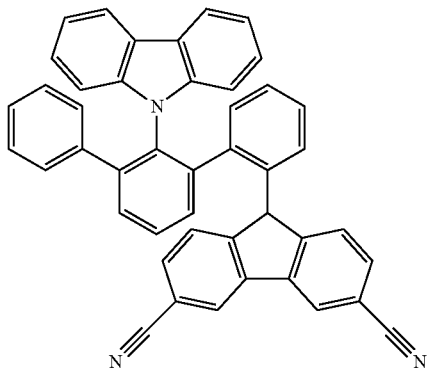
23
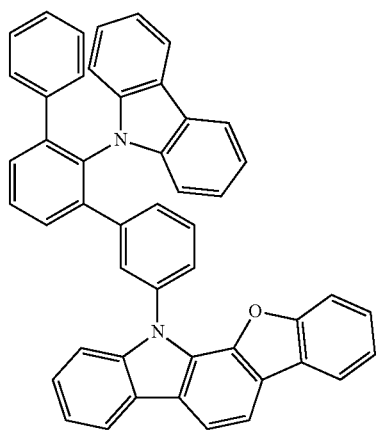
24
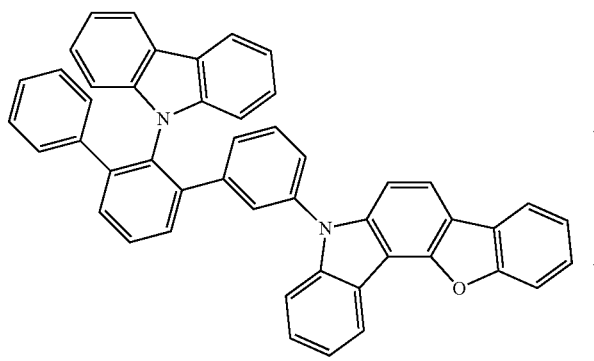
25
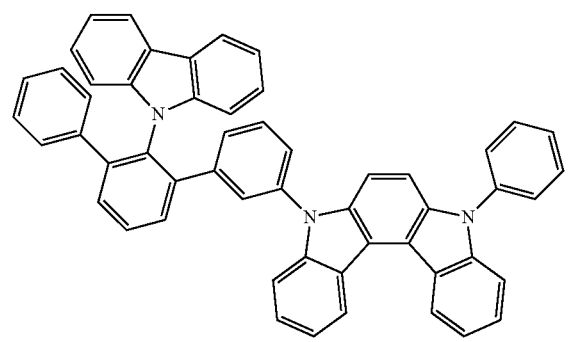
26
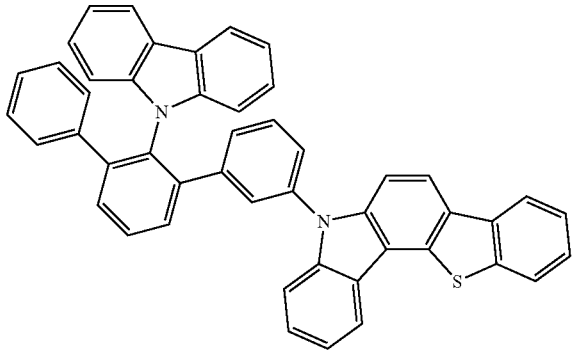
27
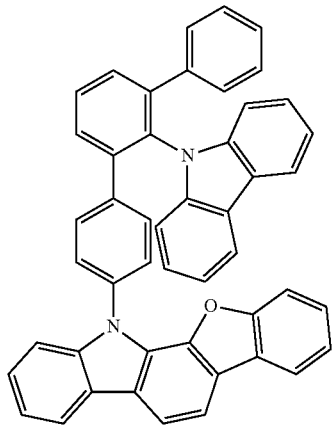
28
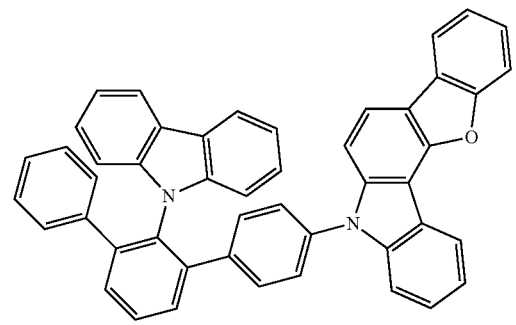
29
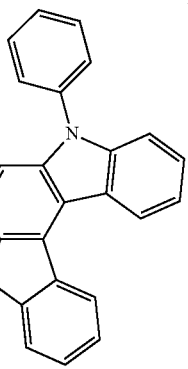

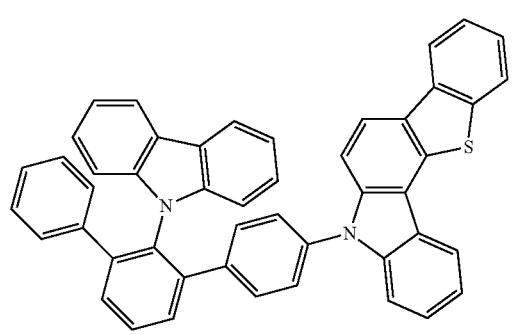
30
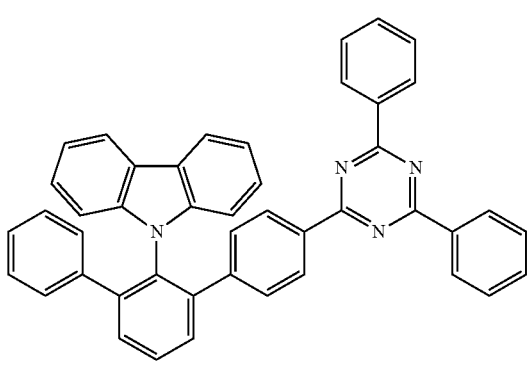
31
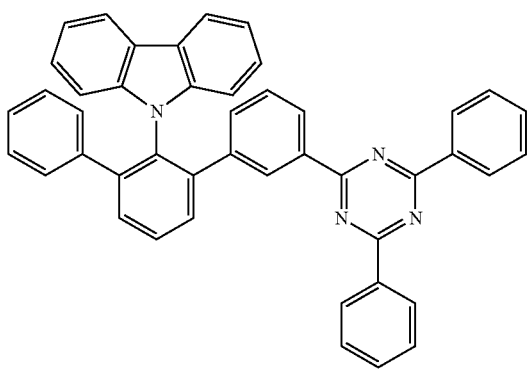
32
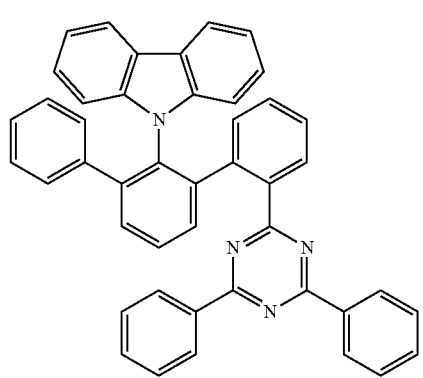
33
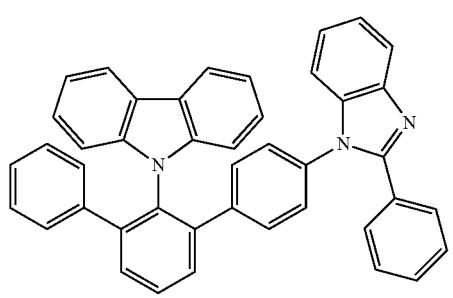
34
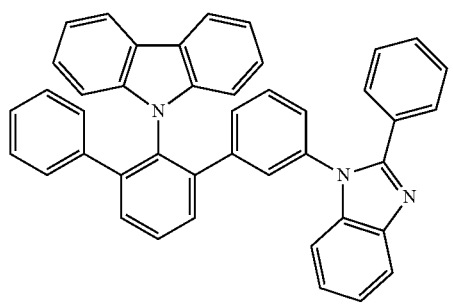
35
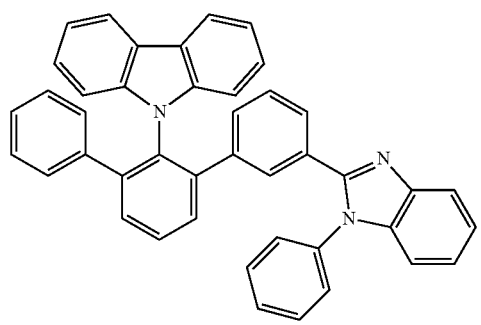
36
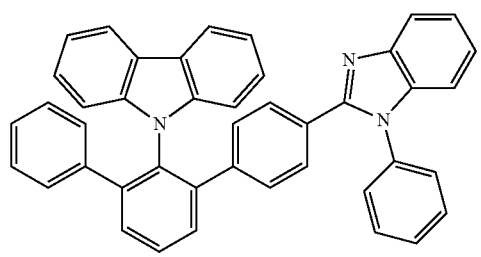
37
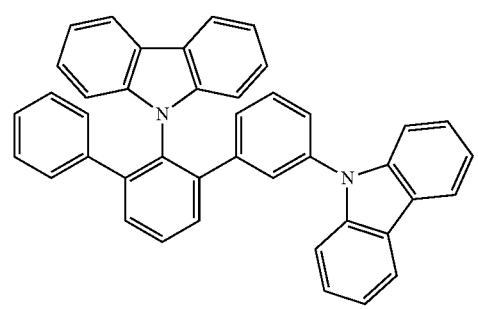
38

39
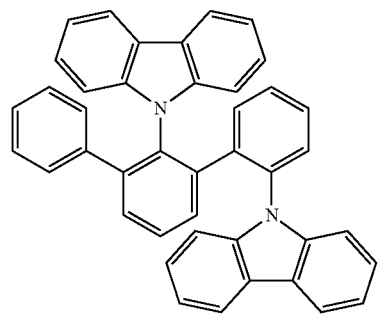
40
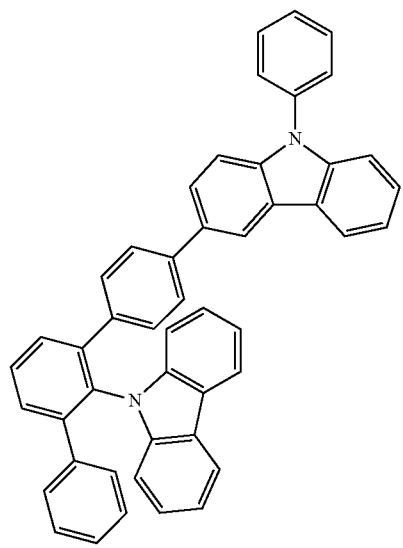
41
42
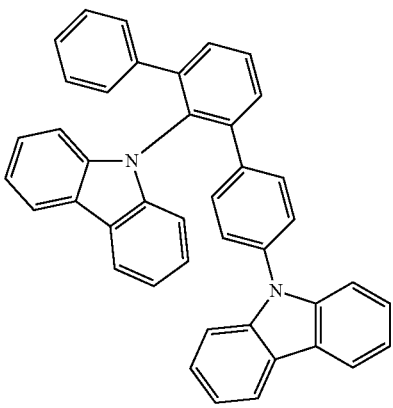
43
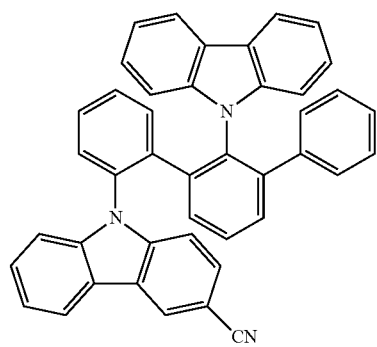
44
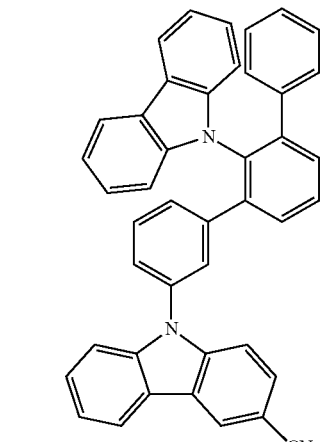
45
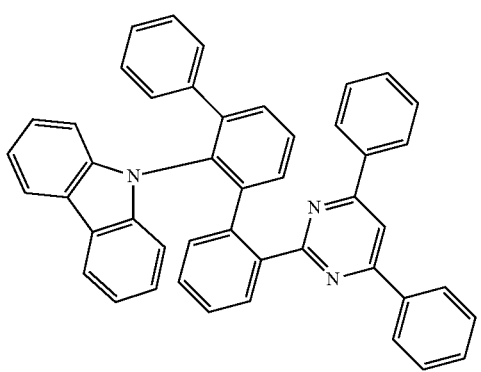

46
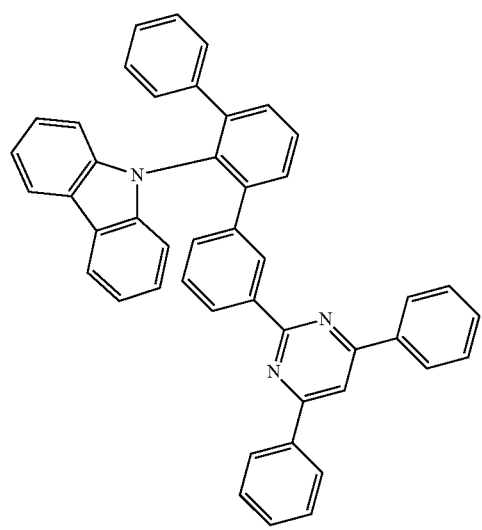
47
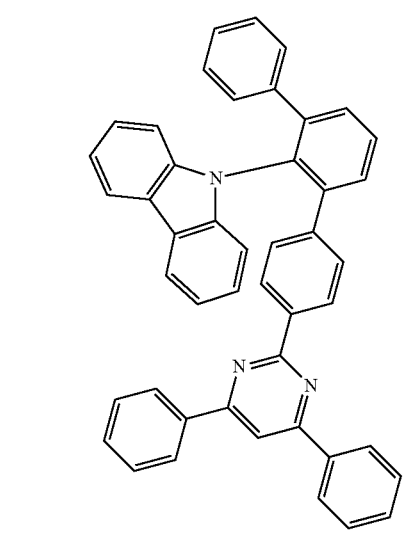
48
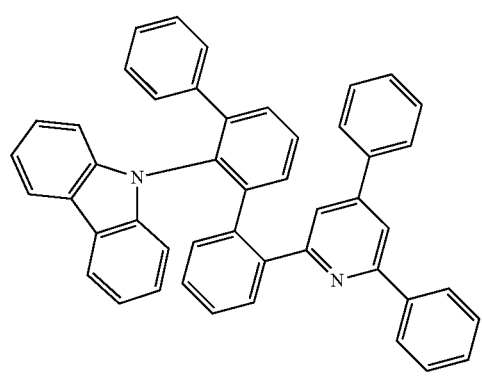
49
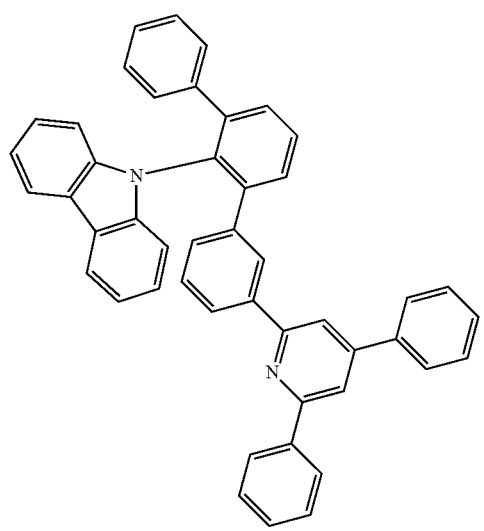
50
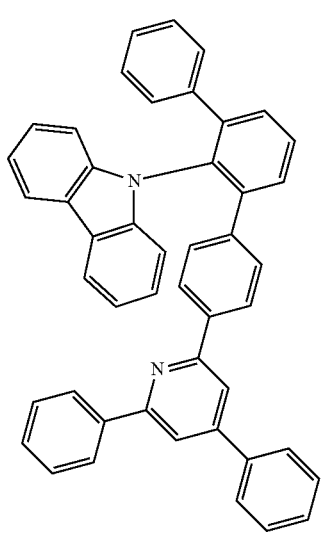
51
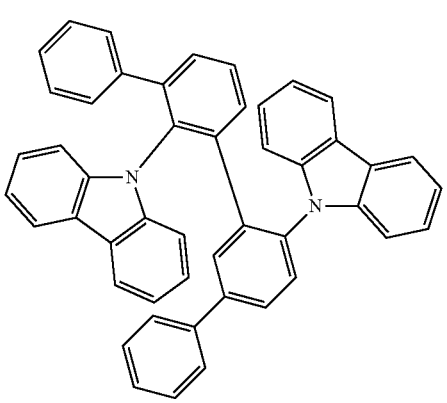

52
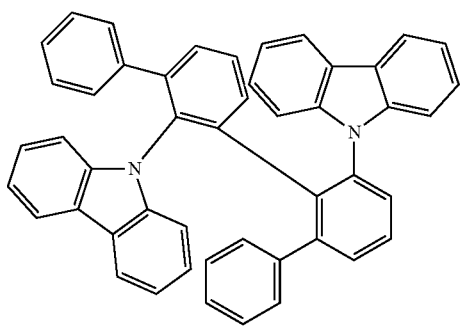
53
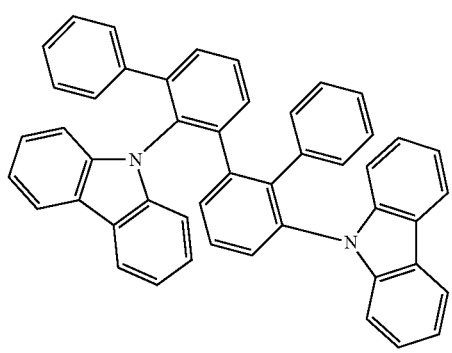
54
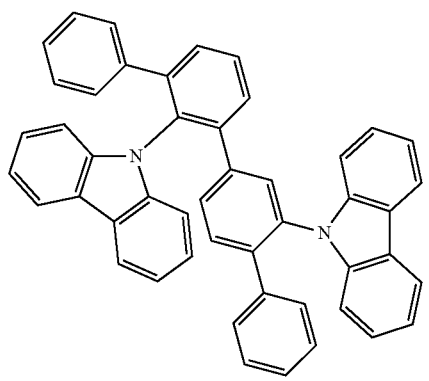
55
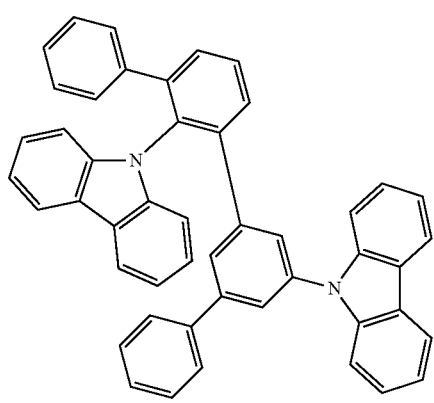
56
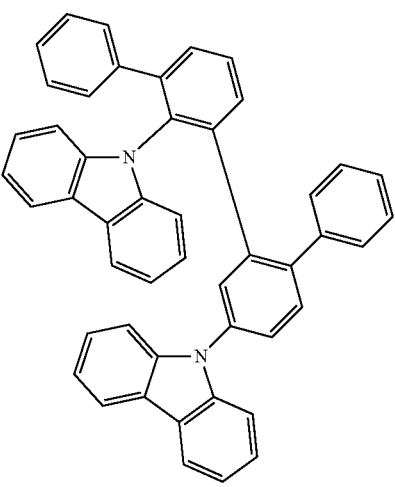
57
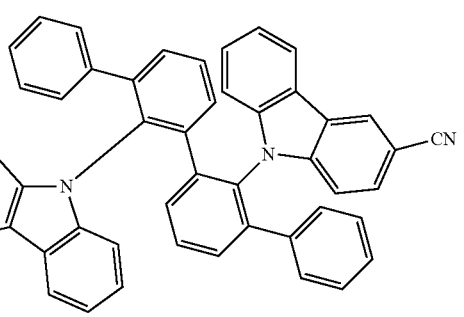
58
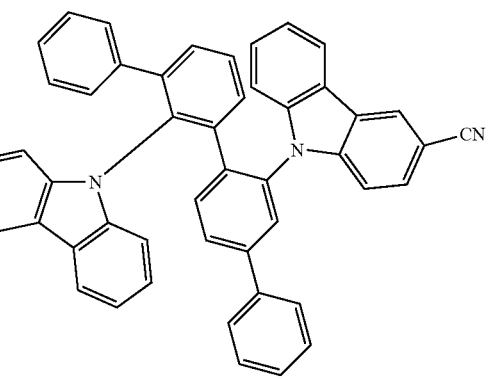
59
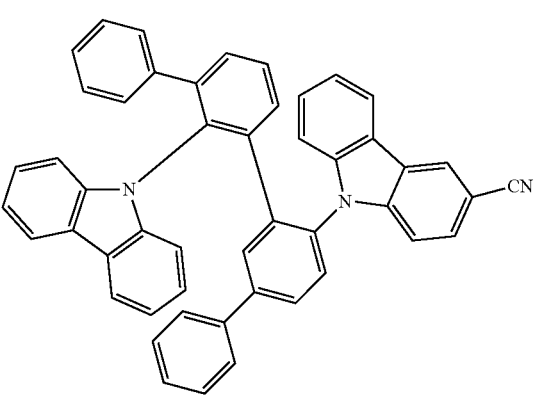

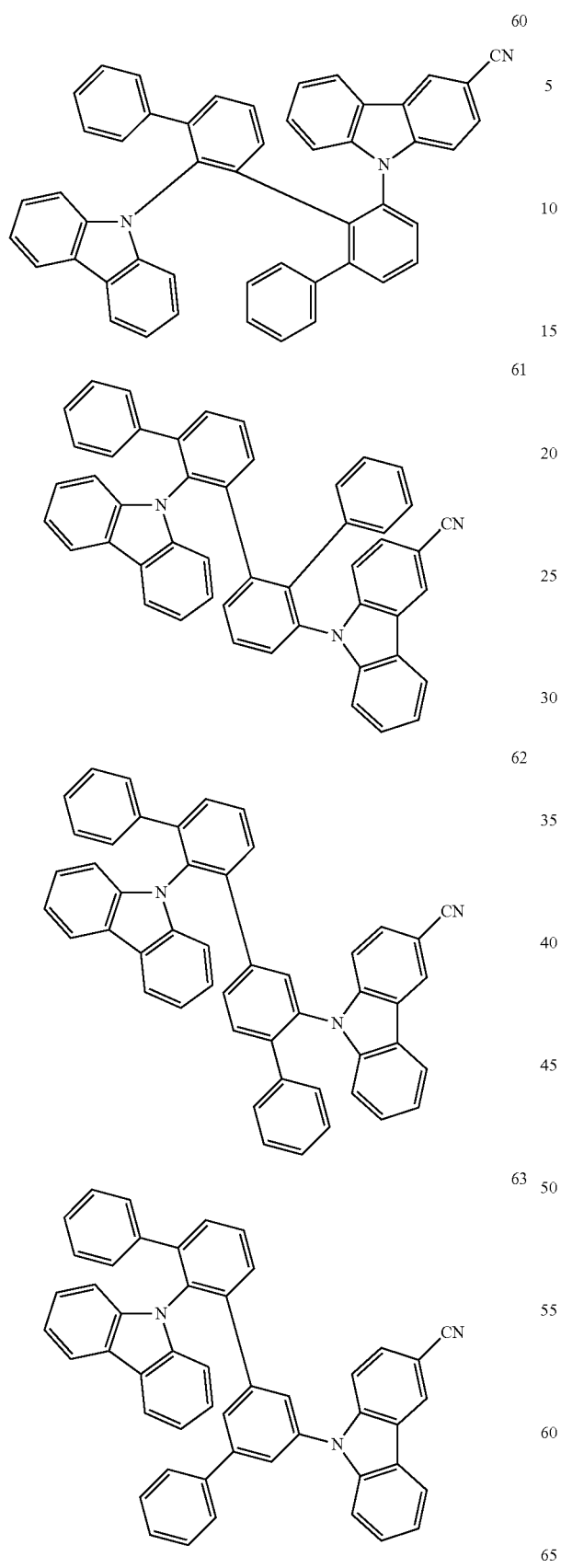
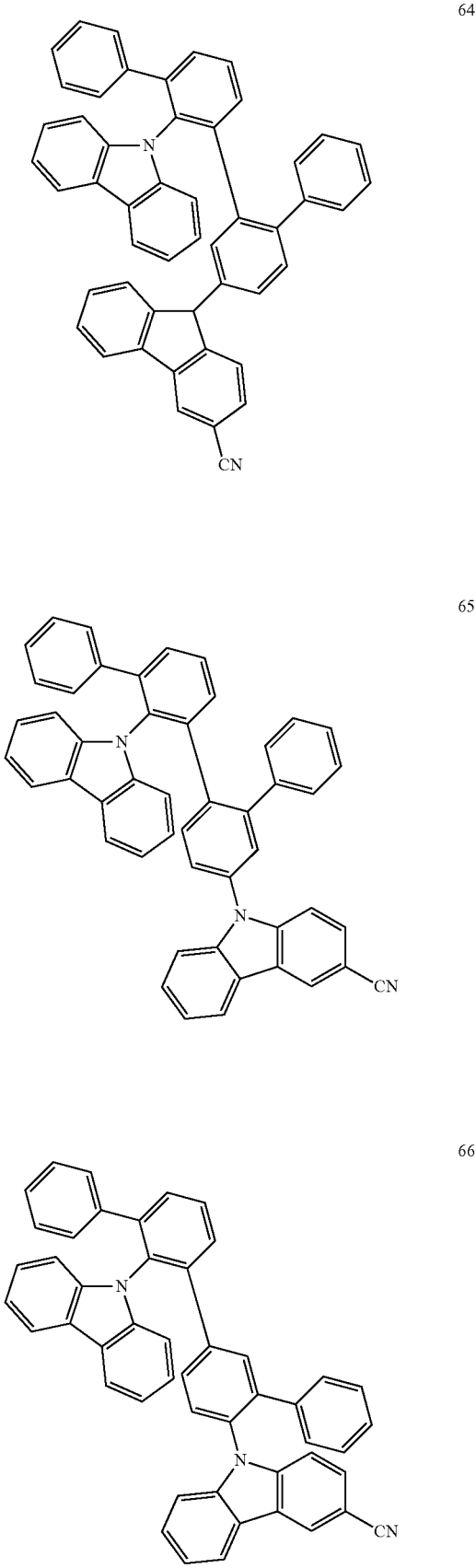

67
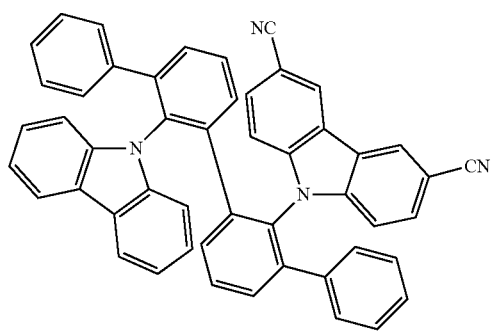
68
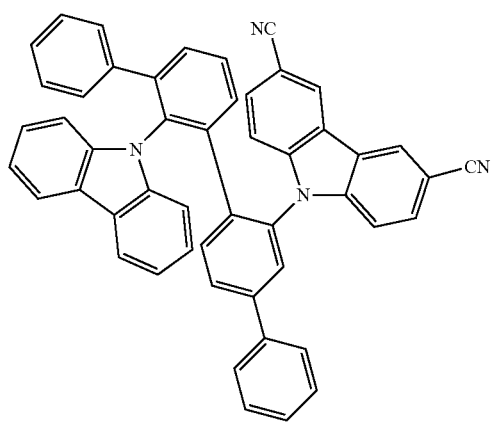
69
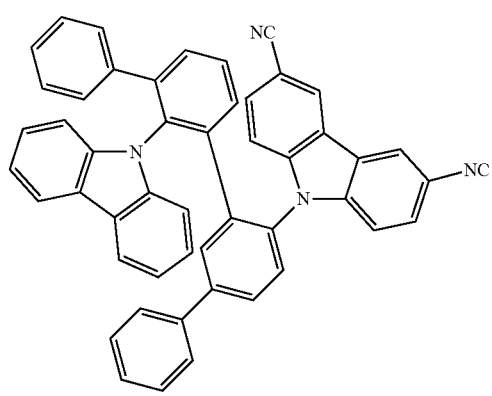
70
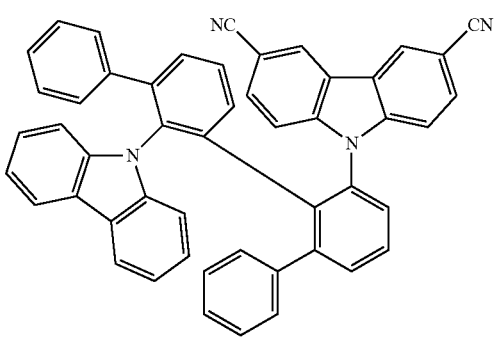
71
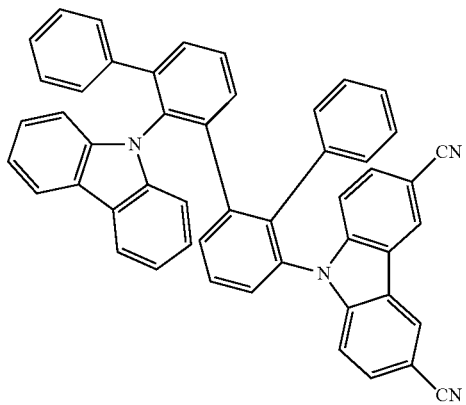
72
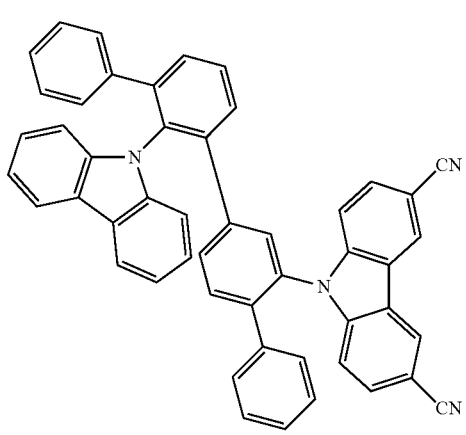
73
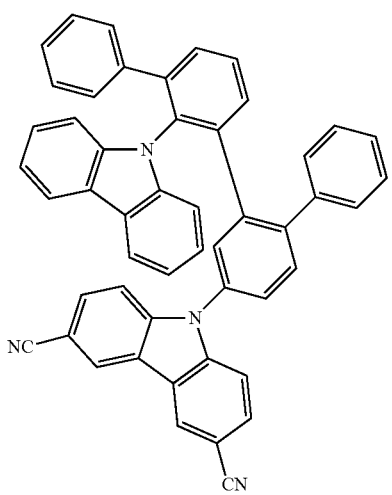

74
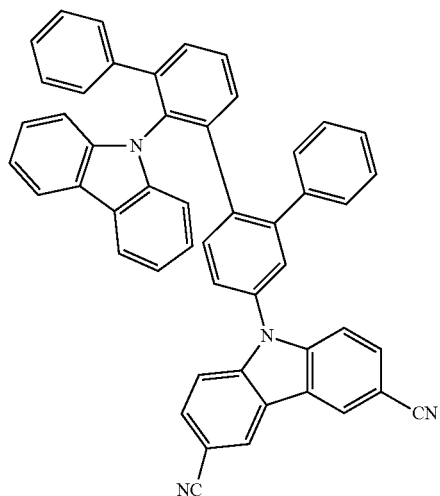
75
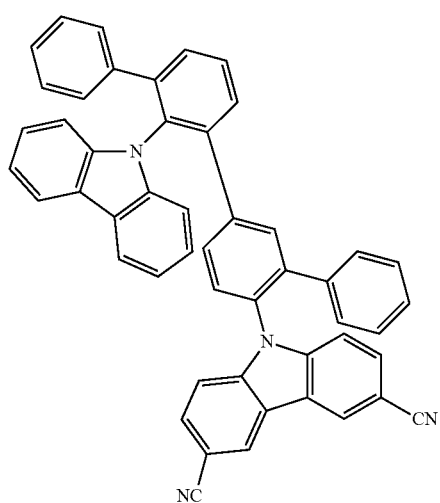
76
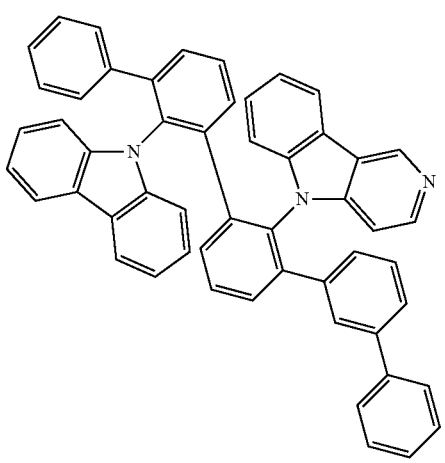
77
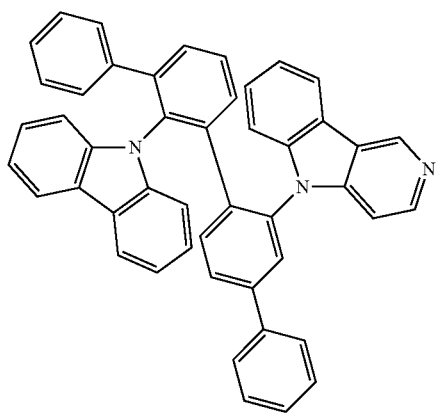
78
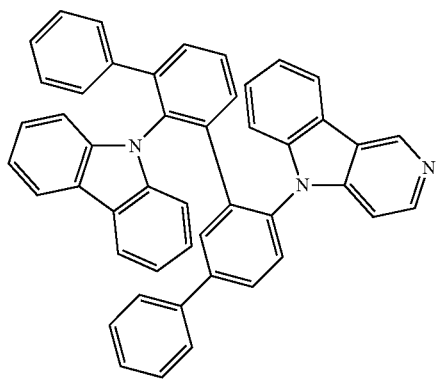
79
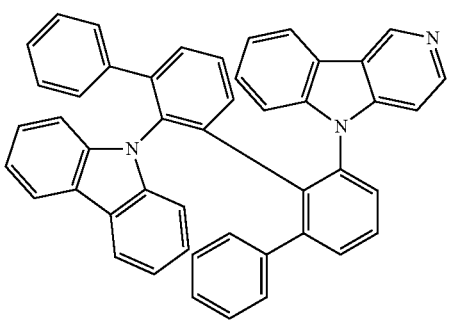
80
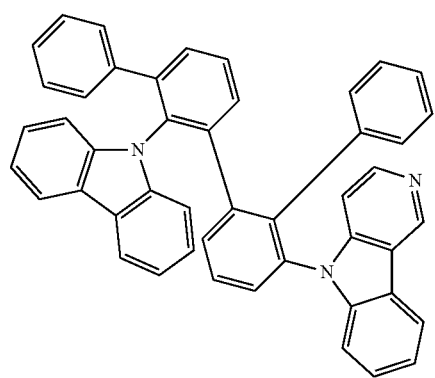

81
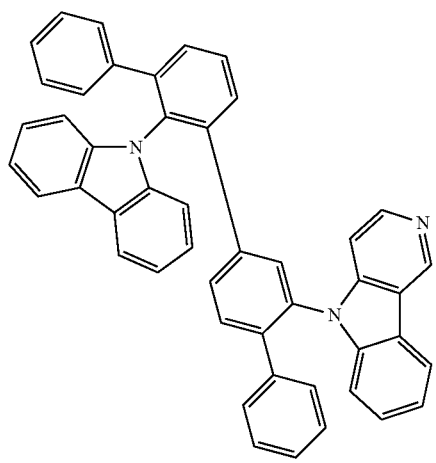
82
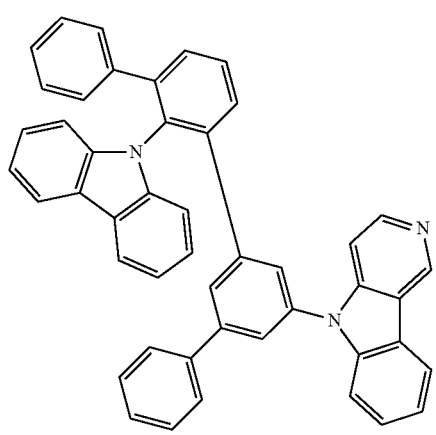
83
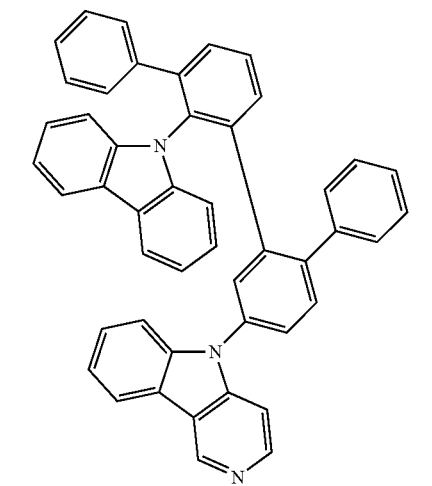
84
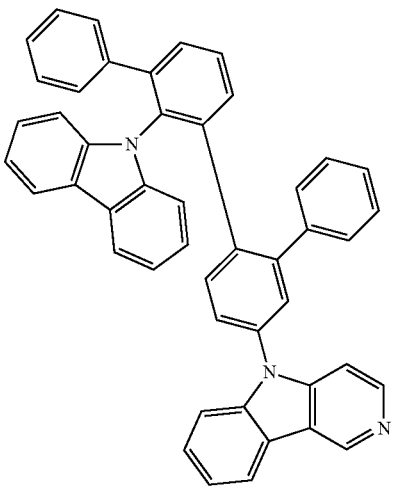
85
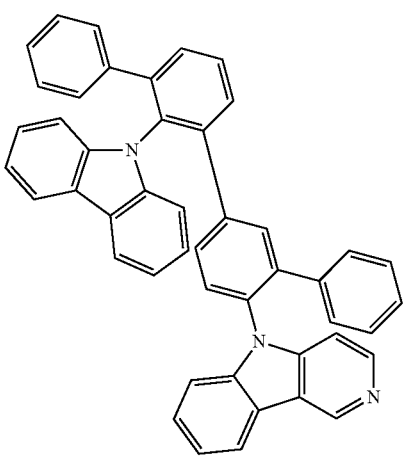
86
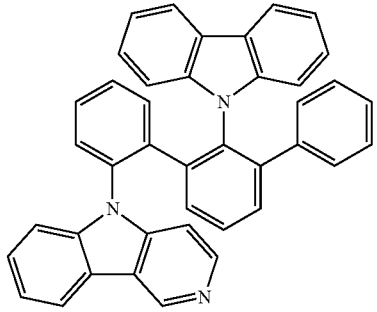

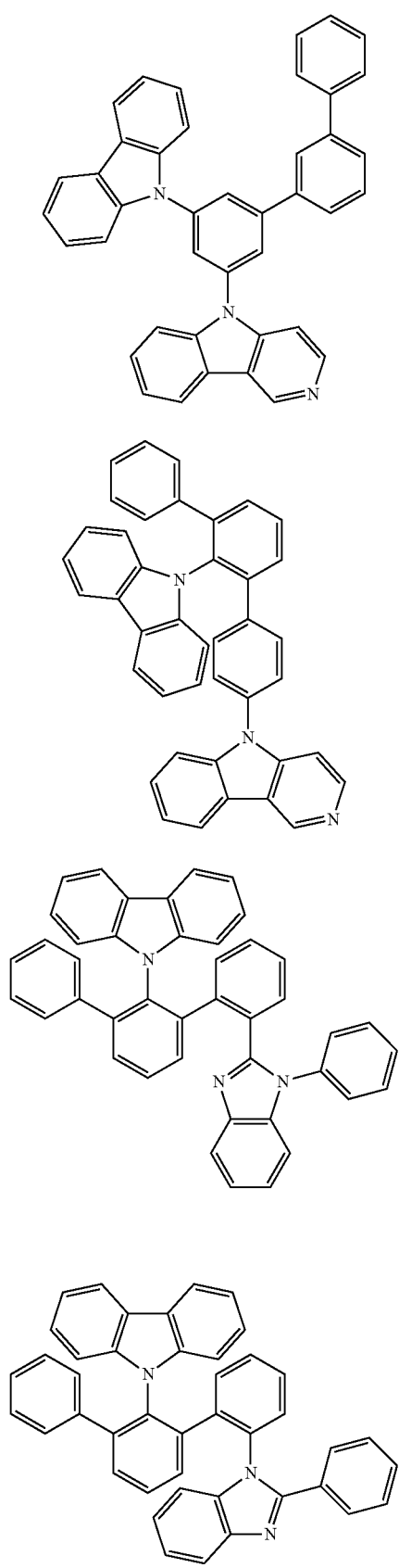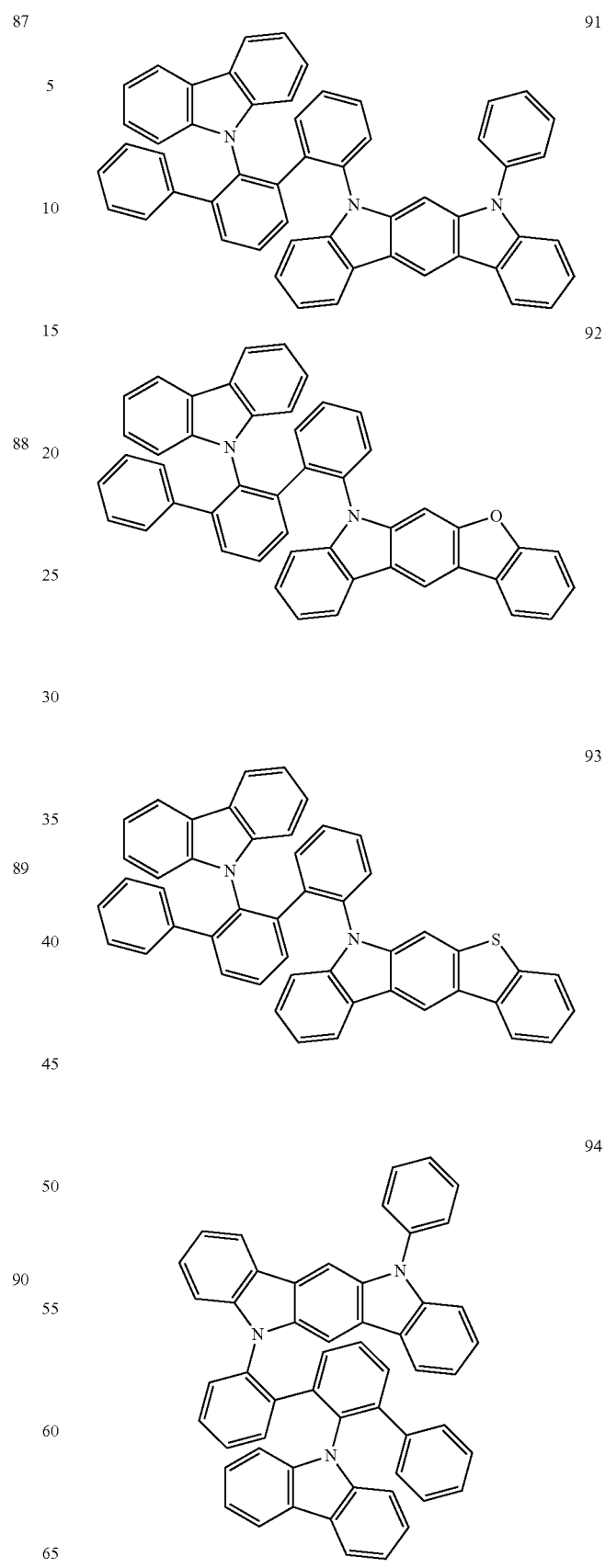

-continued
95
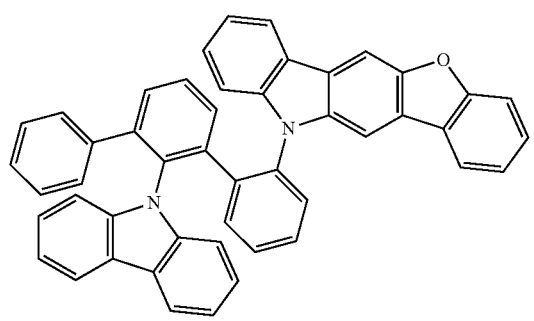
96
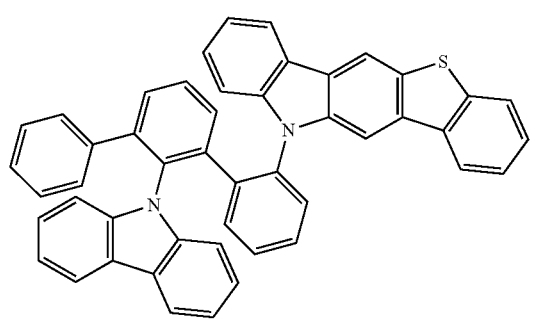
97
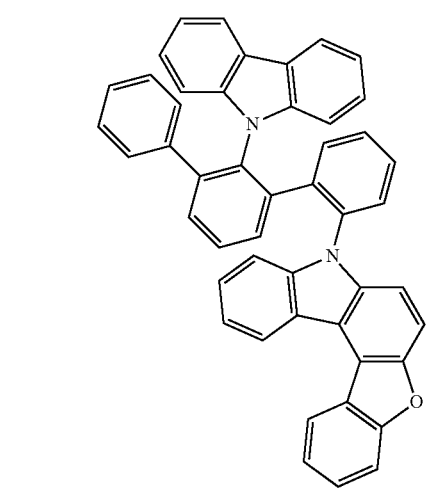
98
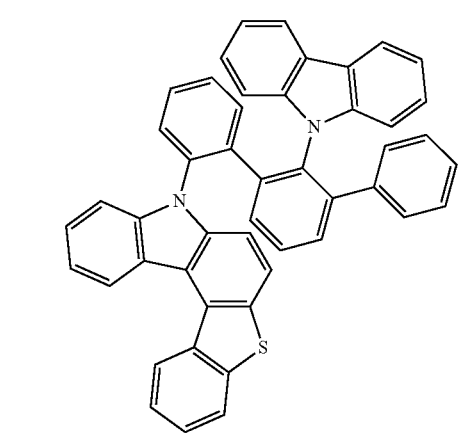
-continued
99
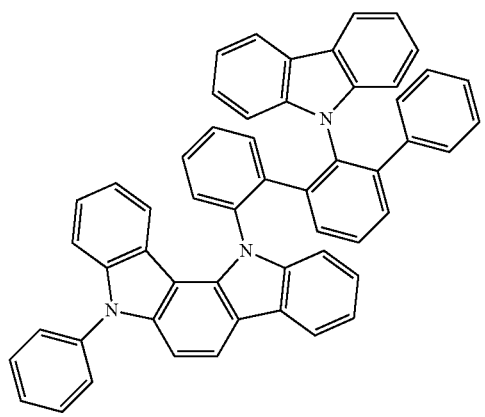
100
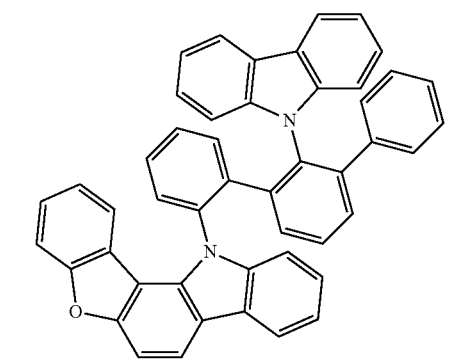
101
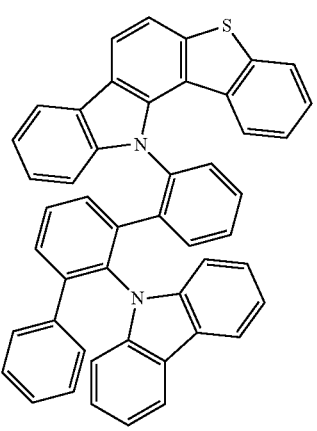
102
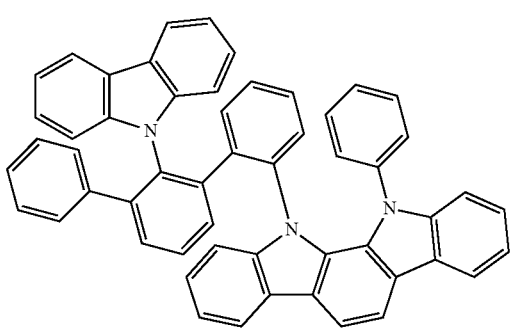

103
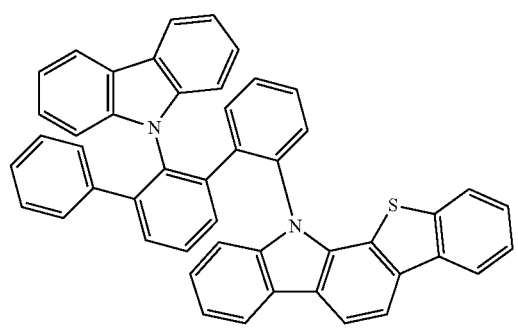
104
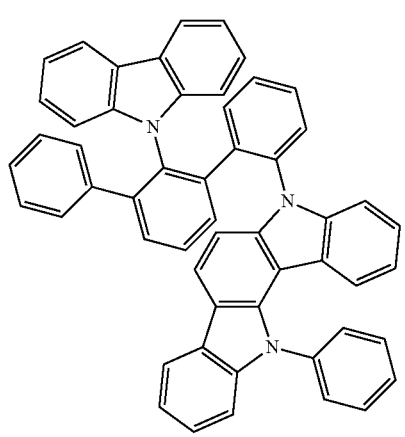
105
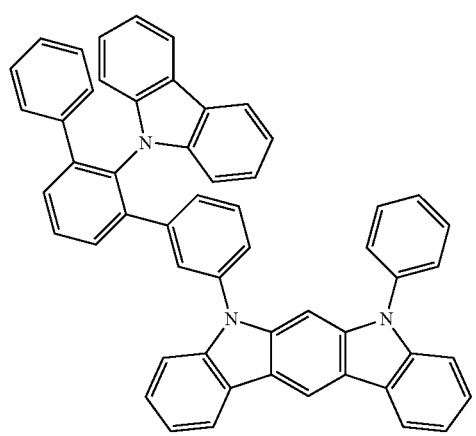
106
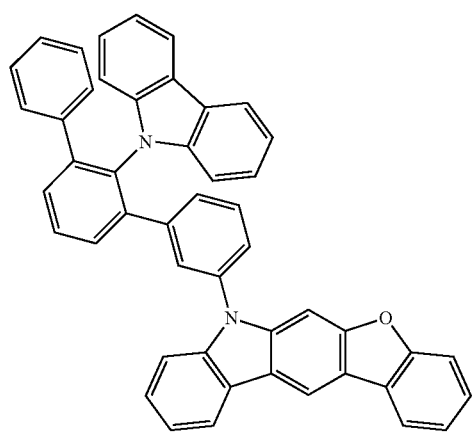
107
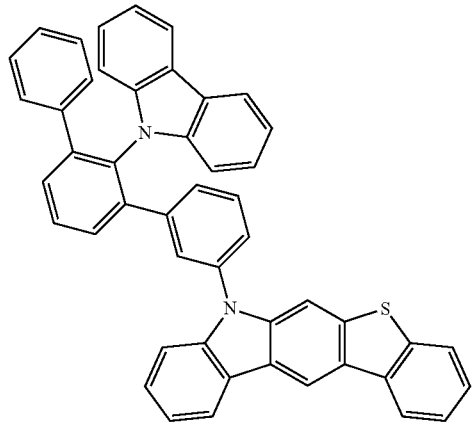
108
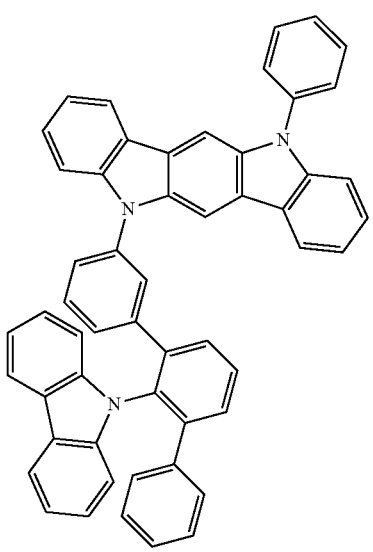
109
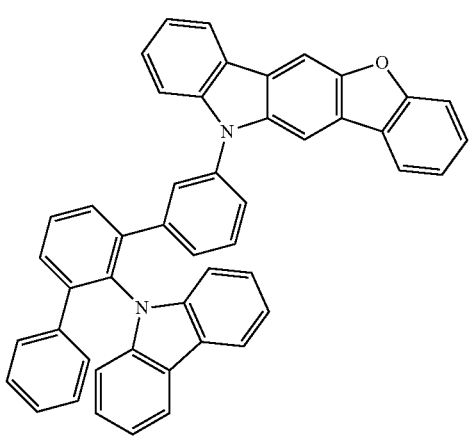

110
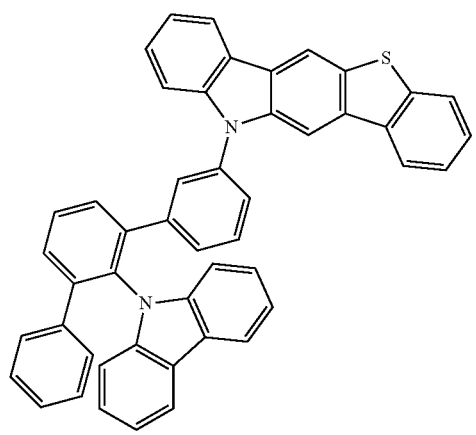
111
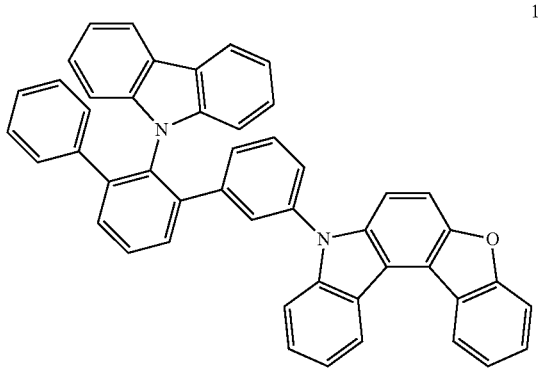
112
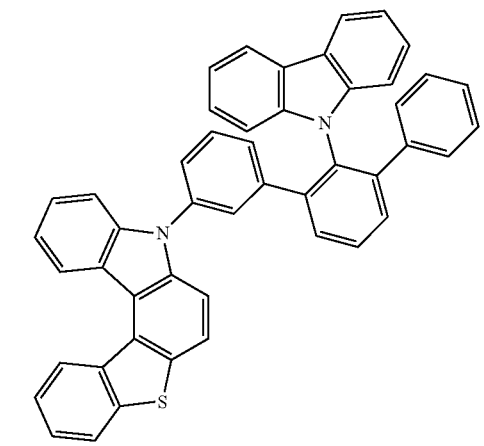
113
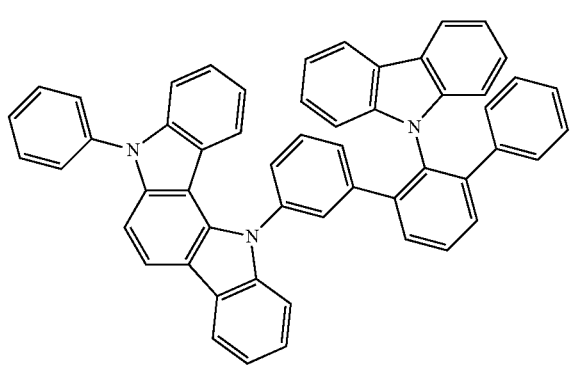
114
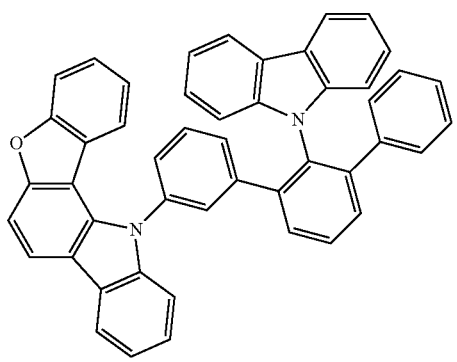
115
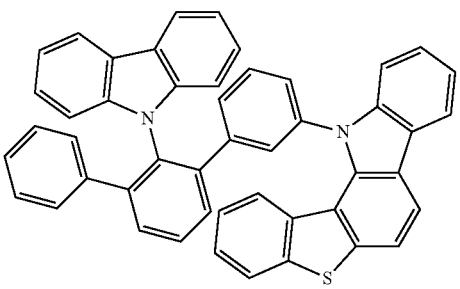
116
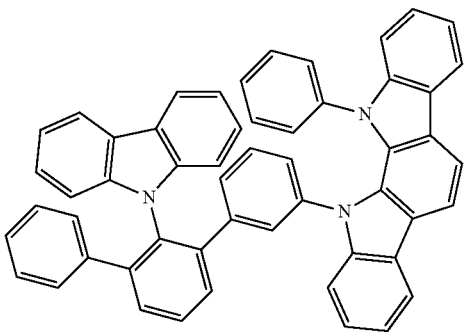
117
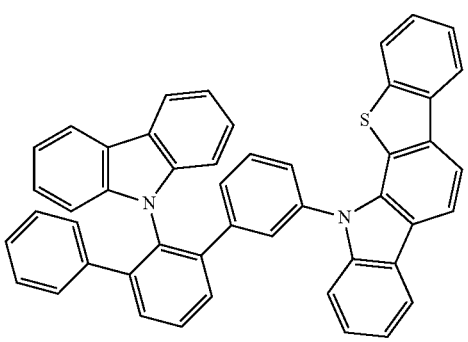

118
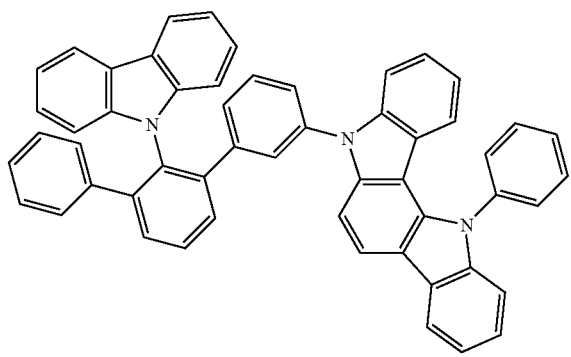
119
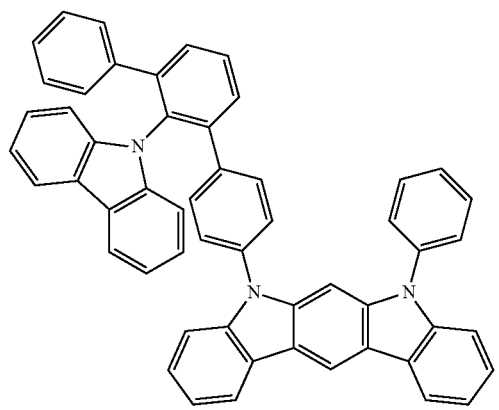
120
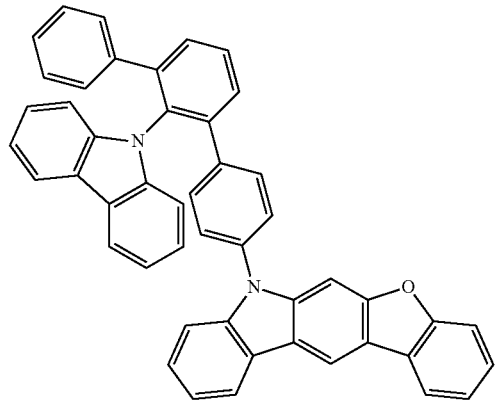
121
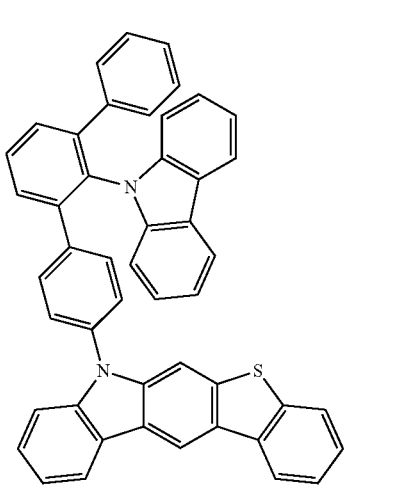
122
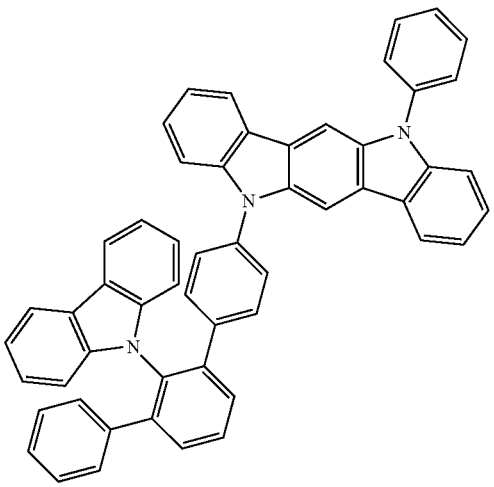
123
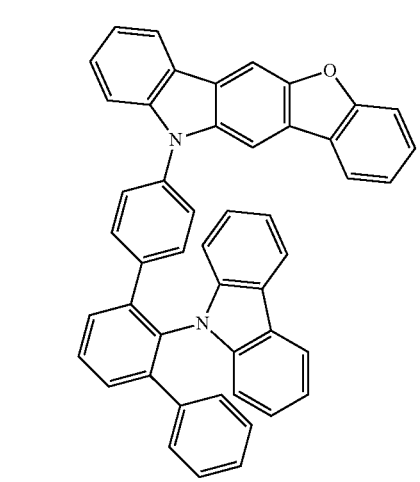
124
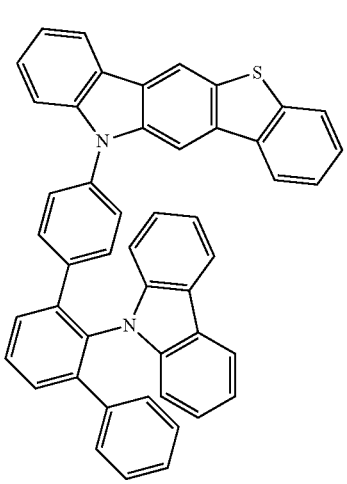

-continued
125
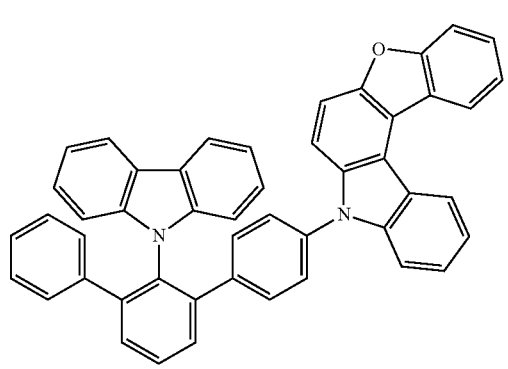
126
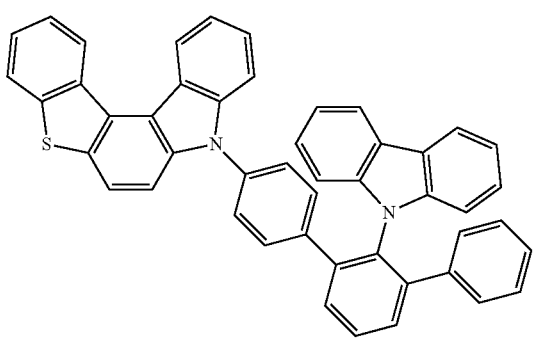
127
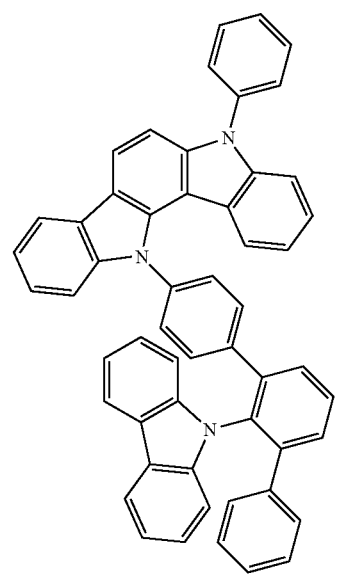
-continued
128
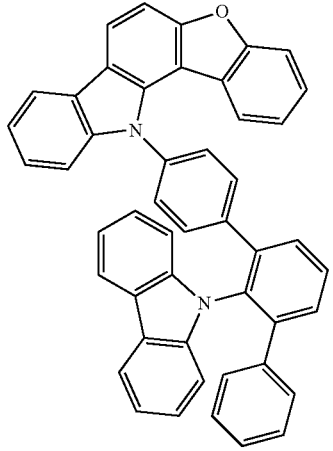
129
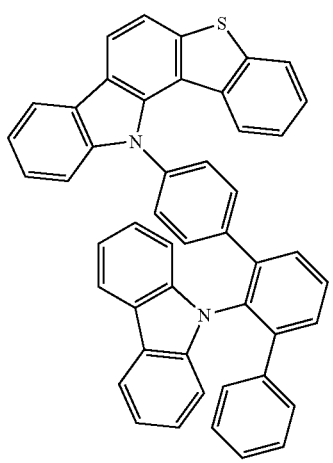
130
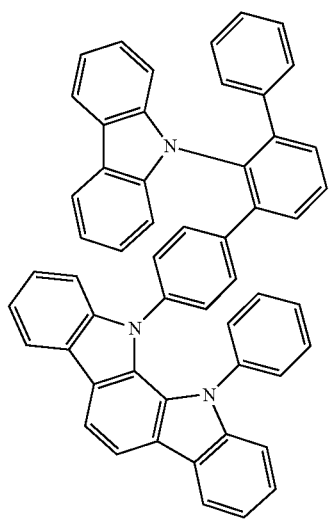

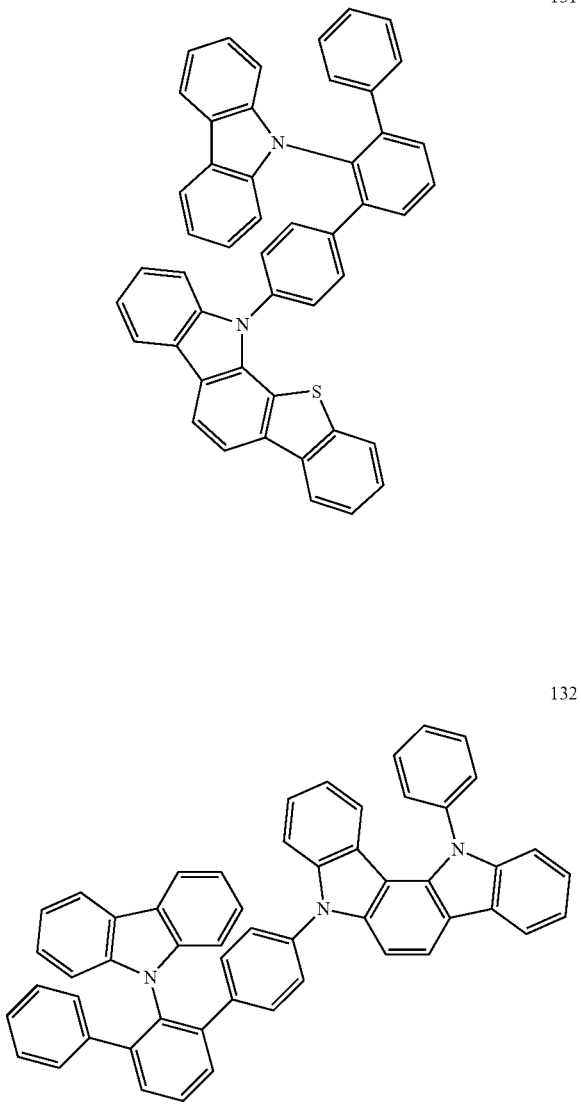

131

132

133

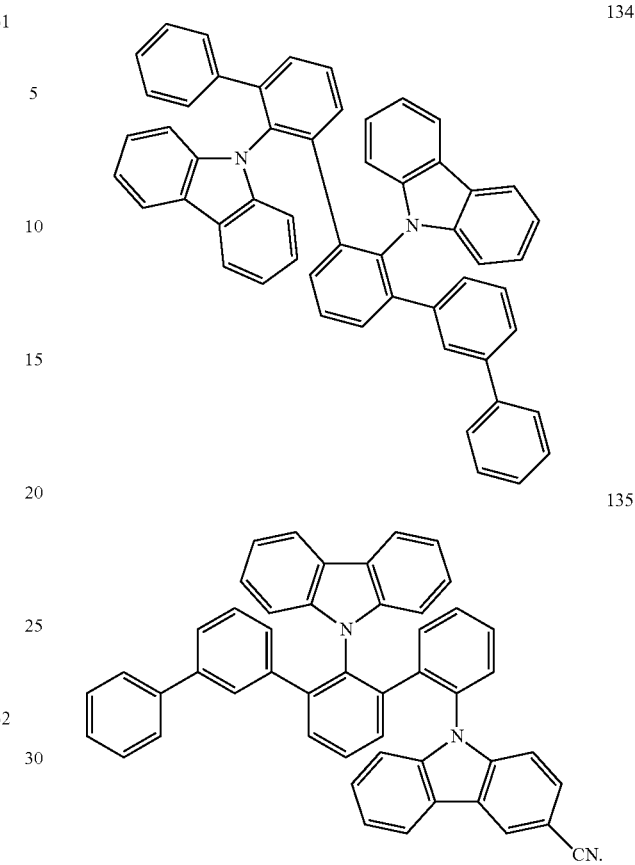

134

135

In Formula 1, "a first benzene ring" and "a second benzene ring" are substituted at two ortho-positions of a phenylene group combined with N of "a carbazole-based ring" (see 'Formula 1' below), thereby providing a steric hindrance on the condensed cyclic compound represented by Formula 1. In this regard, the condensed cyclic compound represented by Formula 1 may have a high triplet state ($T_1$) energy level (for example, 3.10 electron volts (eV) or more) and excellent charge transport characteristics. Therefore, an electronic device, such as an organic light-emitting device, including the condensed cyclic compound by Formula 1 may exhibit high efficiency and high brightness:

Formula 1'

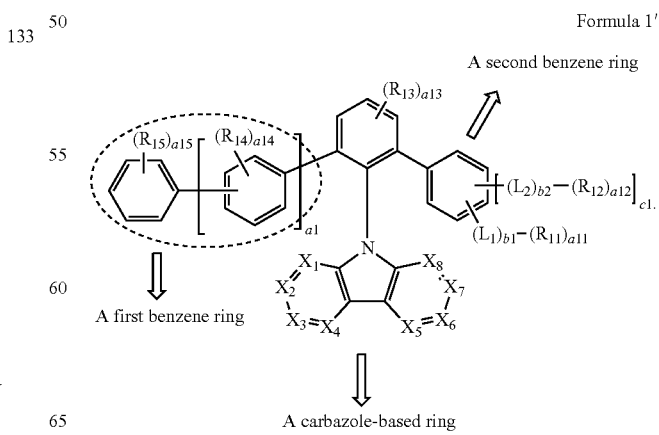

Although not particularly limited to a certain theory, when a $T_1$ energy level of Compound C in which two phenyl groups are bonded to two meta-positions of a phenylene group combined with N of "a carbazole-based ring", is evaluated through simulations using Density Function Theory (DFT) methods of Gaussian programs in which molecular structures are optimized at the B3LYP/6-31G(d,p) levels, it is confirmed that the $T_1$ energy level of Compound C is 3.07 electron volts (eV). It is also confirmed that the $T_1$ energy level of Compound C is lower than that of Compounds of Table 1.

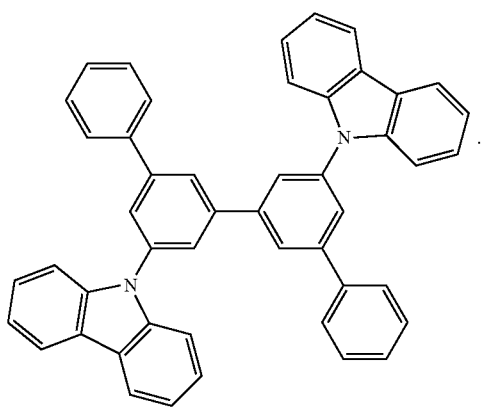

C

In various embodiments, in Formula 1, a11 is not "0", and $R_{11}$ may be selected from carbazole-based groups represented by Formulae 2-1 to 2-5. Accordingly, the condensed cyclic compound represented by Formula 1 may exhibit excellent hole transportability and/or high thermal stability (for example, a high glass transition temperature (Tg)), and thus, an electronic device, such as an organic light-emitting device, including the condensed cyclic compound by Formula 1 may have long lifespan. In various embodiments, in Formula 1, a11 is not "0", and $R_{11}$ may be selected from electron-transporting groups, such as a triazinyl group, defined in the present specification. In this regard, the condensed cyclic compound by Formula 1 may have bipolar characteristics and/or high thermal stability (for example, a high glass transition temperature (Tg)), and accordingly, the condensed cyclic compound represented by Formula 1 may be used as a material for forming an organic light-emitting device, and for example, may be used as a host material in an emission layer.

In various embodiments, in Formula 1, examples of "$R_{14}$ and $R_{15}$" may not include "a substituted or unsubstituted carbazolyl group", and the number of carbazole ring(s) in the condensed cyclic compound represented by Formula 1 may be 0, 1, or 2. In addition, the condensed cyclic compound represented by Formula 1 may have an asymmetrical structure. In this regard, a thin film including the condensed cyclic compound represented by Formula 1 may have excellent thin film morphology and/or excellent thin film surface flatness. Therefore, an electronic device, such as an organic light-emitting device, including the condensed cyclic compound by Formula 1 may exhibit excellent electric characteristics.

For example, the highest occupied molecular orbital (HOMO), the lowest unoccupied molecular orbital (LUMO), the triplet state ($T_1$) energy level, and the singlet state (Si) energy level of Compounds 38, 39, 134, 51, and 135 are evaluated through simulations using DFT methods of Gaussian programs in which molecular structures are optimized at the B3LYP/6-31G(d,p) levels, and the evaluation results are shown in Table 1:

TABLE 1

| Compound No. | HOMO (eV) | LUMO (eV) | $T_1$ (eV) | $S_1$ (eV) |
|---|---|---|---|---|
| 38 | −5.24 | −0.97 | 3.16 | 3.70 |
| 39 | −5.23 | −0.83 | 3.16 | 3.38 |
| 134 | −5.20 | −0.89 | 3.16 | 3.37 |
| 51 | −5.24 | −1.02 | 3.15 | 3.36 |
| 135 | −5.62 | −1.30 | 3.12 | 3.66 |

Referring to Table 1, it was confirmed that Compounds 38, 39, 134, 51, and 135 have high $T_1$ energy levels.

Synthesis methods of the condensed cyclic compound represented by Formula 1 may be understood by those of ordinary skill in the art by referring to Synthesis Examples that will described below.

Therefore, the condensed cyclic compound represented by Formula 1 may be suitable for use in an organic layer of an organic light-emitting device, and for example, may be suitable for use as a material for forming a hole transport layer, a material for forming an electron blocking layer, and/or a host in an emission layer in an organic layer.

According to another aspect of the present inventive concept, an organic light-emitting device includes:
a first electrode;
a second electrode; and
an organic layer disposed between the first electrode and the second electrode,
wherein the organic layer including an emission layer, and
wherein the organic layer includes at least one condensed cyclic compound represented by Formula 1.

The organic light-emitting device includes the organic layer including the condensed cyclic compound represented by Formula 1, thereby exhibiting low driving voltage, high luminescent efficiency, high brightness, high quantum emission efficiency, and long lifespan.

In an embodiment, the emission layer may include the condensed cyclic compound represented by Formula 1.

In various embodiments, the emission layer may include a host and a dopant (wherein an amount of the host is greater than that of the dopant), and the host may include the condensed cyclic compound represented by Formula 1. The condensed cyclic compound represented by Formula 1, which serves as a host, may deliver energy to the dopant according to delayed fluorescence mechanisms. The dopant may include at least one of a fluorescent dopant and a phosphorescent dopant. The dopant may be selected from known dopants in the art. The host may further include any host selected from known hosts in the art.

The emission layer may emit red light, green light, or blue light.

In an embodiment, the emission layer may be a blue emission layer including a phosphorescent dopant, but embodiments are not limited thereto.

In various embodiments, the hole transport region may include the condensed cyclic compound represented by Formula 1.

For example, the organic light-emitting device may include at least one selected from a hole transport layer, an electron transport layer, an electron blocking layer, and a hole blocking layer, and at least one selected from the hole transport layer, the electron transport layer, the electron blocking layer, and the hole blocking layer may include the condensed cyclic compound represented by Formula 1.

In an embodiment, the hole transport region of the organic light-emitting device may include a hole transport layer, and the hole transport layer may include the condensed cyclic compound represented by Formula 1.

In various embodiments, the hole transport region of the organic light-emitting device may include an electron blocking layer, and the electron blocking layer may include the condensed cyclic compound represented by Formula 1. Here, the electron blocking layer may directly contact the emission layer.

The expression that "(an organic layer) includes at least one condensed cyclic compound" as used herein may include a case in which "(an organic layer) includes at least one condensed cyclic compound which is identical to the condensed cyclic compound represented by Formula 1" or a case in which (an organic layer) includes two or more condensed cyclic compounds which are different from the condensed cyclic compound represented by Formula 1".

For example, the organic layer may include, as the condensed cyclic compound represented by Formula 1, only Compound 1. Here, Compound 1 may be in the emission layer of the organic light-emitting device. In various embodiments, the organic layer may include, as the condensed cyclic compound represented by Formula 1, Compound 1 and Compound 2. Here, Compound 1 and Compound 2 may be included in the identical layer (for example, Compound 1 and Compound 2 may both be in the emission layer), or may be included in different layers (for example, Compound 1 may be in the emission layer and Compound 2 may be in the electron blocking layer).

The first electrode may be an anode, which is a hole injection electrode, and the second electrode may be a cathode, which is an electron injection electrode. In various embodiments, the first electrode may be a cathode, which is an electron injection electrode, and the second electrode may be an anode, which is a hole injection electrode.

For example, in the organic light-emitting device,
the first electrode may be an anode,
the second electrode may be a cathode, and
the organic layer may include a hole transport region that is disposed between the first electrode and the emission layer and an electron transport region that is disposed between the emission layer and the second electrode,
wherein the hole transport region includes a hole injection layer, a hole transport layer, an electron blocking layer, or any combination thereof, and
wherein the electron transport region includes a hole blocking layer, an electron transport layer, an electron injection layer, or a combination thereof.

The term "organic layer" as used herein may refer to a single layer and/or a plurality of layers disposed between the first electrode and the second electrode of the organic light-emitting device. The "organic layer" may include not only an organic compound, but also a metal-containing organometallic complex.

FIG. 1 is a schematic cross-sectional view of an organic light-emitting device 10 according to an embodiment. Hereinafter, the structure of an organic light-emitting device according to an embodiment and a method of manufacturing an organic light-emitting device, according to an embodiment, will be described in connection with FIG. 1. The organic light-emitting device 10 includes a first electrode 11, an organic layer 15, and a second electrode 19, which are sequentially stacked in this stated order.

A substrate may be additionally disposed under the first electrode 11 or above the second electrode 19. For use as the substrate, any substrate that is used in general organic light-emitting devices may be used, and the substrate may be a glass substrate or a transparent plastic substrate, each having excellent mechanical strength, thermal stability, transparency, surface smoothness, ease of handling, and water-resistance.

The first electrode 11 may be, for example, formed by depositing or sputtering a material for forming the first electrode 11 on the substrate. The first electrode 11 may be an anode. The material for forming the first electrode 11 may be selected from materials with a high work function to facilitate hole injection. The first electrode 11 may be a reflective electrode, a semi-transmissive electrode, or a transmissive electrode. The material for forming the first electrode 11 may be indium tin oxide (ITO), indium zinc oxide (IZO), tin oxide ($SnO_2$), and zinc oxide (ZnO). In various embodiments, metals, such as magnesium (Mg), aluminum (Al), aluminum-lithium (Al—Li), calcium (Ca), magnesium-indium (Mg—In), and magnesium-silver (Mg—Ag), may be used as the material for forming the first electrode 11.

The first electrode 11 may have a single-layered structure or a multi-layered structure including two or more layers. For example, the first electrode 11 may have a three-layered structure of ITO/Ag/ITO, but the structure of the first electrode 11 is not limited thereto.

The organic layer 15 may be disposed on the first electrode 11.

The organic layer 15 may include a hole transport region, an emission layer; and an electron transport region.

The hole transport region may be disposed between the first electrode 11 and the emission layer.

The hole transport region may include at least one selected from a hole injection layer, a hole transport layer, an electron blocking layer, and a buffer layer.

The hole transport region may include only either a hole injection layer or a hole transport layer. In various embodiments, the hole transport region may have a structure of hole injection layer/hole transport layer, a structure of hole injection layer/hole transport layer/electron blocking layer, or a structure of hole transport layer/electron blocking layer, wherein the layers of each structure are sequentially stacked from the first electrode 11 in the stated order.

When hole transport region includes a hole injection layer, the hole injection layer may be formed on the first electrode 11 by using one or more suitable methods selected from vacuum deposition, spin coating, casting, and Langmuir-Blodgett (LB) deposition.

When the hole injection layer is formed using vacuum deposition, the deposition conditions may vary according to a material that is used to form the hole injection layer to be deposited, and the structure and thermal characteristics of the hole injection layer to be formed. For example, the deposition conditions may include a deposition temperature of about 100° C. to about 500° C., a vacuum pressure of about $10^{-8}$ torr to about $10^{-3}$ torr, and a deposition rate of about 0.01 Angstroms per second (Å/sec) to about 100 Å/sec, but the deposition conditions are not limited thereto.

When the hole injection layer is formed using spin coating, the coating conditions may vary according a material that is used to form the hole injection layer to be deposited, and the structure and thermal characteristics of the hole injection layer to be formed. For example, a coating speed may be from about 2,000 revolutions per minute (rpm) to about 5,000 rpm and a temperature at which a heat treatment is performed to remove a solvent after coating may be from about 80° C. to about 200° C., but the coating conditions are not limited thereto.

Conditions for forming a hole transport layer and an electron blocking layer may be understood by referring to conditions for forming the hole injection layer.

The hole transport region may include, for example, at least one selected from m-MTDATA, TDATA, 2-TNATA, NPB, β-NPB, TPD, Spiro-TPD, Spiro-NPB, methylated-NPB, TAPC, HMTPD, 4,4',4"-tris(N-carbazolyl)triphenylamine (TCTA), polyaniline/dodecylbenzene sulfonic acid (PANI/DBSA), poly(3,4-ethylenedioxythiophene)/poly (4-styrene sulfonate) (PEDOT/PSS), polyaniline/camphor sulfonic acid (PANI/CSA), polyaniline/poly(4-styrene sulfonate) (PANI/PSS), a compound represented by Formula 201, and a compound represented by Formula 202:

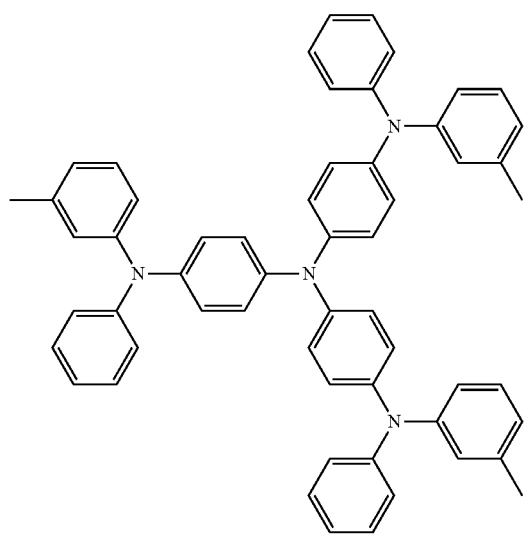

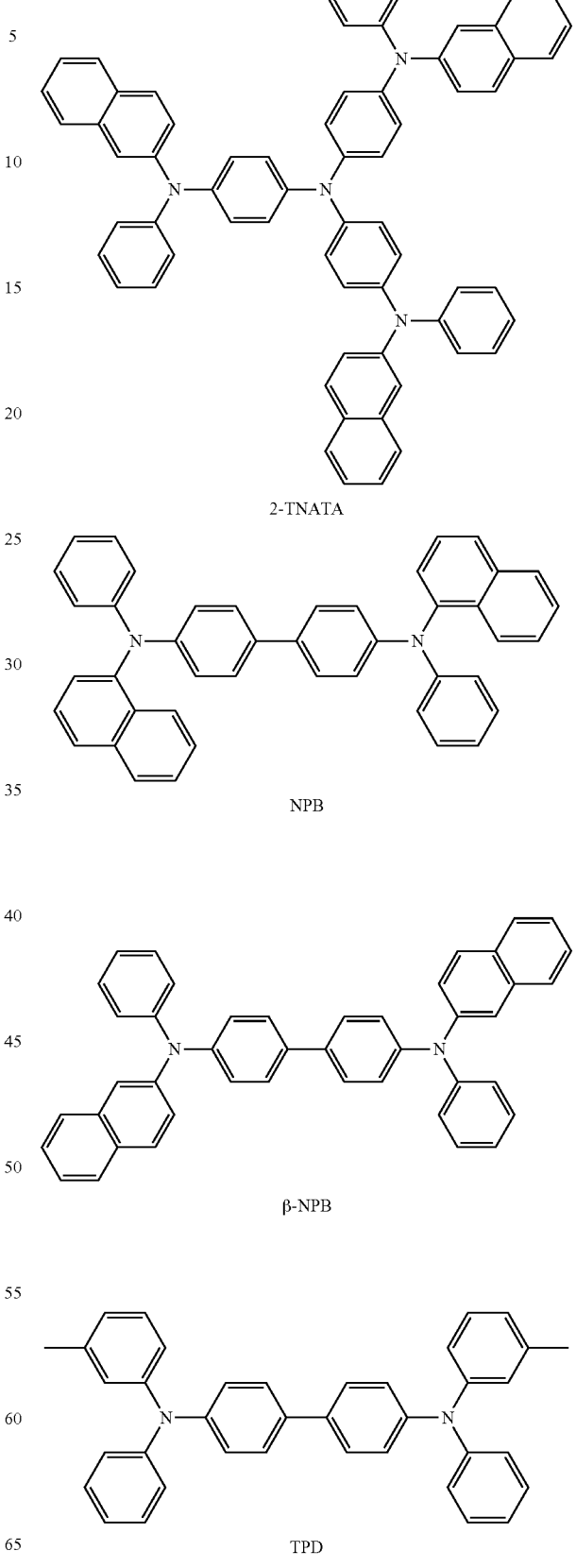

-continued

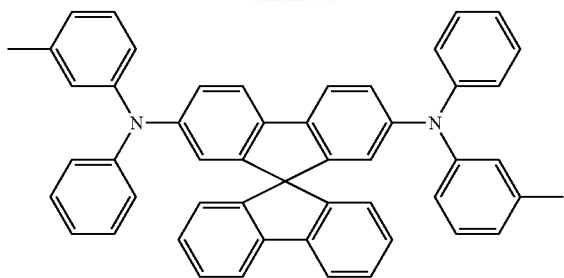
Spiro-TPD

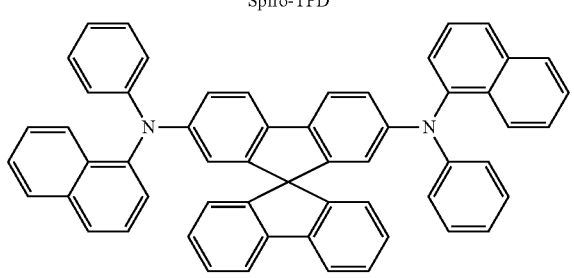
Spiro-NPB

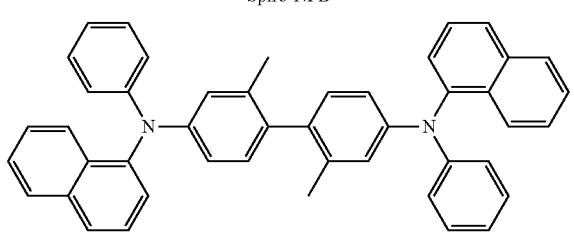
methylated NPB

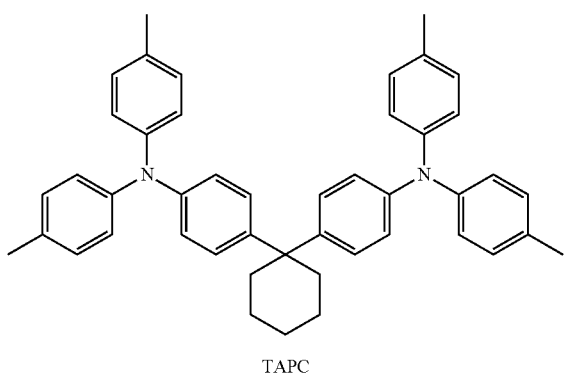
TAPC

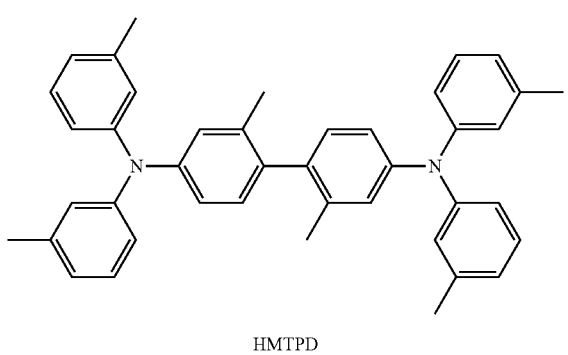
HMTPD

-continued

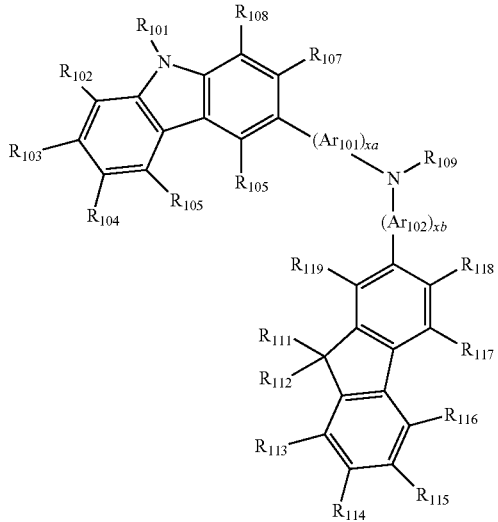
Formula 201

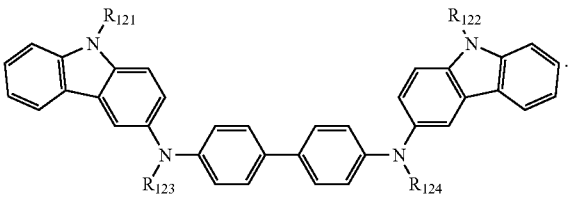
Formula 202

In Formula 201, $Ar_{101}$ and $Ar_{102}$ may each independently be selected from:

a phenylene group, a pentalenylene group, an indenylene group, a naphthylene group, an azulenylene group, a heptalenylene group, an acenaphthylene group, a fluorenylene group, a phenalenylene group, a phenanthrenylene group, an anthracenylene group, a fluoranthenylene group, a triphenylenylene group, a pyrenylene group, a chrysenylenylene group, a naphthacenylene group, a picenylene group, a perylenylene group, and a pentacenylene group; and a phenylene group, a pentalenylene group, an indenylene group, a naphthylene group, an azulenylene group, a heptalenylene group, an acenaphthylene group, a fluorenylene group, a phenalenylene group, a phenanthrenylene group, an anthracenylene group, a fluoranthenylene group, a triphenylenylene group, a pyrenylene group, a chrysenylenylene group, a naphthacenylene group, a picenylene group, a perylenylene group, and a pentacenylene group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_{60}$ alkoxy group, a $C_3$-$C_{10}$ cycloalkyl group, a $C_3$-$C_{10}$ cycloalkenyl group, a $C_1$-$C_{10}$ heterocycloalkyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group.

In Formula 201, xa and xb may each independently be an integer selected from 0 to 5, or for example, may be 0, 1, or 2. For example, in Formula 201, xa may be 1, and xb may be 0, but embodiments are not limited thereto.

In Formulae 201 and 202, $R_{101}$ to $R_{108}$, $R_{111}$ to $R_{119}$, and $R_{121}$ to $R_{124}$ may each independently be selected from:

hydrogen, deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{10}$ alkyl group (for example, a methyl group, an ethyl group, a propyl group, a butyl group, a pentyl group, and a hexyl group), and a $C_1$-$C_{10}$ alkoxy group (for example, a methoxy group, an ethoxy group, a propoxy group, butoxy group, and a pentoxy group);

a $C_1$-$C_{10}$ alkyl group and a $C_1$-$C_{10}$ alkoxy group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, and a phosphoric acid group or a salt thereof;

a phenyl group, a naphthyl group, an anthracenyl group, a fluorenyl group, and a pyrenyl group; and a phenyl group, a naphthyl group, an anthracenyl group, a fluorenyl group, and a pyrenyl group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{10}$ alkyl group, and a $C_1$-$C_{10}$ alkoxy group, but embodiments are not limited thereto.

In Formula 201, 8109 may be selected from:

a phenyl group, a naphthyl group, an anthracenyl group, and a pyridinyl group; and a phenyl group, a naphthyl group, an anthracenyl group, and a pyridinyl group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a naphthyl group, an anthracenyl group, and a pyridinyl group.

In an embodiment, the compound represented by Formula 201 may be represented by Formula 201A, but embodiments are not limited thereto:

Formula 201A

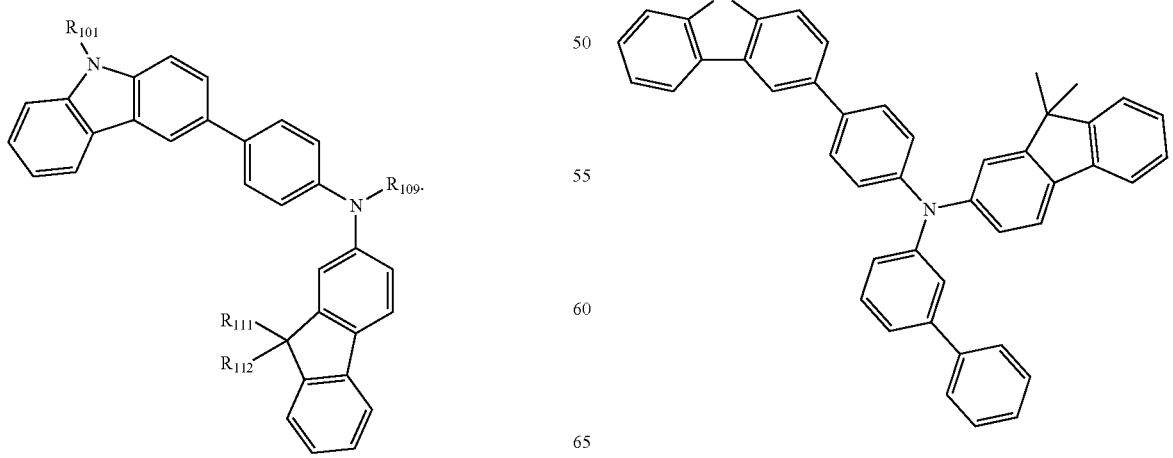

In Formula 201A, $R_{101}$, $R_{111}$, $R_{112}$, and $R_{109}$ may each independently be the same as described elsewhere herein in connection with those provided in the present specification.

For example, the compound represented by Formula 201 and the compound represented by Formula 202 may each independently include any of Compounds HT1 to HT20, but embodiments are not limited thereto:

HT1

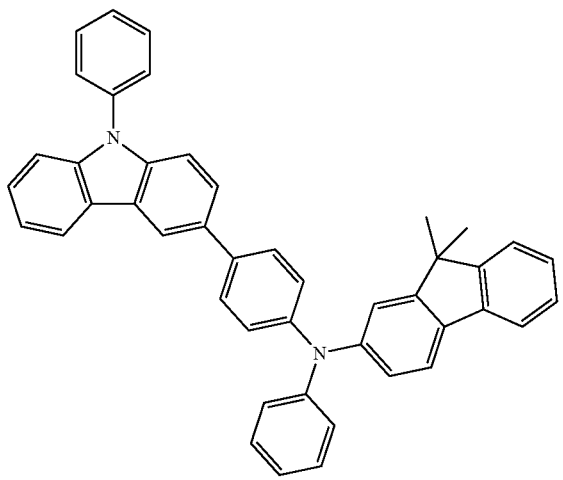

HT2

HT3
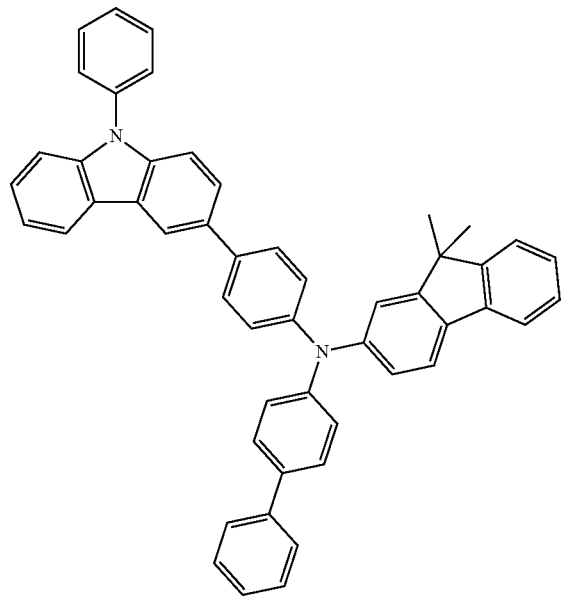
HT4
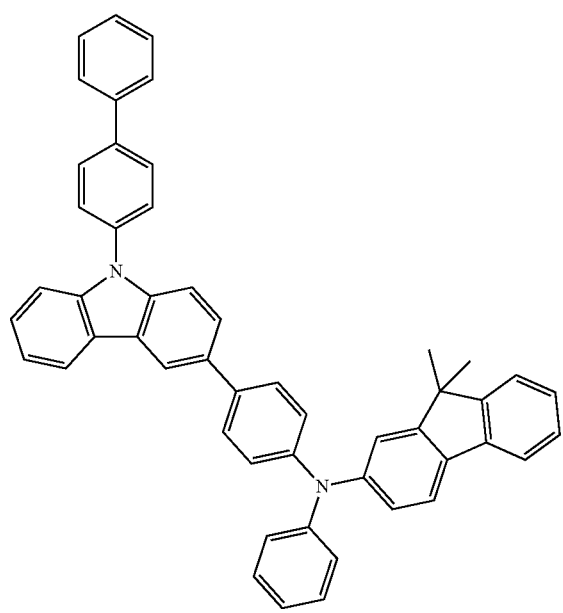
HT5
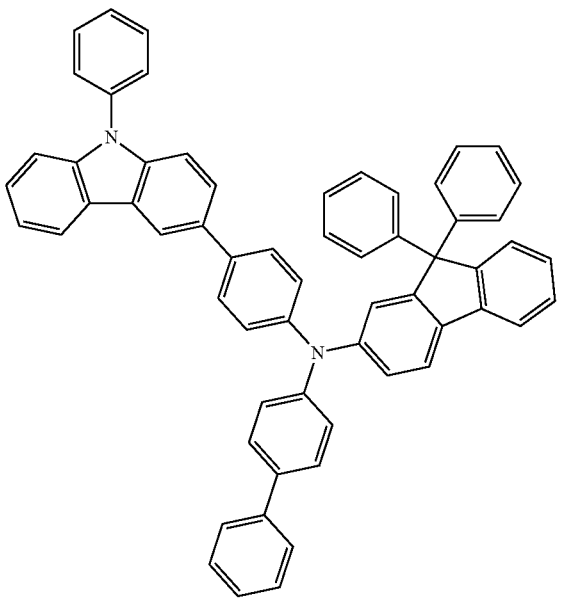
HT6
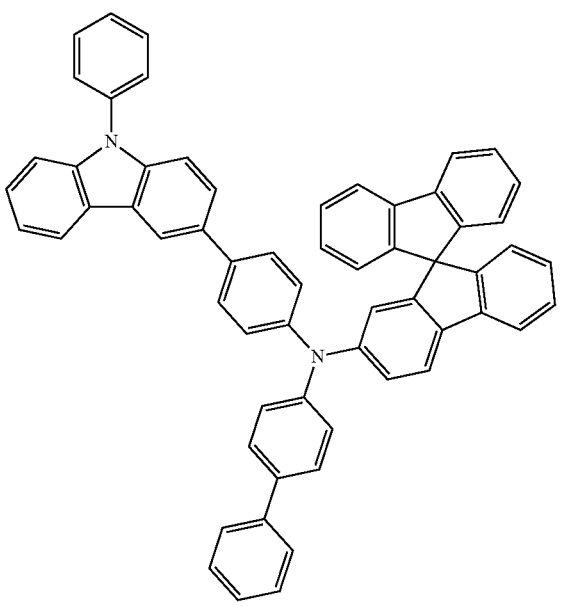

HT7
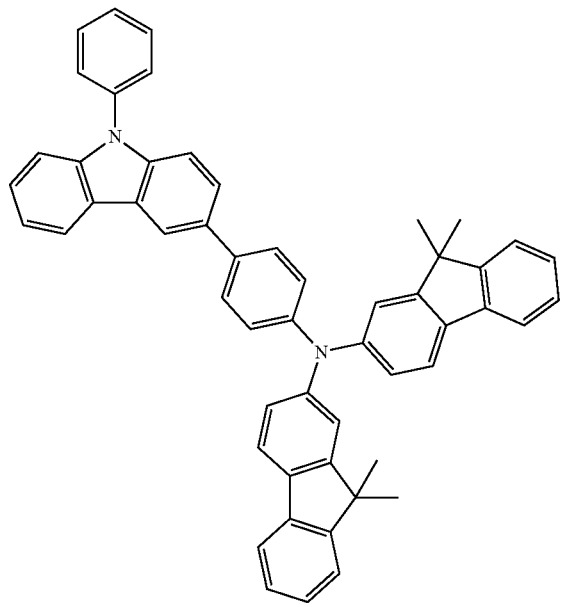
HT9
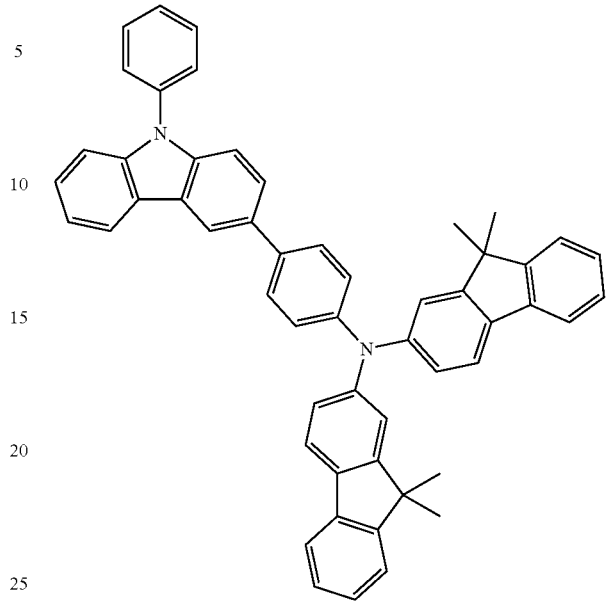
HT8
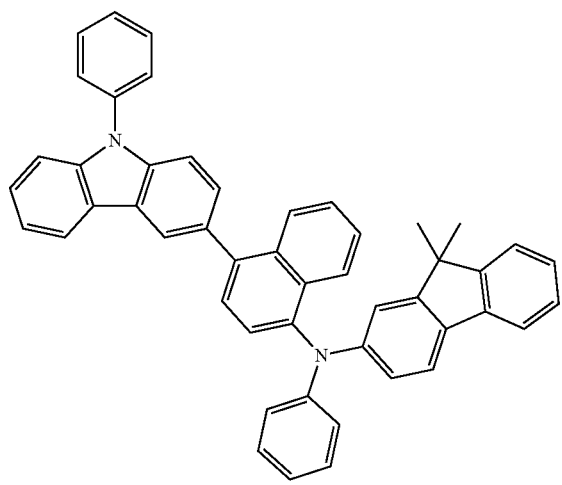
HT10
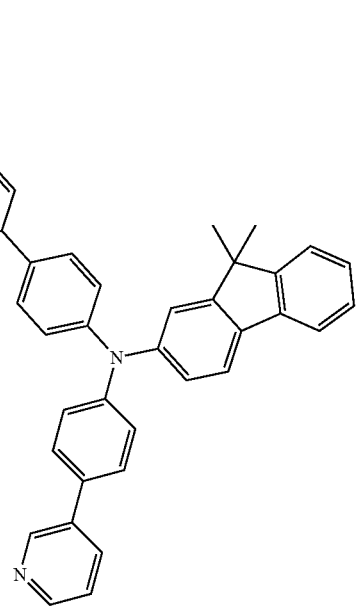

HT11
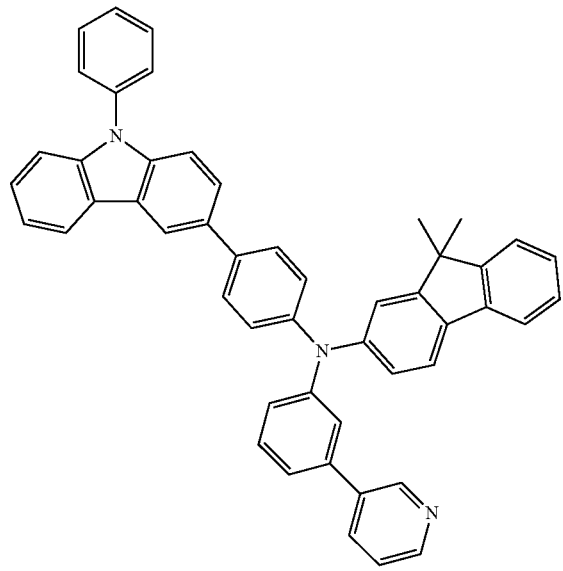
HT12
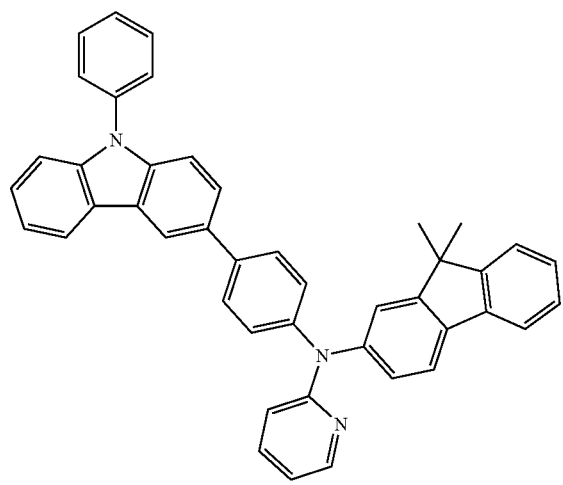
HT13
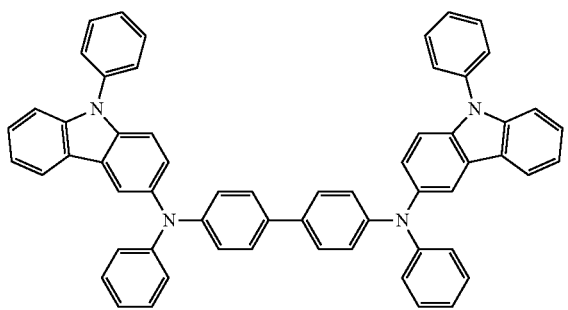
HT14
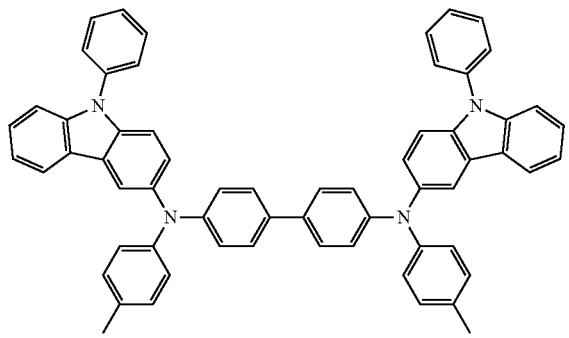
HT15
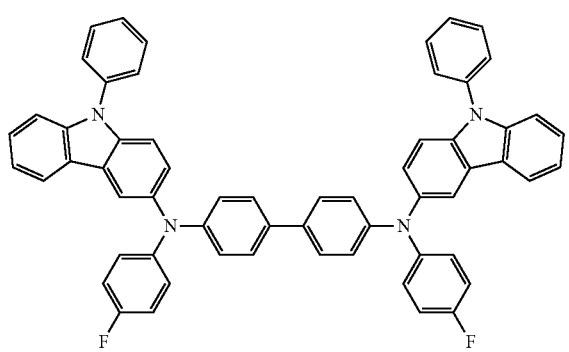
HT16
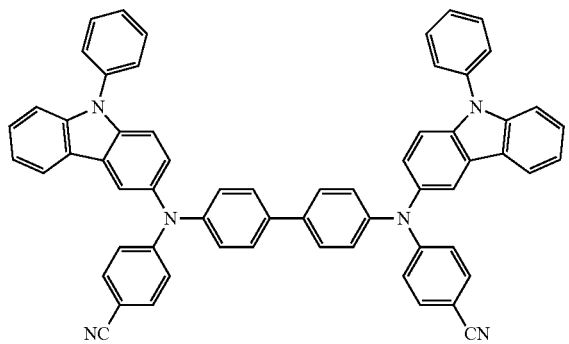
HT17
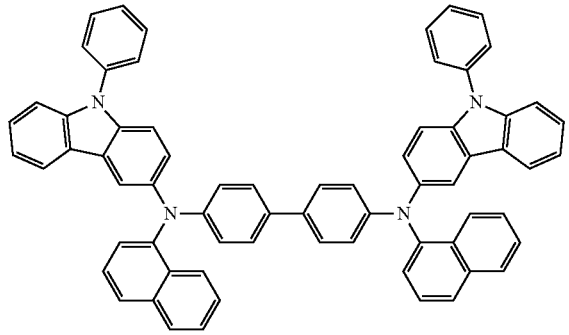

-continued

HT18
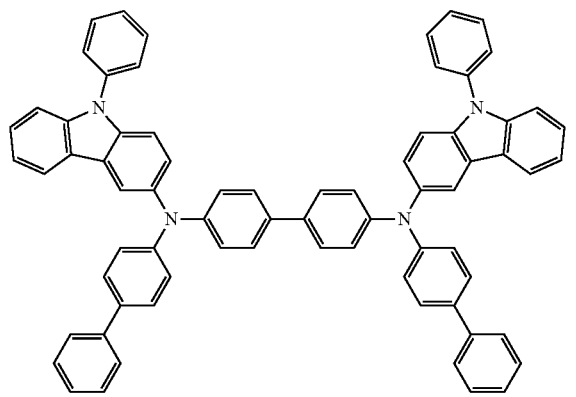

HT19
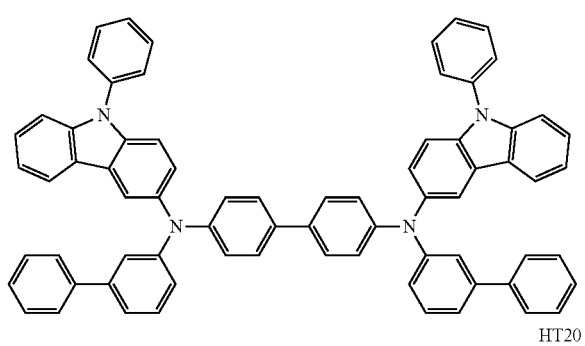

HT20
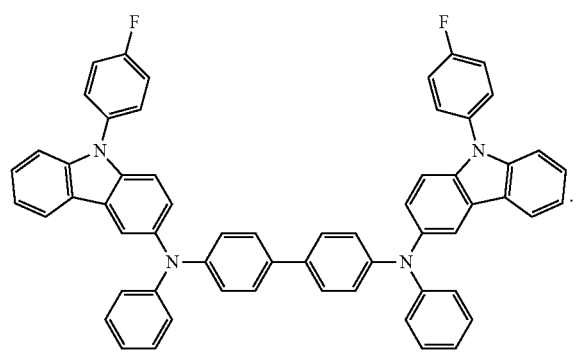

In various embodiments, the hole transport layer may include the condensed cyclic compound represented by Formula 1.

A thickness of the hole transport region may be in a range of about 100 Angstroms (Å) to about 10,000 Å, for example, about 100 Å to about 1,000 Å. When the hole transport region includes at least one of a hole injection layer and a hole transport layer, a thickness of the hole injection layer may be in a range of about 100 Å to about 10,000 Å, for example, about 100 Å to about 1,000 Å, and a thickness of the hole transport layer may be in a range of about 50 Å to about 2,000 Å, for example, about 100 Å to about 1,500 Å. While not wishing to be bound by theory, it is understood that when the thicknesses of the hole transport region, the hole injection layer, and the hole transport layer are within these ranges, satisfactory hole transporting characteristics may be obtained without a substantial increase in driving voltage.

The hole transport region may further include, in addition to these materials, a charge-generation material for improving conductive properties. The charge-generation material may be homogeneously or non-homogeneously dispersed in the hole transport region.

The charge-generation material may be, for example, a p-dopant. The p-dopant may be one selected from a quinone derivative, a metal oxide, and a cyano group-containing compound, but embodiments are not limited thereto. Non-limiting examples of the p-dopant are a quinone derivative, such as tetracyanoquinonedimethane (TCNQ) and 2,3,5,6-tetrafluoro-tetracyano-1,4-benzoquinonedimethane (F4-TCNQ); a metal oxide, such as a tungsten oxide and a molybdenum oxide; and a cyano group-containing compound, such as Compounds HT-D1 and HP-1, but embodiments are not limited thereto:

Compound HT-D1
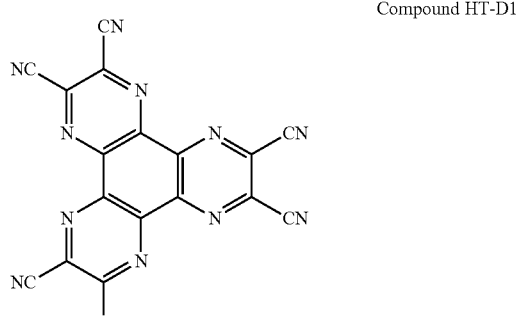

F4-TCNQ
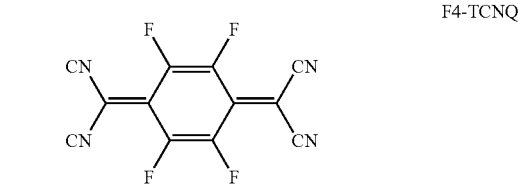

Compound HP-1
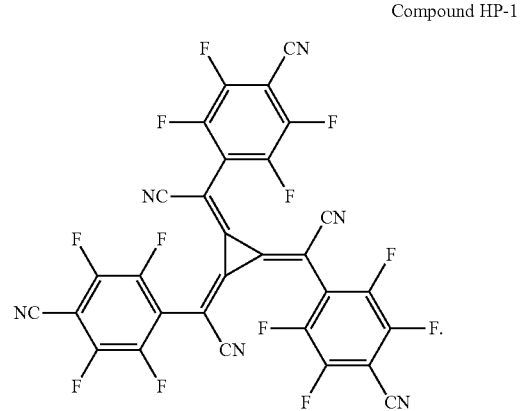

The hole transport region may further include a buffer layer.

The buffer layer may compensate for an optical resonance distance according to a wavelength of light emitted from the emission layer, and thus, the efficiency of a formed organic light-emitting device may be improved.

The emission layer may be formed on the hole transport region by using one or more suitable methods selected from vacuum deposition, spin coating, casting, and LB deposition. When the emission layer is formed using vacuum deposition and spin coating, the deposition and coating conditions for the emission layer may be similar with those for forming the hole injection layer, although deposition and coating conditions may vary according to a material that is used to form the emission layer.

The hole transport region may further include an electron blocking layer. The electron blocking layer may include a known compound, such as mCP, but embodiments are not limited thereto:

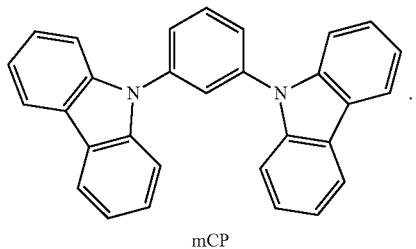 [SMILES: c1cc(-n2c3ccccc3c3ccccc32)cc(-n2c3ccccc3c3ccccc32)c1]

mCP

In various embodiments, the hole transport region may include an electron blocking layer, and the electron blocking layer may include the condensed cyclic compound represented by Formula 1.

A thickness of the electron blocking layer may be in a range of about 50 Å to about 1,000 Å, for example, about 70 Å to about 500 Å. While not wishing to be bound by theory, it is understood that when the thickness of the electron blocking layer is within these ranges, satisfactory electron blocking characteristics may be obtained without a substantial increase in driving voltage.

When the organic light-emitting device 10 is a full color organic light-emitting device, the emission layer may be patterned into a red emission layer, a green emission layer, and a blue emission layer. In various embodiments, the emission layer may have a stacked structure including a red emission layer, a green emission layer and/or a blue emission layer, thereby emitting light.

The emission layer may include the condensed cyclic compound represented by Formula 1. For example, the emission layer may only include the condensed cyclic compound represented by Formula 1. In various embodiments, the emission layer may include a host and a dopant, wherein the host may include the condensed cyclic compound represented by Formula 1.

In an embodiment, a dopant in the emission layer may be a phosphorescent dopant, and the phosphorescent dopant may include an organometallic compound represented by Formula 81:

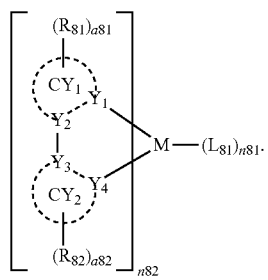

Formula 81

In Formula 81,

M may be selected from iridium (Ir), platinum (Pt), osmium (Os), titanium (Ti), zirconium (Zr), hafnium (Hf), europium (Eu), terbium (Tb), and thulium (Tm), $Y_1$ to $Y_4$ may each independently be C or N, $Y_1$ and $Y_2$ may be linked via a single bond or a double bond, and $Y_3$ and $Y_4$ may be linked via a single bond or a double bond, $CY_1$ and $CY_2$ may each independently be selected from a benzene group, a naphthalene group, a fluorene group, a spiro-fluorene group, an indene group, a pyrrole group, a thiophene group, a furan group, an imidazole group, a pyrazole group, a thiazole group, an isothiazole group, an oxazole group, an isoxazole group, a pyridine group, a pyrazine group, a pyrimidine group, a pyridazine group, a quinoline group, an isoquinoline group, a benzoquinoline group, a quinoxaline group, a quinazoline group, a carbazole group, a benzimidazole group, a benzofuran group, a benzothiophene group, an isobenzothiophene group, a benzoxazole group, an isobenzoxazole group, a triazole group, a tetrazole group, an oxadiazole group, a triazine group, a dibenzofuran group, or a dibenzothiophene group, wherein $CY_1$ and $CY_2$ may be optionally linked to each other via a single bone or an organic linking group, $R_{81}$ and $R_{82}$ may each independently be selected from hydrogen, deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, —SF$_5$, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, a substituted or unsubstituted monovalent non-aromatic condensed heteropolycyclic group, —N(Q$_1$)(Q$_2$), —Si(Q$_3$)(Q$_4$)(Q$_5$), and —B(C)$_6$)(Q$_7$), a81 and a82 may each independently be an integer selected from 1 to 5, n81 may be an integer selected from 0 to 4, n82 may be 1, 2, or 3, and L$_{81}$ may be a monovalent organic ligand, a divalent organic ligand, or a trivalent organic ligand.

$R_{81}$ and $R_{82}$ may each independently be the same as described herein in connection with $R_{11}$.

The phosphorescent dopant may include at least one selected from Compounds PD1 to PD79 and FIr$_6$, but embodiments are not limited thereto:

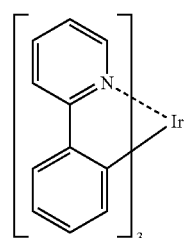

PD1

PD2 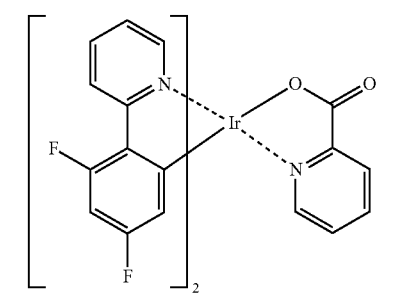
PD3 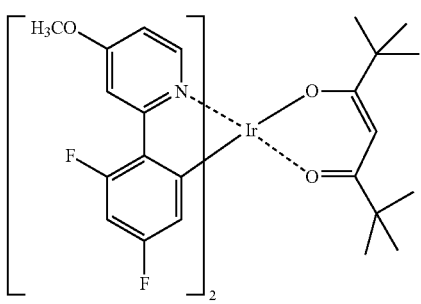
PD4 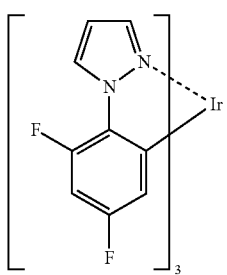
PD5 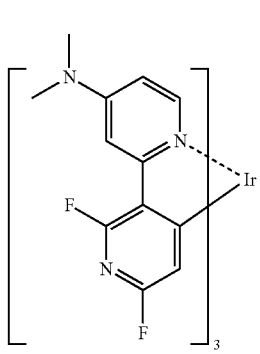
PD6 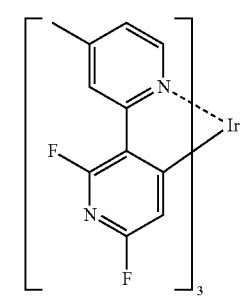
PD7 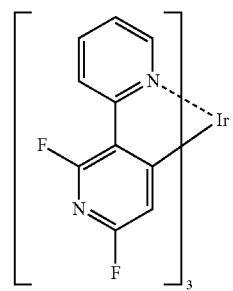
PD8 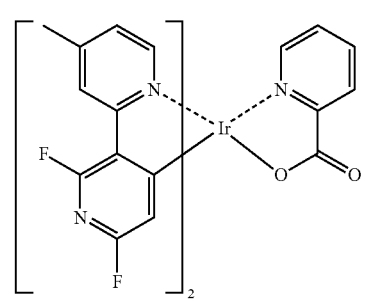
PD9 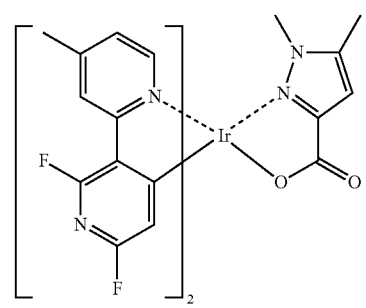
PD10 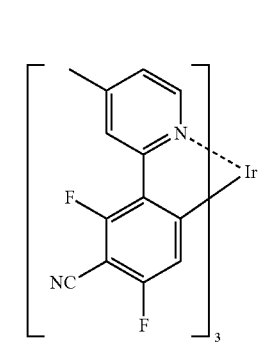
PD11 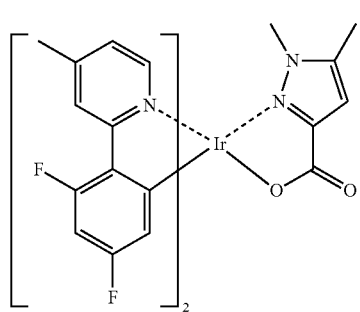

-continued
PD12
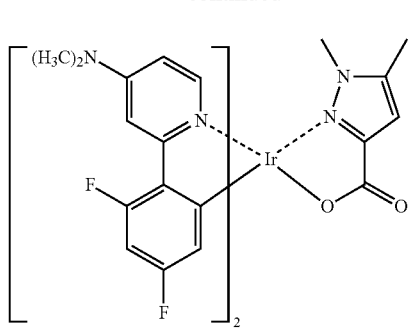
PD13
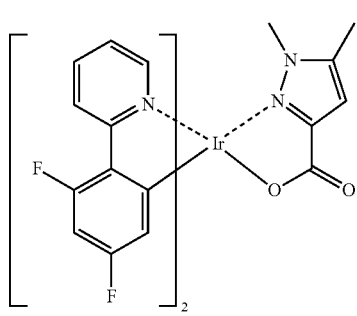
PD14
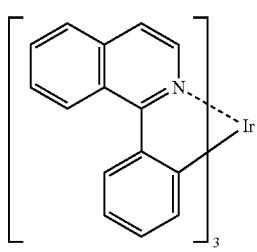
PD15
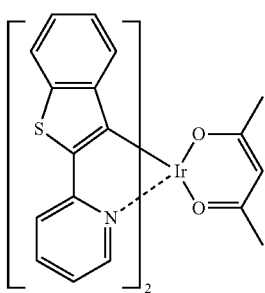
PD16
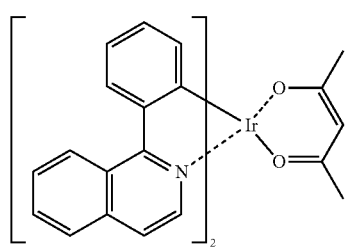
PD17
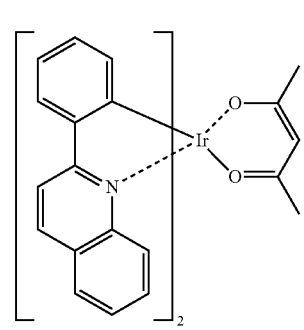
PD18
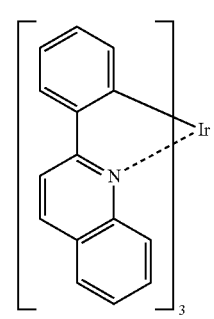
PD19
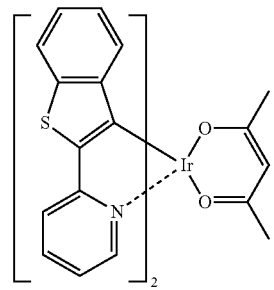
PD20
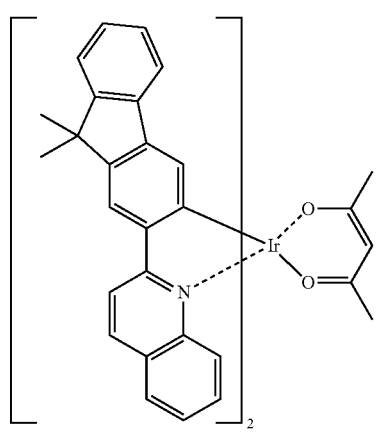

-continued
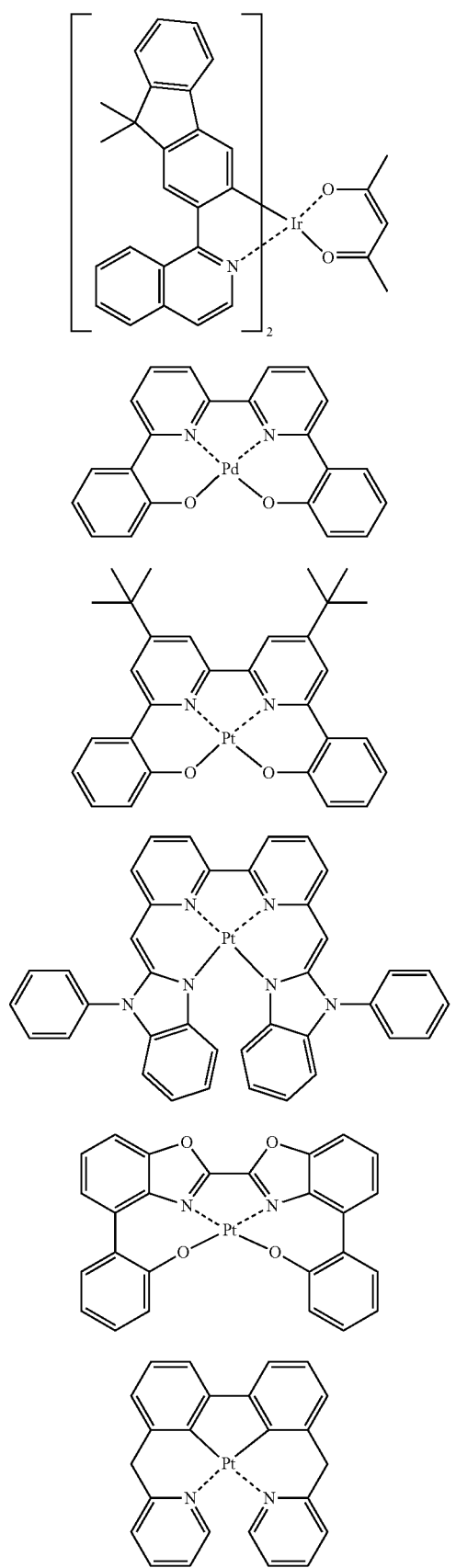
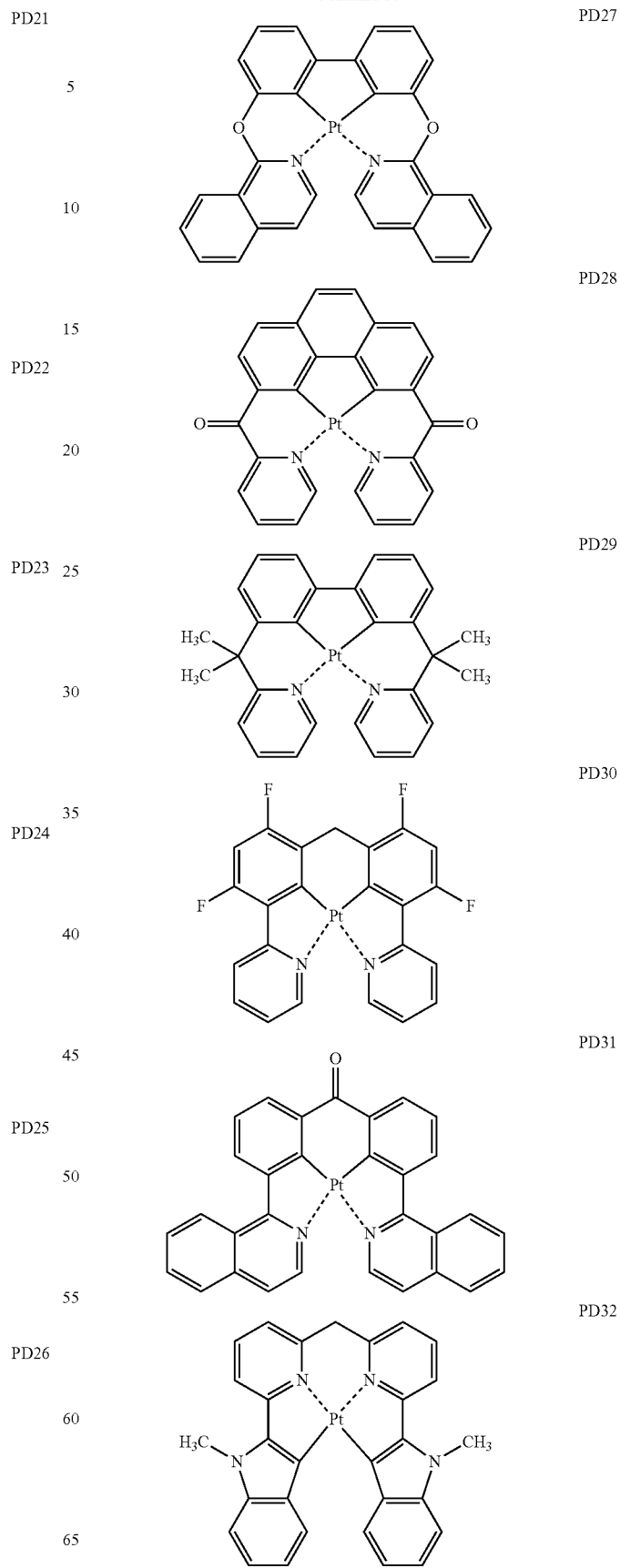

PD33 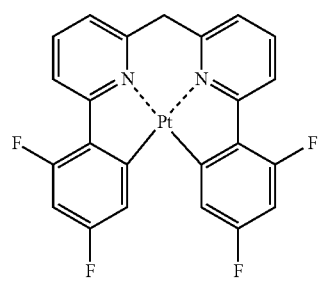
PD34 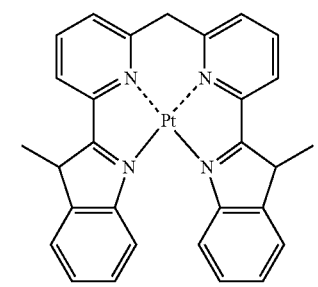
PD35 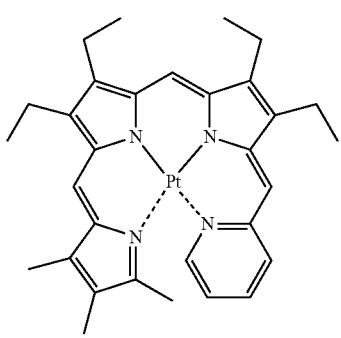
PD36 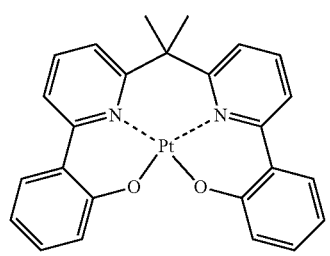
PD37 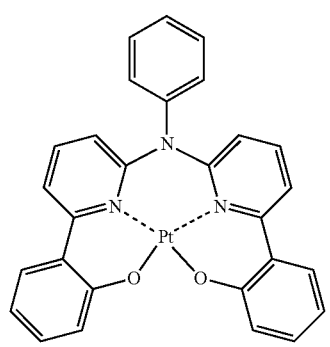
PD38 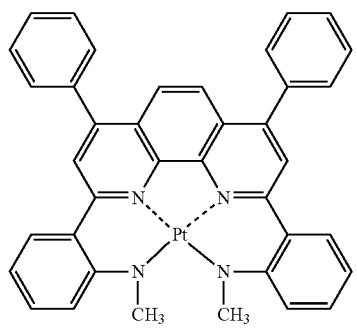
PD39 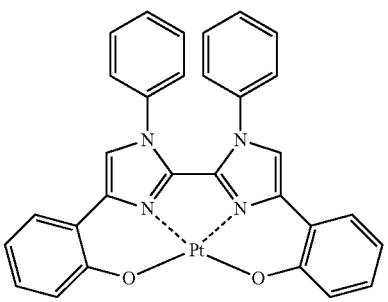
PD40 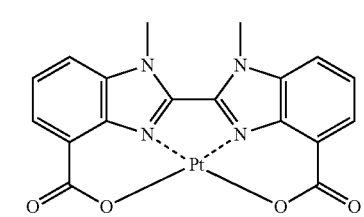
PD41 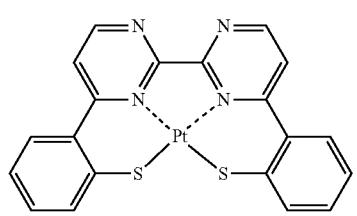
PD42 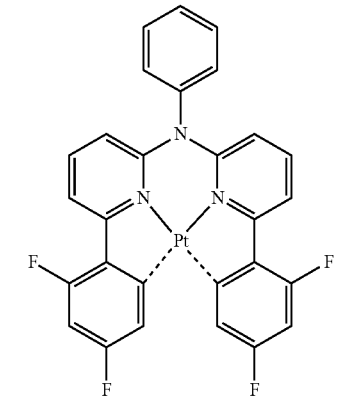

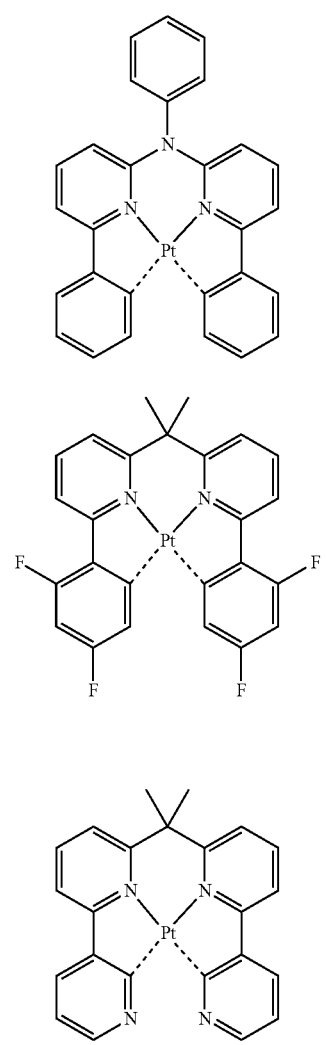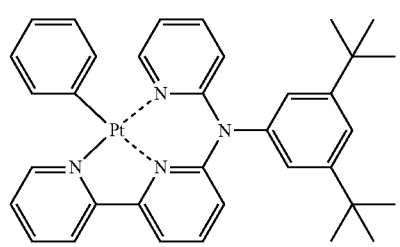

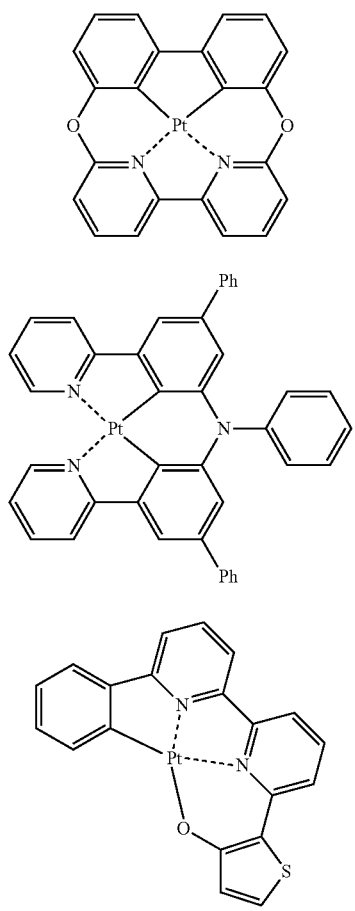
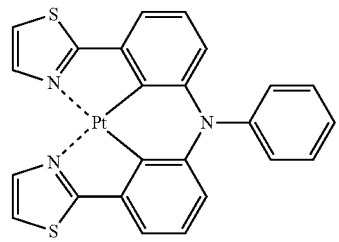
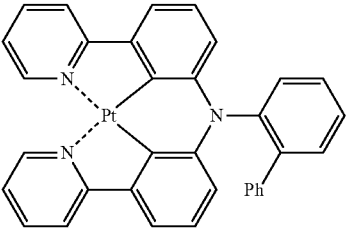
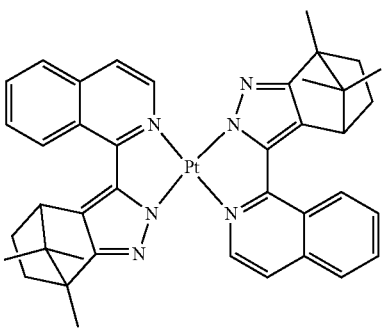
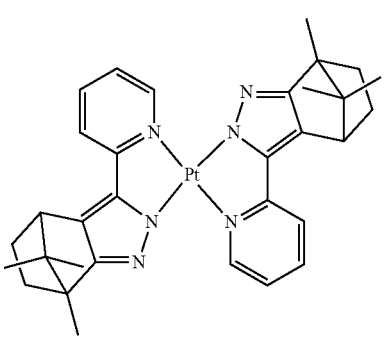
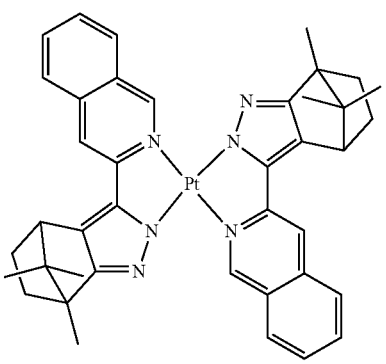

-continued
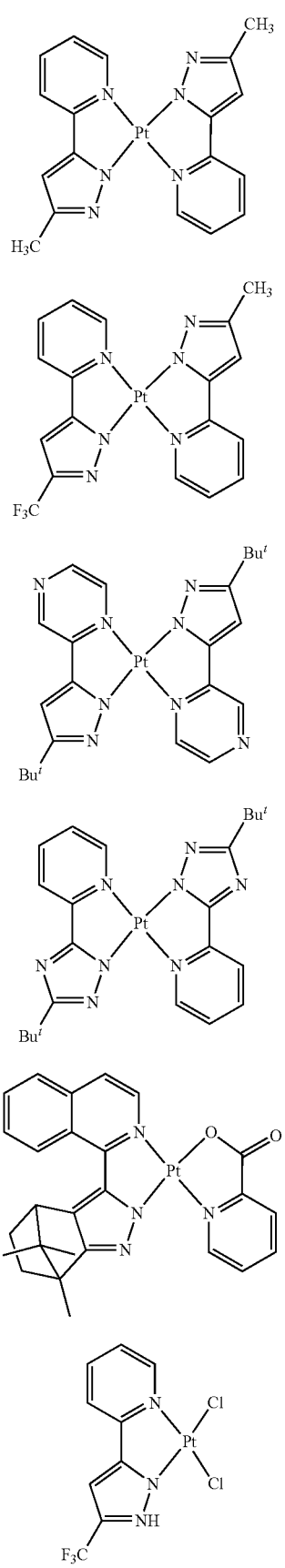
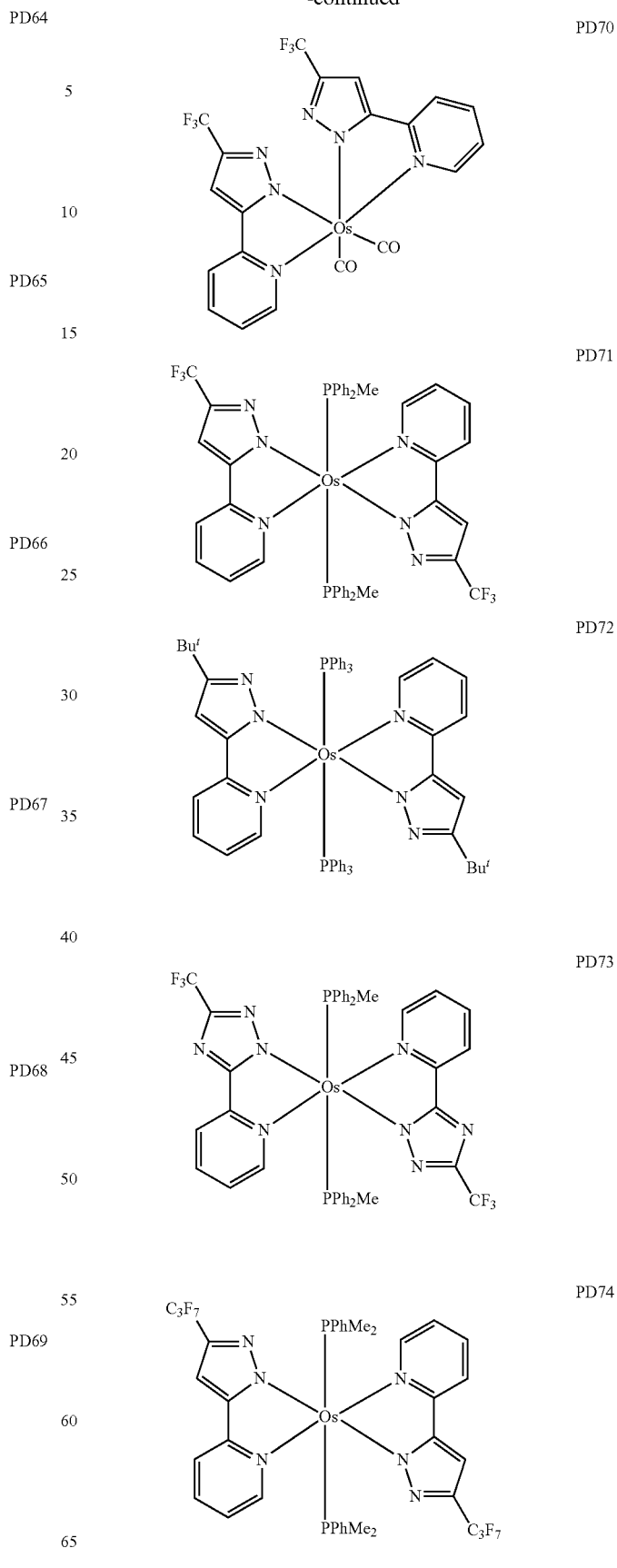

-continued

PD75
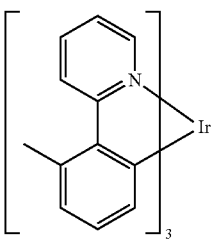

PD76
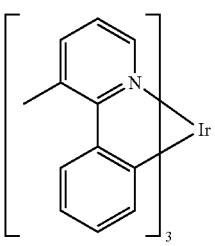

PD77
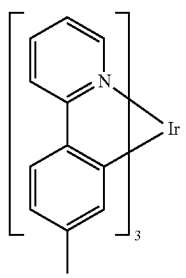

PD78
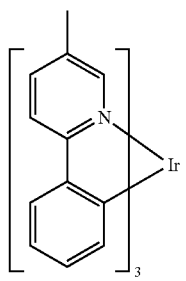

PD79
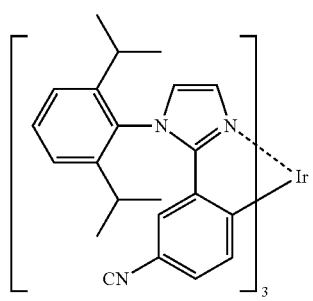

-continued

Flr6
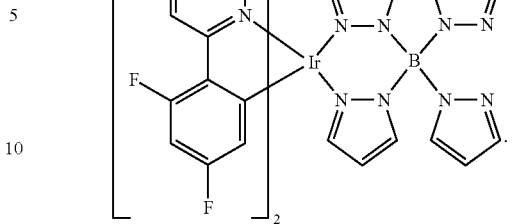

In various embodiments, the phosphorescent dopant may include PtOEP:

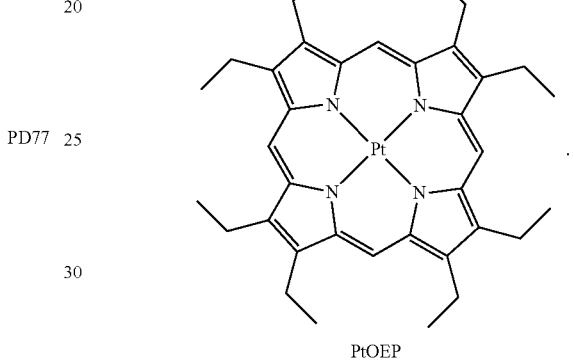

PtOEP

When the emission layer includes a host and a dopant, an amount of the dopant may be generally in a range of about 0.01 to about 20 parts by weight based on 100 parts by weight, but embodiments are not limited thereto.

A thickness of the emission layer may be in a range of about 100 Å to about 1,000 Å, for example, about 200 Å to about 600 Å. While not wishing to be bound by theory, it is understood that when the thickness of the emission layer is within these ranges, excellent light-emitting characteristics may be obtained without a substantial increase in driving voltage.

Next, the electron transport region may be disposed on the emission layer.

The electron transport region may include at least one selected from a hole blocking layer, an electron transport layer, and an electron injection layer.

For example, the electron transport region may have a structure of hole blocking layer/electron transport layer/electron injection layer or a structure of electron transport layer/electron injection layer, but the structure of the electron transport region is not limited thereto. The electron transport layer may have a single-layered structure or a multi-layered structure including two or more materials.

Conditions for forming a hole blocking layer, an electron transport layer, and an electron injection layer of the electron transport region may be understood by referring to conditions for forming the hole injection layer.

When the electron transport region includes a hole blocking layer, the hole blocking layer may include, for example, at least one of BCP and Bphen, but embodiments are not limited thereto:

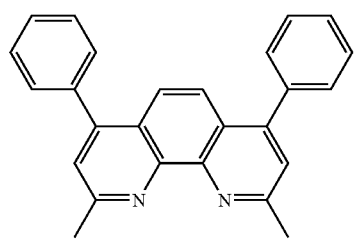

BCP

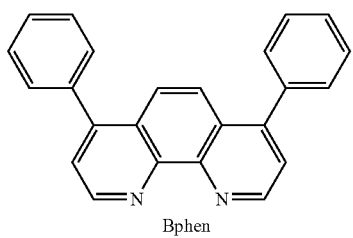

Bphen

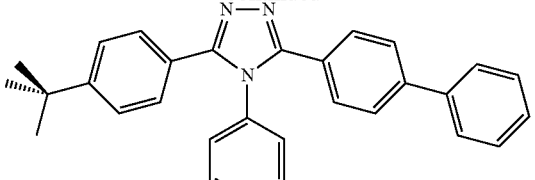

TAZ

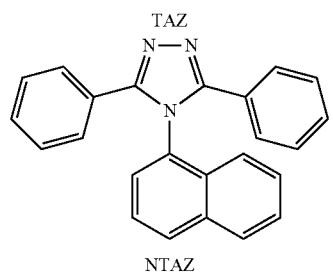

NTAZ

In various embodiments, the hole blocking layer may include the condensed cyclic compound represented by Formula 1.

A thickness of the hole blocking layer may be in a range of about 20 Å to about 1,000 Å, for example, about 30 Å to about 300 Å. While not wishing to be bound by theory, it is understood that when the thickness of the hole blocking layer is within these ranges, excellent hole blocking characteristics may be obtained without a substantial increase in driving voltage.

The electron transport layer may further include at least one selected from BCP, Bphen, Alq$_3$, BAlq, TAZ, and NTAZ:

In various embodiments, the electron transport layer may include at least one selected from Compounds ET1, ET2, and ET3, but embodiments are not limited thereto.

A thickness of the electron transport layer may be in a range of about 100 Å to about 1,000 Å, for example, about 150 Å to about 500 Å. While not wishing to be bound by theory, it is understood that when the thickness of the electron transport layer is within these ranges, satisfactory electron transporting characteristics may be obtained without a substantial increase in driving voltage.

The electron transport layer may further include, in addition to these materials, a metal-containing material.

The metal-containing material may include a lithium (Li) complex. The Li complex may include, for example, Compound ET-D1 (lithium quinolate LiQ)) or Compound ET-D2:

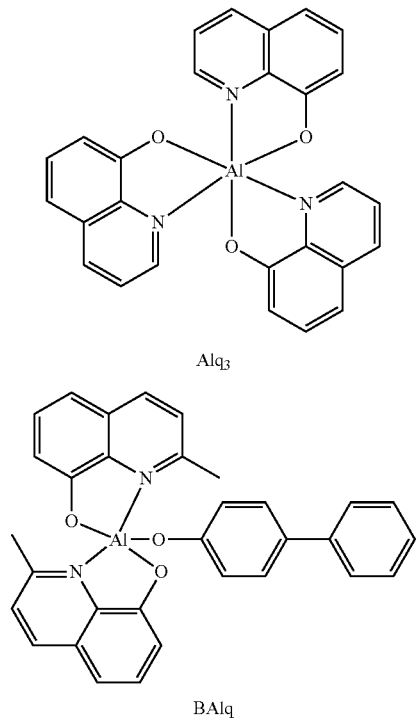

Alq$_3$

BAlq

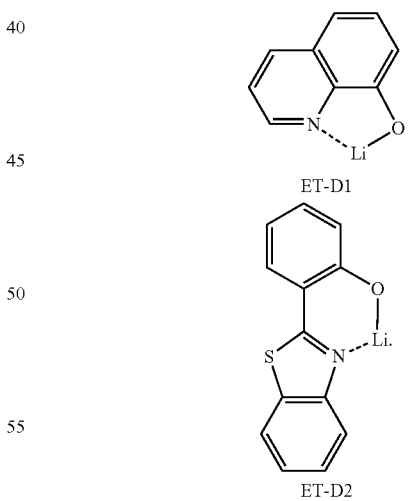

ET-D1

ET-D2

In addition, the electron transport region may include an electron injection layer that facilitates electron injection from the second electrode 19.

The electron injection layer may include at least one selected from LiQ, LiF, NaCl, CsF, Li$_2$O, and BaO.

A thickness of the electron injection layer may be in a range of about 1 Å to about 100 Å, for example, about 3 Å to about 90 Å. While not wishing to be bound by theory, it is understood that when the thickness of the electron injection layer is within these ranges, satisfactory electron injecting characteristics may be obtained without a substantial increase in driving voltage.

The second electrode 19 may be disposed on the organic layer 15. The second electrode 19 may be a cathode. A material for forming the second electrode 19 may be a metal having a relatively low work function, an alloy, an electrically conductive compound, and a combination thereof. For example, Li, Mg, Al, Al—Li, Ca, Mg—In, or Mg—Ag may be used as a material for forming the second electrode 19. In various embodiments, to manufacture a top emission-type light-emitting device, a transmissive electrode formed using ITO or IZO may be used as the second electrode 19.

In an embodiment, the organic layer 15 of the organic light-emitting device may include the hole transport region and the emission layer, and the hole transport region and the emission layer may each independently include the condensed cyclic compound represented by Formula 1, wherein the condensed cyclic compound represented by Formula 1 in the hole transport region may be identical to the condensed cyclic compound represented by Formula 1 in the emission layer.

In various embodiments, the organic layer 15 of the organic light-emitting device may include the hole transport region and the emission layer, and the hole transport region and the emission layer may each independently include the condensed cyclic compound represented by Formula 1, wherein the condensed cyclic compound represented by Formula 1 in the hole transport region may be different from the condensed cyclic compound represented by Formula 1 in the emission layer.

Here, the hole transport region may include at least one of a hole transport layer and an electron blocking layer, and the condensed cyclic compound represented by Formula 1 may be in i) a hole transport layer, ii) an electron blocking layer, or iii) both in the hole transport layer and the electron blocking layer. Here, the electron blocking layer may directly contact the emission layer.

In various embodiments, the organic layer 15 of the organic light-emitting device may include the emission layer and the electron transport region, and the emission layer and the electron transport region may each independently include the condensed cyclic compound represented by Formula 1, wherein the condensed cyclic compound represented by Formula 1 in the emission layer may be different from the condensed cyclic compound represented by Formula 1 in the electron transport region.

Here, the electron transport region may include at least one of an electron transport layer and a hole blocking layer, and the condensed cyclic compound represented by Formula 1 may be in i) an electron transport layer, ii) a hole blocking layer or iii) both in the electron transport layer and the hole blocking layer. Here, the hole blocking layer may directly contact the emission layer.

Hereinbefore, the organic light-emitting device 10 has been described with reference to FIG. 1, but is not limited thereto.

A $C_1$-$C_{60}$ alkyl group as used herein refers to a linear or branched aliphatic saturated hydrocarbon monovalent group having 1 to 60 carbon atoms. Examples thereof include a methyl group, an ethyl group, a propyl group, an iso-butyl group, a sec-butyl group, a tert-butyl group, a pentyl group, an iso-amyl group, and a hexyl group. A $C_1$-$C_{60}$ alkylene group as used herein refers to a divalent group having the same structure as the $C_1$-$C_{60}$ alkyl group.

A $C_1$-$C_{60}$ alkoxy group as used herein refers to a monovalent group represented by —$OA_{101}$ (wherein $A_{101}$ is the $C_1$-$C_{60}$ alkyl group). Examples thereof include a methoxy group, an ethoxy group, and an iso-propyloxy (iso-propoxy) group.

A $C_2$-$C_{60}$ alkenyl group as used herein refers to a hydrocarbon group formed by including at least one carbon-carbon double bond in the middle or at either terminal end of the $C_2$-$C_{60}$ alkyl group. Examples thereof include an ethenyl group, a propenyl group, and a butenyl group. A $C_2$-$C_{60}$ alkenylene group as used herein refers to a divalent group having the same structure as the $C_2$-$C_{60}$ alkenyl group.

A $C_2$-$C_{60}$ alkynyl group as used herein refers to a hydrocarbon group formed by including at least one carbon-carbon triple bond in the middle or at either terminal end of the $C_2$-$C_{60}$ alkyl group. Examples thereof include an ethynyl group and a propynyl group. A $C_2$-$C_{60}$ alkynylene group as used herein refers to a divalent group having the same structure as the $C_2$-$C_{60}$ alkynyl group.

A $C_3$-$C_{10}$ cycloalkyl group as used herein refers to a monovalent saturated hydrocarbon monocyclic group having 3 to 10 carbon atoms. Examples thereof include a cyclopropyl group, a cyclobutyl group, a cyclopentyl group, a cyclohexyl group, and a cycloheptyl group. A $C_3$-$C_{10}$ cycloalkylene group as used herein refers to a divalent group having the same structure as the $C_3$-$C_{10}$ cycloalkyl group.

A $C_1$-$C_{10}$ heterocycloalkyl group as used herein refers to a monovalent saturated monocyclic group having at least one heteroatom selected from N, O, P, Si, and S as a ring-forming atom and 1 to 10 carbon atoms. Examples thereof include a tetrahydrofuranyl group and a tetrahydrothiophenyl group. A $C_1$-$C_{10}$ heterocycloalkylene group as used herein refers to a divalent group having the same structure as the $C_1$-$C_{10}$ heterocycloalkyl group.

A $C_3$-$C_{10}$ cycloalkenyl group as used herein refers to a monovalent monocyclic group that has 3 to 10 carbon atoms and at least one carbon-carbon double bond in the ring thereof, and which is not aromatic. Examples thereof include a cyclopentenyl group, a cyclohexenyl group, and a cycloheptenyl group. A $C_3$-$C_{10}$ cycloalkenylene group as used herein refers to a divalent group having the same structure as the $C_3$-$C_{10}$ cycloalkenyl group.

A $C_1$-$C_{10}$ heterocycloalkenyl group as used herein refers to a monovalent monocyclic group that has at least one heteroatom selected from N, O, P, Si, and S as a ring-forming atom, 1 to 10 carbon atoms, and at least one carbon-carbon double bond in the ring. Examples of the $C_2$-$C_{10}$ heterocycloalkenyl group include a 2,3-dihydrofuranyl group and a 2,3-dihydrothiophenyl group. A $C_1$-$C_{10}$ heterocycloalkenylene group as used herein refers to a divalent group having the same structure as the $C_1$-$C_{10}$ heterocycloalkenyl group.

A $C_6$-$C_{60}$ aryl group as used herein refers to a monovalent group having a carbocyclic aromatic system having 6 to 60 carbon atoms, and a $C_6$-$C_{60}$ arylene group as used herein refers to a divalent group having a carbocyclic aromatic system having 6 to 60 carbon atoms. Examples of the $C_6$-$C_{60}$ aryl group a phenyl group, a naphthyl group, an anthracenyl group, a phenanthrenyl group, a pyrenyl group, and a chrysenyl group. When the $C_6$-$C_{60}$ aryl group and the $C_6$-$C_{60}$ arylene group each include two or more rings, the respective rings may be fused to each other.

A $C_1$-$C_{60}$ heteroaryl group as used herein refers to a monovalent group having a heterocyclic aromatic system that has at least one heteroatom selected from N, O, P, and S as a ring-forming atom, and 1 to 60 carbon atoms. A $C_1$-$C_{60}$ heteroarylene group as used herein refers to a divalent group having a carbocyclic aromatic system that has at least one heteroatom selected from N, O, P, and S as a ring-forming atom and 1 to 60 carbon atoms. Examples of the $C_1$-$C_{60}$ heteroaryl group include a pyridinyl group, a pyrimidinyl group, a pyrazinyl group, a pyridazinyl group, a triazinyl group, a quinolinyl group, and an isoquinolinyl group. When the $C_1$-$C_{60}$ heteroaryl group and the $C_1$-$C_{60}$ heteroarylene group each include two or more rings, the respective rings may be fused to each other.

A $C_6$-$C_{60}$ aryloxy group as used herein indicates —$OA_{102}$ (wherein $A_{102}$ is the $C_6$-$C_{60}$ aryl group), and a $C_6$-$C_{60}$ arylthio group as used herein indicates -$SA_{103}$ (wherein $A_{103}$ is the $C_6$-$C_{60}$ aryl group).

A monovalent non-aromatic condensed polycyclic group as used herein refers to a monovalent group (for example, a group having 8 to 60 carbon atoms) that has two or more rings condensed to each other, only carbon atoms as a ring forming atom, and which is non-aromatic in the entire molecular structure. An example of the non-aromatic condensed polycyclic group includes a fluorenyl group. A divalent non-aromatic condensed polycyclic group as used herein refers to a divalent group having the same structure as the monovalent non-aromatic condensed polycyclic group.

A monovalent non-aromatic condensed heteropolycyclic group as used herein refers to a monovalent group (for example, a group having 2 to 60 carbon atoms) that has two or more rings condensed to each other, has a heteroatom selected from N, O, P, Si, and S, other than carbon atoms, as a ring-forming atom, and which is non-aromatic in the entire molecular structure. An example of the monovalent non-aromatic condensed heteropolycyclic group includes a carbazolyl group. A divalent non-aromatic condensed heteropolycyclic group as used herein refers to a divalent group having the same structure as the monovalent non-aromatic condensed heteropolycyclic group.

In Formula 1, at least one of substituents selected from the substituted $C_1$-$C_{60}$ alkyl group, the substituted $C_2$-$C_{60}$ alkenyl group, the substituted $C_2$-$C_{60}$ alkynyl group, the substituted $C_3$-$C_{10}$ cycloalkyl group, the substituted $C_1$-$C_{10}$ heterocycloalkyl group, the substituted $C_3$-$C_{10}$ cycloalkenyl group, the substituted $C_1$-$C_{10}$ heterocycloalkenyl group, the substituted $C_6$-$C_{60}$ aryl group, the substituted $C_6$-$C_{60}$ aryloxy group, the substituted $C_6$-$C_{60}$ arylthio group, the substituted $C_1$-$C_{60}$ heteroaryl group, the substituted monovalent non-aromatic condensed polycyclic group, and the substituted monovalent non-aromatic condensed heteropolycyclic group may be selected from:

deuterium, —$CD_3$, —$CD_2H$, —$CDH_2$, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group and $C_1$-$C_{60}$ alkoxy group;

a $C_1$-$C_{60}$ alkyl group, a $C_2$-$C_{60}$ alkenyl group, a $C_2$-$C_{60}$ alkynyl group and $C_1$-$C_{60}$ alkoxy group, each substituted with at least one selected from deuterium, —$CD_3$, —$CD_2H$, —$CDH_2$, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —$Si(Q_{11})(Q_{12})(Q_{13})$, —$N(Q_{14})(Q_{15})$, and —$B(Q_{16})(Q_{17})$, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group;

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group, each substituted with at least one selected from deuterium, —$CD_3$, —$CD_2H$, —$CDH_2$, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —$Si(Q_{21})(Q_{22})(Q_{23})$, —$N(Q_{24})(Q_{25})$, and —$B(Q_{26})(Q_{27})$; and —$Si(Q_{31})(Q_{32})(Q_{33})$, —$N(Q_{34})(Q_{35})$, and —$B(Q_{36})(Q_{37})$, and $Q_1$ to $Q_7$, $Q_{11}$ to $Q_{17}$, $Q_{21}$ to $Q_{27}$, and $Q_{31}$ to $Q_{37}$ may each independently be selected from hydrogen, deuterium, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted heterocycloalkyl group, a substituted or unsubstituted $C_3$-$C_{10}$ cycloalkenyl group, a substituted or unsubstituted heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, and a substituted or unsubstituted monovalent non-aromatic condensed heteropolycyclic group.

When a group containing a specified number of carbon atoms is substituted with any of the groups listed in the preceding paragraph, the number of carbon atoms in the resulting "substituted" group is defined as the sum of the carbon atoms contained in the original (unsubstituted) group and the carbon atoms (if any) contained in the substituent. For example, when the term "substituted $C_1$-$C_{30}$ alkyl" refers to a $C_1$-$C_{30}$ alkyl group substituted with $C_6$-$C_{30}$ aryl group, the total number of carbon atoms in the resulting aryl substituted alkyl group is $C_7$-$C_{60}$.

The term "biphenyl group" as used herein refers to a monovalent group in which two benzene groups are linked via a single bond.

The term "terphenyl group" as used herein refers to a monovalent group in which three benzene groups are linked via a single bond.

Hereinafter, a compound according to embodiments and an organic light-emitting device according to embodiments will be described in detail with reference to Synthesis Examples and Examples below, but the present inventive concept is not limited thereto. The expression "'B' was used instead of 'A'" used in describing Synthesis Examples below means that the number of molar equivalents of 'B' used was identical to the number of molar equivalents of 'A'.

EXAMPLES

Synthesis Example 1: Synthesis of Compound 38

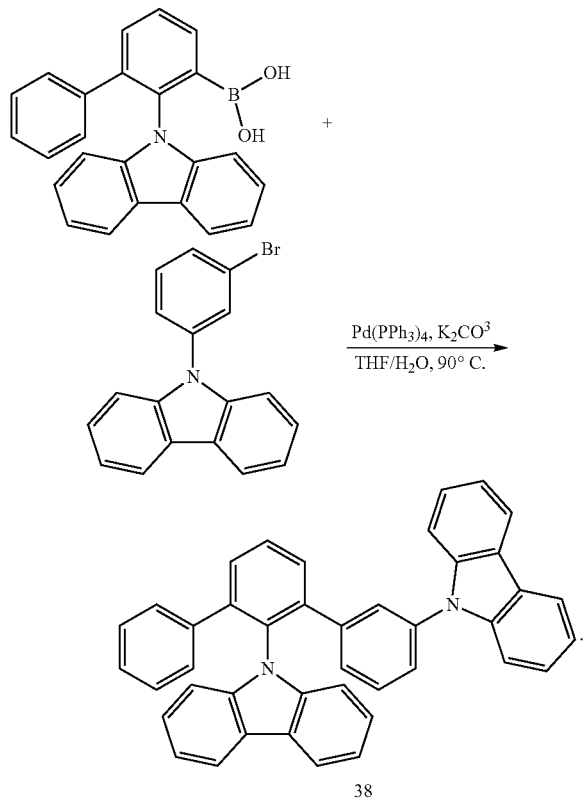

38

6.81 grams (g) (18.75 millimoles, mmol) of (2-(9H-carbazol-9-yl)-[1,1'-biphenyl]-3-yl)boronic acid, 6.34 g (19.68 mmol) of 9-(3-bromophenyl)-9H-carbazole, 1.08 g (0.94 mmol) of Pd(PPh$_3$)$_4$, and 7.77 g (56.24 mmol) of K$_2$CO$_3$ were mixed in a THF/H$_2$O solution (40 ml/15 ml, wherein ml=milliliters), and the mixed solution was heated and stirred in a sealed tube at a temperature of 90° C. for 24 hours. Then, TFT in the product obtained therefrom was removed under reduced pressure, and the resulting product was dissolved in methylene chloride and washed twice using H$_2$O. The organic layer was dried using MgSO$_4$, and the solvent was removed under reduced pressure. The resulting product was subjected to silica hot filtration using toluene, and the resulting solution was concentrated under reduced pressure. The concentrated toluene solution was poured into MeOH (2 liters, L), at which time, a precipitate was formed. The precipitate was stirred for 18 hours, and a solid product was obtained by filtration. The resulting solid product was recrystallized using ethyl acetate, thereby obtaining 10.2 g of Compound 38. The resulting compound was identified by LC-MS.

C$_{42}$H$_{28}$N$_2$: M$^+$ 560.435

Synthesis Example 2: Synthesis of Compound 39

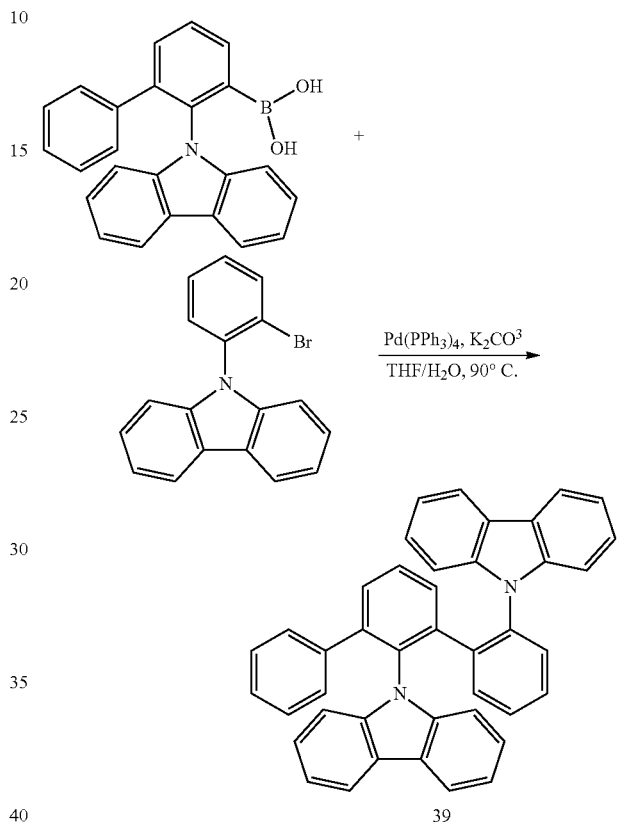

39

Compound 39 was obtained in the same manner as in Synthesis Example 1, except that 9-(2-bromophenyl)-9H-carbazole was used instead of 9-(3-bromophenyl)-9H-carbazole. The resulting compound was identified by LC-MS.

C$_{42}$H$_{28}$N$_2$: M$^+$ 560.440

Example 1

A glass substrate, on which an indium tin oxide (ITO) electrode (i.e., a first electrode or an anode) having a thickness of 1,500 Å, was ultrasonically cleaned by using distilled water. After completing the washing of the glass substrate using distilled water, the glass substrate was ultrasonically washed again using solvents, such as isopropyl alcohol, acetone, and methanol, and then, dried. The glass substrate was transported to a plasma washing machine, washed using oxygen plasma for 5 minutes, and then, transported to a vacuum evaporator.

Compounds HT3 and HP-1 were co-deposited on the ITO electrode of the glass substrate to form a hole injection layer having a thickness of 100 Å, Compound HT3 was deposited on the hole injection layer to form a hole transport layer having a thickness of 1,300 Å, and mCP was deposited on the hole transport layer to form an electron blocking layer having a thickness of 150 Å, thereby forming a hole transport region.

Compound 38 (as a host) and Compound PD97 (as a dopant having an amount of 10 percent by weight, wt %) were co-deposited on the hole transport region to form an emission layer having a thickness of 300 Å.

BCP was vacuum-deposited on the emission layer to form a hole blocking layer having a thickness of 100 Å, Compound ET3 and Liq were vacuum-deposited together on the hole blocking layer to form an electron transport layer having a thickness of 250 Å, and Liq was deposited on the electron transport layer to form an electron injection layer having a thickness of 5 Å. Then, Al was deposited on the electron injection layer to form an Al second electrode (i.e., a cathode) having a thickness of 1,000 Å, thereby completing the manufacture of an organic light-emitting device.

Example 2 and Comparative Examples 1 and 2

Organic light-emitting devices of Example 2 and Comparative Examples 1 and 2 were each manufactured in the same manner as in Example 1, except that compounds shown in Table 2 were each used as a host for forming the emission layer.

Evaluation Example 1: Evaluation of Characteristics of Organic Light-Emitting Device The luminescent efficiency, power efficiency, quantum emission efficiency, and lifespan of the organic light-emitting devices of Examples 1 and 2 and Comparative Examples 1 and 2 were measured using a Keithley 2400 current-voltage meter and a Minolta Cs-1000A brightness meter, and the results are shown in Table 2 as relative values for the data of the organic light-emitting device of Comparative Example 1. In Table 2, $T_{95}$ (at 1,000 candelas per square meter, cd/m$^2$) in the lifespan results means the time until the brightness of the organic light-emitting devices reaches about 95% of the initial brightness (100%), wherein the results are represented as relative values for the lifespan data ($T_{95}$ at 1,000 cd/m$^2$) of the organic light-emitting device of Comparative Example 1.

TABLE 2

| | Host | Luminescent efficiency (cd/A) | Power efficiency (lm/W) | Quantum emission efficiency (%) | $T_{95}$ (hr) |
|---|---|---|---|---|---|
| Example 1 | Compound 38 | 115% | 102% | 110% | 67% |
| Example 2 | Compound 39 | 108% | 102% | 107% | 210% |
| Comparative Example 1 | Compound A | 100% | 100% | 100% | 100% |
| Comparative Example 2 | Compound B | 78% | 77% | 77% | 1% |

PD79

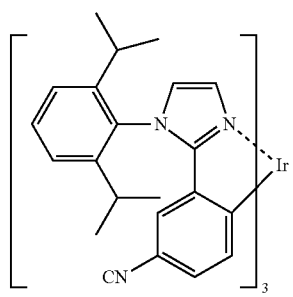

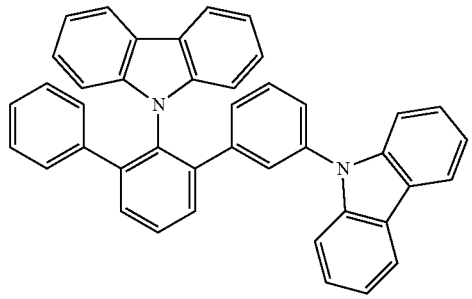

38

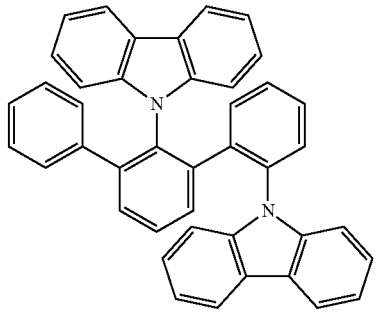

39

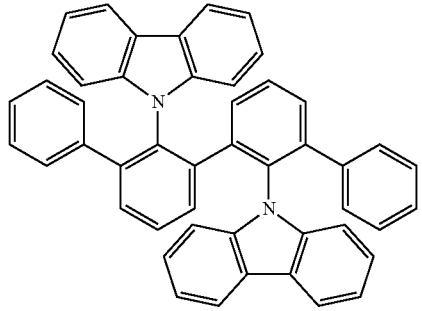

A

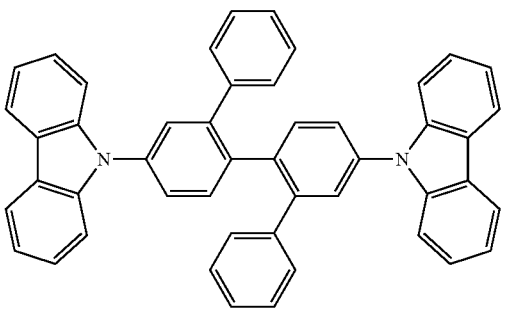

B

Referring to Table 2, it was confirmed that the organic light-emitting devices of Examples 1 and 2 had excellent luminescent efficiency, high power efficiency, high quantum emission efficiency, and long lifespan characteristics, compared to those of the organic light-emitting devices of Comparative Examples 1 and 2.

As described above, a condensed cyclic compound represented by Formula 1 has excellent electric characteristics and thermal stability, and an organic light-emitting device including the condensed cyclic compound represented by Formula 1 has excellent light-emission efficiency, high power efficiency, high quantum efficiency, and long lifespan characteristics.

It should be understood that embodiments described herein should be considered in a descriptive sense only and not for purposes of limitation. Descriptions of features or aspects within each embodiment should typically be considered as available for other similar features or aspects in other embodiments.

While one or more embodiments have been described with reference to the figures, it will be understood by those of ordinary skill in the art that various changes in form and details may be made therein without departing from the spirit and scope of the present inventive concept as defined by the following claims.

What is claimed is:

1. A condensed cyclic compound represented by one of Formulae 1-1A, 1-1C to 1-1D, 1-2A to 1-2D, and 1-3A to 1-3D:

Formula 1-1A
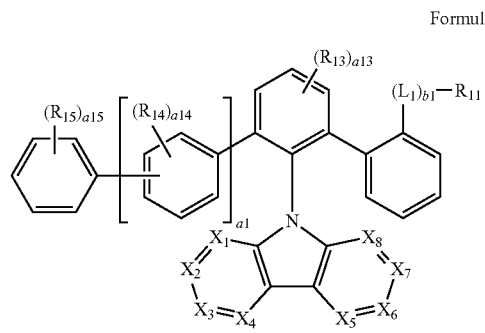

Formula 1-1C
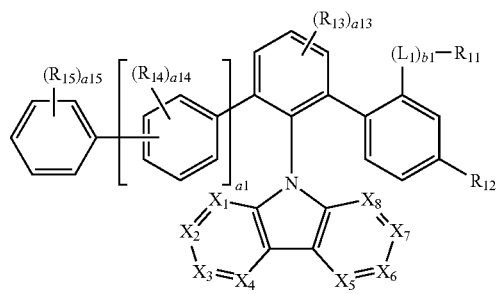

Formula 1-1D
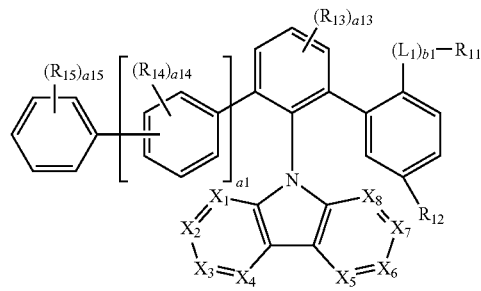

Formula 1-2A
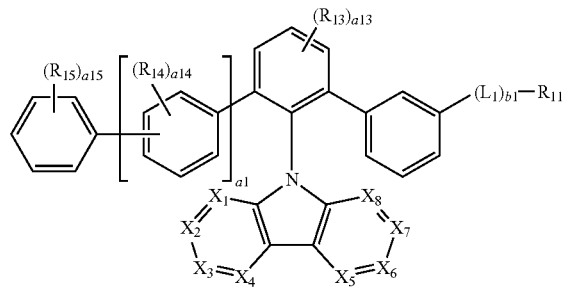

Formula 1-2B
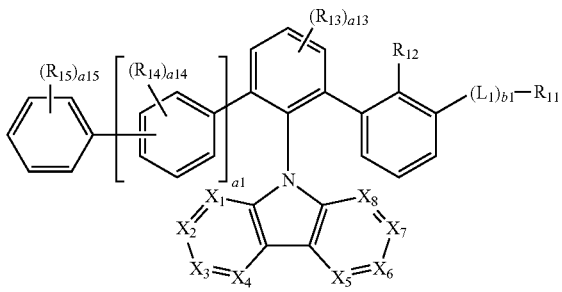

Formula 1-2C
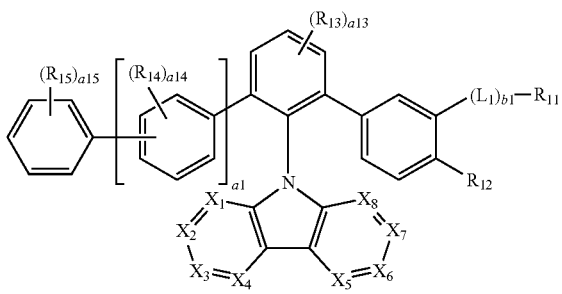

Formula 1-2D
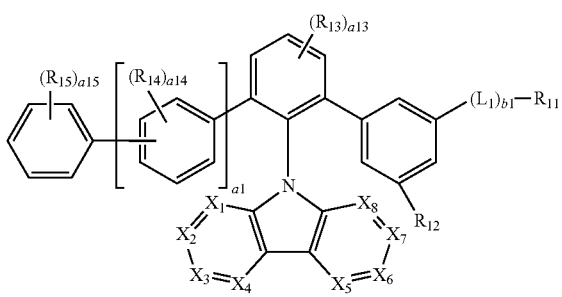

Formula 1-3A
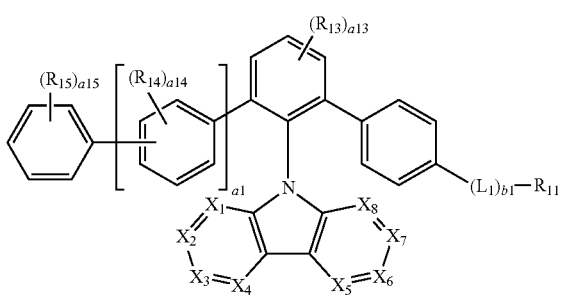

Formula 1-3B
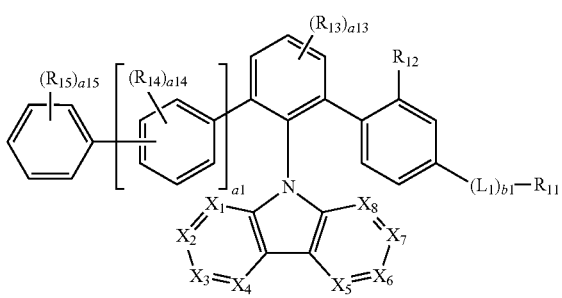

-continued

Formula 1-3C

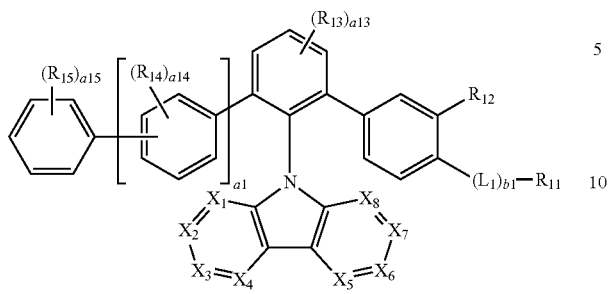

Formula 1-3D

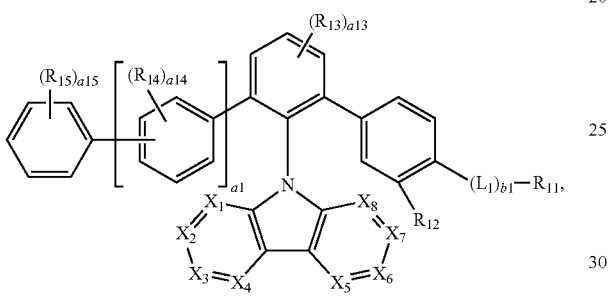

wherein, in Formulae 1-1A, 1-1C to 1-1D, 1-2A to 1-2D and 1-3A to 1-3D, $X_1$ is N or $C(R_1)$, $X_2$ is N or $C(R_2)$, $X_3$ is N or $C(R_3)$, $X_4$ is N or $C(R_4)$, $X_5$ is N or $C(R_5)$, $X_6$ is N or $C(R_6)$, $X_7$ is N or $C(R_7)$, and $X_8$ is N or $C(R_8)$, wherein at least one selected from $X_1$ to $X_8$ is not N, a1 is an integer selected from 0 to 3, Formula 2-1

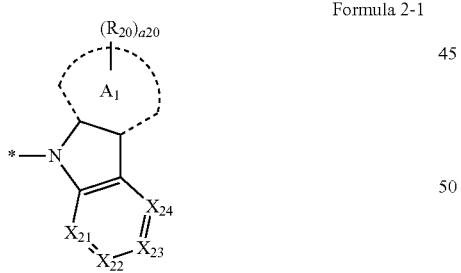

Formula 2-2

Formula 2-3

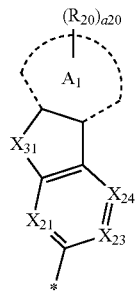

Formula 2-4

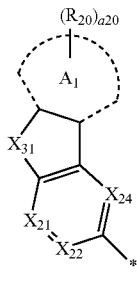

Formula 2-5

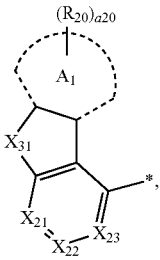

in Formulae 2-1 to 2-5, $X_{21}$ is N or $C(R_{21})$, $X_{22}$ is N or $C(R_{22})$, $X_{23}$ is N or $C(R_{23})$, and $X_{24}$ is N or $C(R_{24})$, wherein at least one selected from $X_{21}$ to $X_{24}$ in Formulae 2-1 is not N, in Formulae 2-1 to 2-5, ring $A_1$ is a benzene group, a pyridine group, a pyrimidine group, a pyridazine group, a pyrazine group, a triazine group, a fluorene group, a carbazole group, a dibenzofuran group, a dibenzothiophene group, a dibenzosilol group, an azafluorene group, an azacarbazole group, an azadibenzofuran group, an azadibenzothiophene group, or an azadibenzosilol group, in Formulae 2-2 to 2-5, $X_{31}$ is O, S, $N(R_{31})$, $C(R_{32})(R_{33})$, or $Si(R_{32})(R_{33})$, in Formulae 2-2 to 2-5, $X_{31}$ is $N(R_{31})$, or ring $A_1$ is a carbazole group or an azacarbazole group, in Formulae 1-1A, 1-1C to 1-1D, 1-2A to 1-2D and 1-3A to 1-3D, $R_{11}$ is selected from:

a group represented by one selected from Formulae 2-1 to 2-5;

an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an indazolyl group, a quinolinyl group, an isoquinolinyl group, a benzoquinolinyl group, a phthalazinyl group, a naphthyridinyl group, a quinoxalinyl group, a quinazolinyl group, a cinnolinyl group, a phenanthridinyl group, an acridinyl group, a phenanthrolinyl group, a phenazinyl group, a benzimidazolyl group, an isobenzothiazolyl group, a benzoxazolyl group, an isobenzoxazolyl group, a triazolyl group, a tetrazolyl group, an oxadiazolyl group, a triazinyl group, a thiadiazolyl group, an imidazopyridinyl group, and an imidazopyrimidinyl group; and an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an indazolyl group, a quinolinyl group, an isoquinolinyl group, a benzoquinolinyl group, a phthalazinyl group, a naphthyridinyl group, a quinoxalinyl group, a quinazolinyl group, a cinnolinyl group, a phenanthridinyl group, an acridinyl group, a phenanthrolinyl group, a phenazinyl group, a benzimidazolyl group, an isobenzothiazolyl group, a benzoxazolyl group, an isobenzoxazolyl group, a triazolyl group, a tetrazolyl group, an oxadiazolyl group, a triazinyl group, a thiadiazolyl group, an imidazopyridinyl group, and an imidazopyrimidinyl group, each substituted with at least one selected from deuterium, —$CD_3$, —$CD_2H$, —$CDH_2$, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, a biphenyl group, and a terphenyl group, in Formulae 1-1A, 1-1C to 1-1D, 1-2A to 1-2D and 1-3A to 1-3D, $R_{12}$ is selected from deuterium, —F, —Cl, —Br, —I, a hydroxyl group, a nitro group, an amino group, an amidino group, a hydrazine group, a hydrazone group, a carboxylic acid group or a salt thereof, a sulfonic acid group or a salt thereof, a phosphoric acid group or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, a substituted or unsubstituted monovalent non-aromatic condensed heteropolycyclic group, —$Si(Q_1)(Q_2)(Q_3)$, —$N(Q_4)(Q_5)$, and —$B(Q_6)(Q_7)$, wherein Rig does not include a cyano group, in Formulae 1-1A, 1-1C to 1-1D, 1-2A to 1-2D and 1-3A to 1-3D, when a1 is 0, the phenyl group substituted with $(R_{15})_{a15}$ is attached to the phenyl group substituted with $(R_{13})_{a13}$ and when b1 is 0, then $R_{11}$ is attached to the phenyl group substituted with $(R_{13})_{a13}$, in Formulae 1-1A, 1-1C to 1-1D, 1-2A to 1-2D and 1-3A to 1-3D, and 2-1 to 2-5, $R_1$ to $R_8$, $R_{13}$ to $R_{15}$, $R_{20}$ to $R_{24}$, and $R_{31}$ to $R_{33}$ are each independently selected from:

hydrogen, deuterium, a cyano group, a $C_1$-$C_{20}$ alkyl group, a $C_1$-$C_{20}$ alkoxy group, a phenyl group, a biphenyl group, a terphenyl group, a naphthyl group, a fluorenyl group, a pyridinyl group, a pyrimidinyl group, a pyrazinyl group, a pyridazinyl group, a triazinyl group, a dibenzofuranyl group, a dibenzothiophenyl group, and a dibenzosilolyl group;

a $C_1$-$C_{20}$ alkyl group and a $C_1$-$C_{20}$ alkoxy group, each substituted with at least one of deuterium and a cyano group; and a phenyl group, a biphenyl group, a terphenyl group, a naphthyl group, a fluorenyl group, a pyridinyl group, a pyrimidinyl group, a pyrazinyl group, a pyridazinyl group, a triazinyl group, a dibenzofuranyl group, a dibenzothiophenyl group, and a dibenzosilolyl group, each substituted with at least one selected from deuterium, a cyano group, a $C_1$-$C_{20}$ alkyl group, a $C_1$-$C_{20}$ alkoxy group, a phenyl group, a biphenyl group, a terphenyl group, a naphthyl group, a fluorenyl group, a pyridinyl group, a pyrimidinyl group, a pyrazinyl group, a pyridazinyl group, a triazinyl group, a dibenzofuranyl group, a dibenzothiophenyl group, and a dibenzosilolyl group, wherein $R_{13}$ does not include a cyano group, in Formulae 1-1A, 1-1C to 1-1D, 1-2A to 1-2D and 1-3A to 1-3D, a13 is an integer selected from 0 to 3, wherein, when a13 is 2 or more, 2 or more groups $R_{13}$ are identical to or different from each other, in Formulae 1-1A, 1-1C to 1-1D, 1-2A to 1-2D and 1-3A to 1-3D, a14 is an integer selected from 0 to 4, wherein, when a14 is 2 or more, 2 or more groups $R_{14}$ are identical to or different from each other, in Formulae 1-1A, 1-1C to 1-1D, 1-2A to 1-2D and 1-3A to 1-3D, a15 is an integer selected from 0 to 5, wherein, when a15 is 2 or more, 2 or more groups $R_{15}$ are identical to or different from each other, in Formulae 2-1 to 2-5, a20 is an integer selected from 0 to 8, wherein, when a20 is 2 or more, 2 or more groups $R_{20}$ are identical to or different from each other, in Formulae 1-1A, 1-1C to 1-1D, 1-2A to 1-2D and 1-3A to 1-3D, $L_1$ is a substituted or unsubstituted $C_3$-$C_{10}$ cycloalkylene group, a substituted or unsubstituted $C_1$-$C_{10}$ heterocycloalkylene group, a substituted or unsubstituted $C_3$-$C_{10}$ cycloalkenylene group, a substituted or unsubstituted $C_1$-$C_{10}$ heterocycloalkenylene group, a substituted or unsubstituted $C_6$-$C_{60}$ arylene group, a substituted or unsubstituted $C_1$-$C_{60}$ heteroarylene group, a substituted or unsubstituted divalent non-aromatic condensed polycyclic group, and a substituted or unsubstituted divalent non-aromatic condensed heteropolycyclic group, wherein $L_2$ does not include a cyano group, in Formulae 1-1A, 1-1C to 1-1D, 1-2A to 1-2D and 1-3A to 1-3D, b1 is an integer selected from 0 to 5, wherein, when b1 is 2 or more, 2 or more groups $L_1(s)$ are identical to or different from each other, in the condensed cyclic compound represented by Formulae 1-1A, 1-1C to 1-1D, 1-2A to 1-2D and 1-3A to 1-3D, the number of carbazole ring(s) is 0, 1, or 2, the condensed cyclic compound represented by Formulae 1-1A, 1-1C to 1-1D, 1-2A to 1-2D and 1-3A to 1-3D has an asymmetrical structure, in Formulae 2-1 to 2-5, * indicates a binding site to a neighboring atom, at least one substituent selected from substituent(s) of the substituted $C_3$-$C_{10}$ cycloalkylene group, the substituted $C_1$-$C_{10}$ heterocycloalkylene group, the substituted $C_3$-$C_{10}$ cycloalkenylene group, the substituted $C_1$-$C_{10}$ heterocycloalkenylene group, the substituted $C_6$-$C_{60}$ arylene group, the substituted $C_1$-$C_{60}$ heteroarylene group, the substituted divalent non-aromatic condensed polycyclic group, the substituted divalent non-aromatic condensed heteropolycyclic group, the substituted $C_1$-$C_{60}$ alkyl group, the substituted $C_2$-$C_{60}$ alkenyl group, the substituted $C_2$-$C_{60}$ alkynyl group, the substituted $C_3$-$C_{10}$ cycloalkyl group, the substituted $C_1$-$C_{10}$ heterocycloalkyl group, the substituted $C_3$-$C_{10}$ cycloalkenyl group, the substituted $C_1$-$C_{10}$ heterocycloalkenyl group, the substituted $C_6$-$C_{60}$ aryl group, the substituted $C_6$-$C_{60}$ aryloxy group, the substituted $C_6$-$C_{60}$ arylthio group, the substituted $C_1$-$C_{60}$ heteroaryl group, the substituted monovalent non-aromatic condensed polycyclic group, and the substituted monovalent non-aromatic condensed heteropolycyclic group is selected from:

deuterium, —F, —Cl, —Br, —I, —$CD_3$, —$CD_2H$, —$CDH_2$, —$CF_3$, —$CF_2H$, —$CFH_2$, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, and $C_1$-$C_{60}$ alkoxy group;

a $C_1$-$C_{60}$ alkyl group, a $C_2$-$C_{60}$ alkenyl group, a $C_2$-$C_{60}$ alkynyl group, and a $C_1$-$C_{60}$ alkoxy group, each substituted with at least one selected from deuterium, —F, —Cl, —Br, —I, —$CD_3$, —$CD_2H$, —$CDH_2$, —$CF_3$, —$CF_2H$, —$CFH_2$, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —Si($Q_{11}$)($Q_{12}$)($Q_{13}$), —N($Q_{14}$)($Q_{15}$), and —B($Q_{16}$)($Q_{17}$);

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group;

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group, each substituted with at least one selected from deuterium, —F, —Cl, —Br, —I, —$CD_3$, —$CD_2H$, —$CDH_2$, —$CF_3$, —$CF_2H$, —$CFH_2$, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —Si($Q_{21}$)($Q_{22}$)($Q_{23}$), —N($Q_{24}$)($Q_{25}$), and —B($Q_{26}$)($Q_{27}$); and —Si($Q_{31}$)($Q_{32}$)($Q_{33}$), —N($Q_{34}$)($Q_{35}$), and —B($Q_{36}$)($Q_{37}$), and $Q_1$ to $Q_7$, $Q_{11}$ to $Q_{17}$, $Q_{21}$ to $Q_{27}$, and $Q_{31}$ to $Q_{37}$ are each independently selected from hydrogen, deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, and a substituted or unsubstituted monovalent non-aromatic condensed heteropolycyclic group.

2. The condensed cyclic compound of claim 1, wherein a1 in Formulae 1-1A, 1-1C to 1-1D, 1-2A to 1-2D and 1-3A to 1-3D, is 0 or 1.

3. The condensed cyclic compound of claim 1, wherein ring $A_1$ is a benzene group, a pyridine group, a carbazole group, a dibenzofuran group, a dibenzothiophene group, or an azacarbazole group.

4. The condensed cyclic compound of claim 1, wherein $R_{11}$ is one selected from groups represented by Formulae 2-1A to 2-5A, 2-1B to 2-5B, 2-1C to 2-5C, 2-1D to 2-5D, 2-1E to 2-5E, 2-1F to 2-5F, and 2-1G to 2-5G:

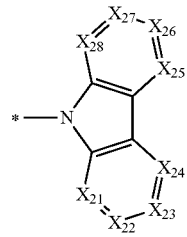

Formula 2-1A

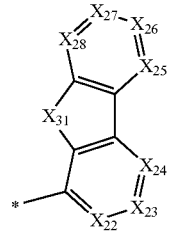

Formula 2-2A

Formula 2-3A
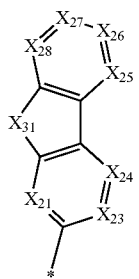
Formula 2-4A
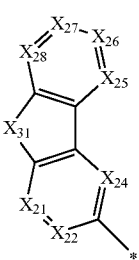
Formula 2-5A
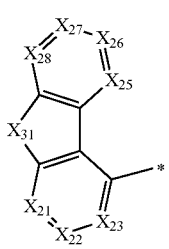
Formula 2-1B
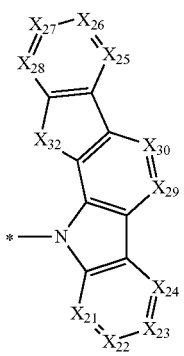
Formula 2-2B
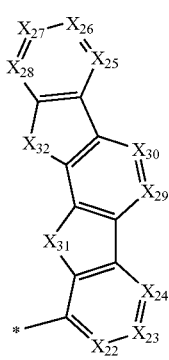
Formula 2-3B
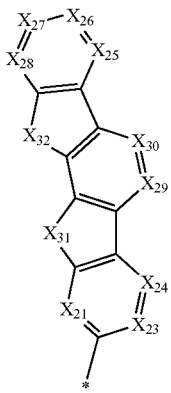
Formula 2-4B
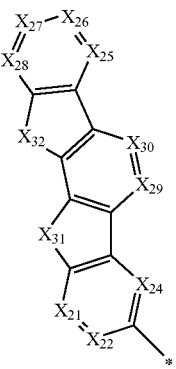
Formula 2-5B
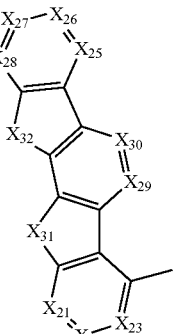
Formula 2-1C
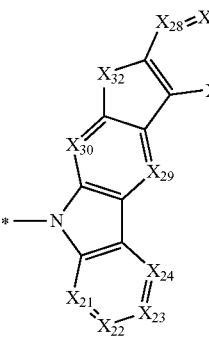

-continued
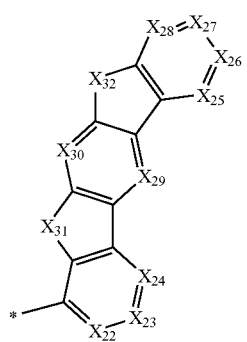
Formula 2-2C
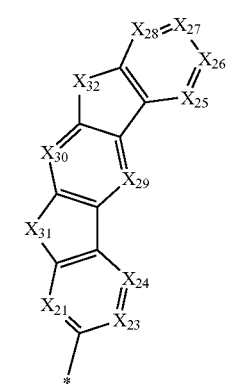
Formula 2-3C
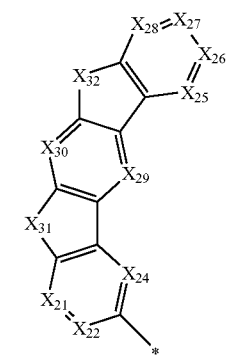
Formula 2-4C
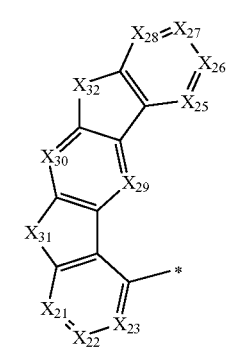
Formula 2-5C
-continued
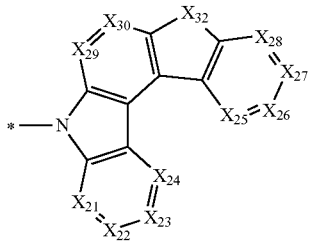
Formula 2-1D
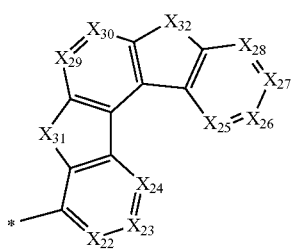
Formula 2-2D
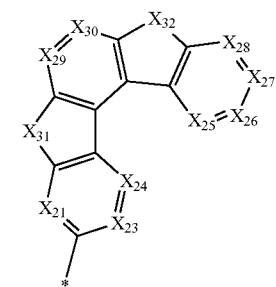
Formula 2-3D
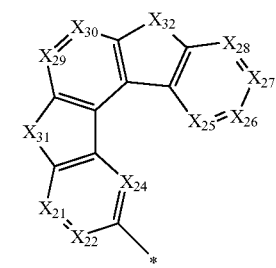
Formula 2-4D
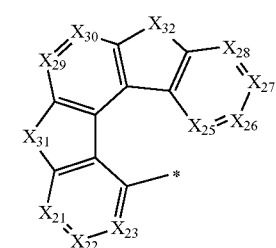
Formula 2-5D
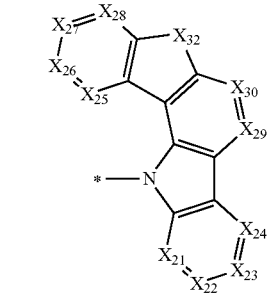
Formula 2-1E Formula 2-2E
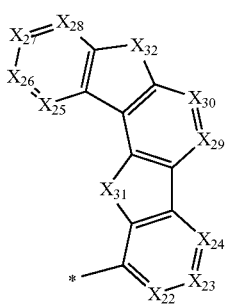
Formula 2-3E
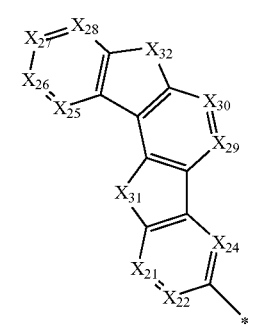
Formula 2-4E
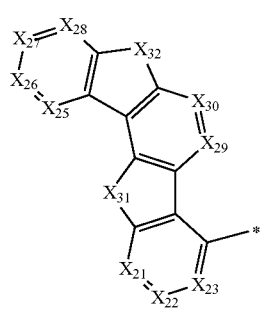
Formula 2-5E
Formula 2-1F
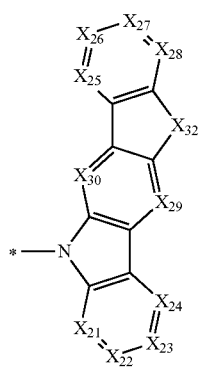
Formula 2-2F
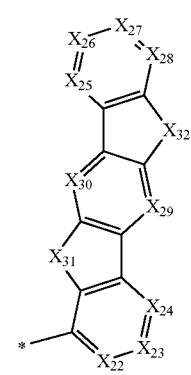
Formula 2-3F
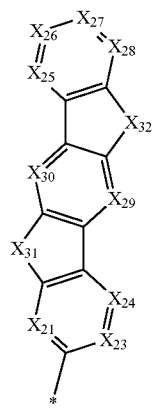
Formula 2-4F
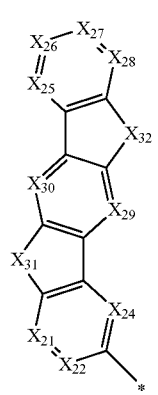

Formula 2-5F

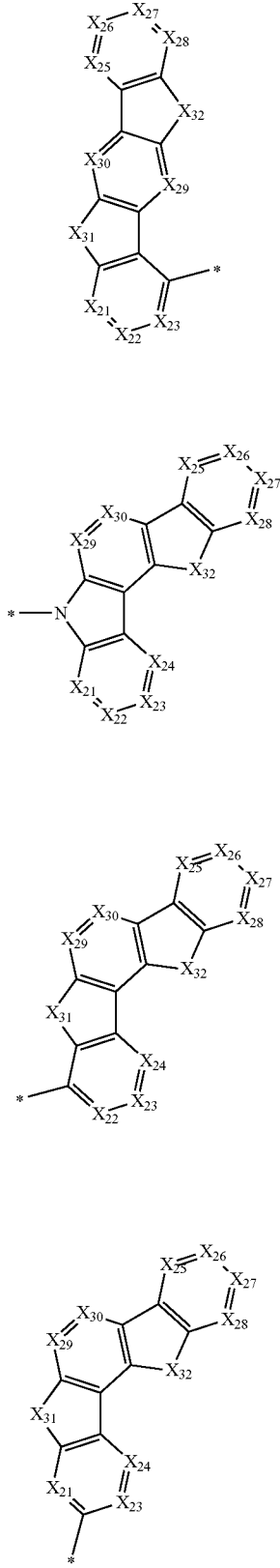

Formula 2-1G

Formula 2-2G

Formula 2-3G

Formula 2-4G

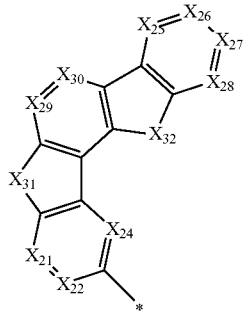

Formula 2-5G

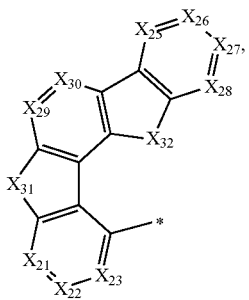

wherein, in Formulae 2-1A to 2-5A, 2-1B to 2-5B, 2-1C to 2-5C, 2-1D to 2-5D, 2-1E to 2-5E, 2-1F to 2-5F, and 2-1G to 2-5G, $X_{21}$ to $X_{24}$ and $X_{31}$ are as defined in claim 1, $X_{25}$ is N or $C(R_{25})$, $X_{26}$ is N or $C(R_{26})$, $X_{27}$ is N or $C(R_{27})$, $X_{28}$ is N or $C(R_{28})$, $X_{29}$ is N or $C(R_{29})$, and $X_{30}$ is N or $C(R_{30})$, wherein at least one selected from $X_{25}$ to $X_{30}$ is not N, $R_{25}$ to $R_{30}$ are each independently as defined in connection with $R_{20}$ in claim 1, $X_{32}$ is O, S, $N(R_{34})$, $C(R_{35})(R_{36})$, or $Si(R_{35})(R_{36})$, $R_{34}$ is as defined in connection with $R_{31}$ in claim 1, $R_{35}$ and $R_{36}$ are each independently as defined in connection with $R_{32}$ in claim 1, in Formulae 2-2A to 2-5A, 2-2B to 2-5B, 2-2C to 2-5C, 2-2D to 2-5D, 2-2E to 2-5E, 2-2F to 2-5F, and 2-2G to 2-5G, i) when $X_{31}$ is O, S, $C(R_{32})(R_{33})$, or $Si(R_{32})(R_{33})$, $X_{32}$ is $N(R_{34})$, and ii) when $X_{32}$ is O, S, $C(R_{35})(R_{36})$, or $Si(R_{35})(R_{36})$, $X_{31}$ is $N(R_{31})$, and

* indicates a binding site to a neighboring atom.

5. The condensed cyclic compound of claim 4, wherein at least one of $X_{23}$ and $X_{26}$ in Formulae 2-1A to 2-5A, 2-1B to 2-5B, 2-1C to 2-5C, 2-1D to 2-5D, 2-1E to 2-5E, 2-1F to 2-5F, and 2-1G to 2-5G is C(CN) or N.

6. The condensed cyclic compound of claim 1, wherein $R_{11}$ is selected from:

an imidazolyl group, a pyridinyl group, a pyrazinyl group, a pyrimidinyl group, a pyridazinyl group, a quinolinyl group, an isoquinolinyl group, a quinoxalinyl group, a quinazolinyl group, a phenanthrolinyl group, a benzimidazolyl group, a triazinyl group, an imidazopyridinyl group, and an imidazopyrimidinyl group; and an imidazolyl group, a pyridinyl group, a pyrazinyl group, a pyrimidinyl group, a pyridazinyl group, a quinolinyl group, an isoquinolinyl group, a quinoxalinyl group, a quinazolinyl group, a phenanthrolinyl group, a benzimidazolyl group, a triazinyl group, an imidazopyridinyl group, and an imidazopyrimidinyl group, each substituted with at least one selected from deuterium, —$CD_3$, —$CD_2H$, —$CDH_2$, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a biphenyl group, a terphenyl group, an imidazolyl group, a pyridinyl group, a pyrazinyl group, a pyrimidinyl group, a pyridazinyl group, a quinolinyl group, an isoquinolinyl group, a quinoxalinyl group, a quinazolinyl group, a phenanthrolinyl group, a benzimidazolyl group, a triazinyl group, an imidazopyridinyl group, and an imidazopyrimidinyl group.

7. The condensed cyclic compound of claim 1, wherein $R_{11}$ is selected from groups represented by Formulae 5-1 to 5-55:

Formula 5-1
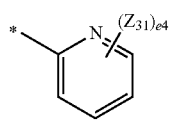

Formula 5-2
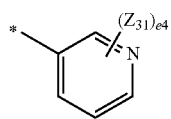

Formula 5-3
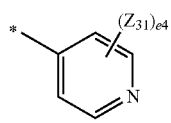

Formula 5-4
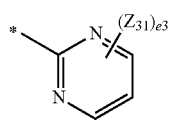

Formula 5-5
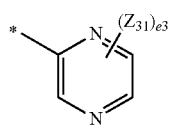

Formula 5-6
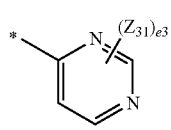

Formula 5-7
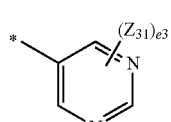

Formula 5-8
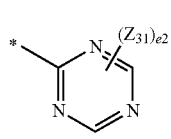

Formula 5-9
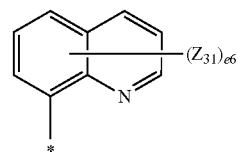

Formula 5-10
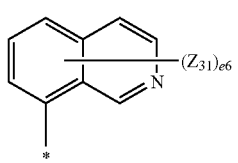

Formula 5-11
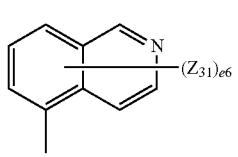

Formula 5-12
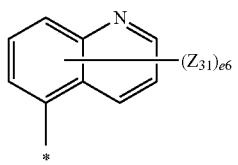

Formula 5-13
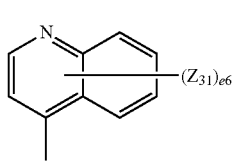

Formula 5-14
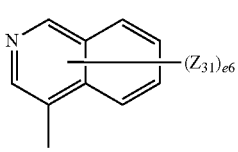

Formula 5-15
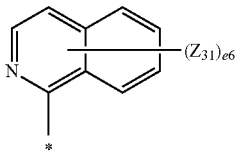

Formula 5-16
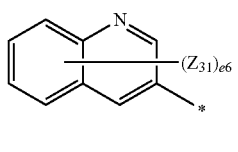

Formula 5-17
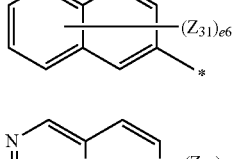

Formula 5-18
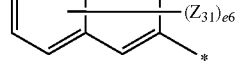

-continued
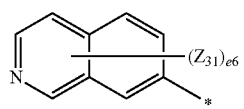
Formula 5-19
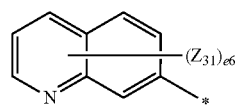
Formula 5-20
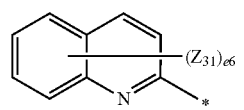
Formula 5-21
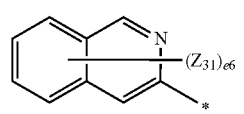
Formula 5-22
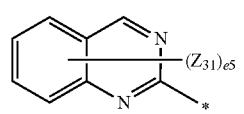
Formula 5-23
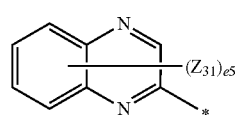
Formula 5-24
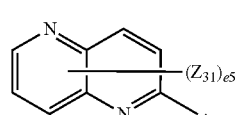
Formula 5-25
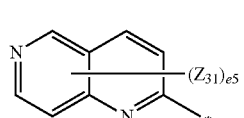
Formula 5-26
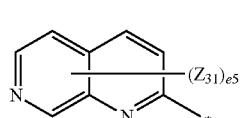
Formula 5-27
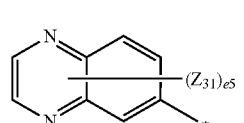
Formula 5-28
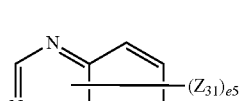
Formula 5-29
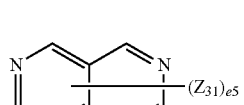
Formula 5-30
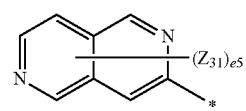
Formula 5-31
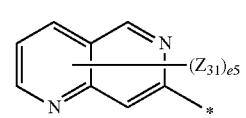
Formula 5-32
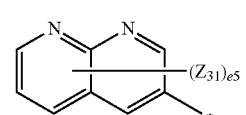
Formula 5-33
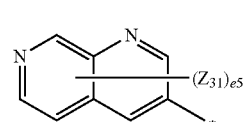
Formula 5-34
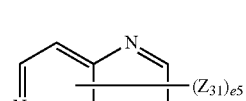
Formula 5-35
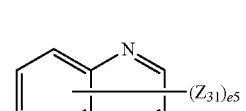
Formula 5-36
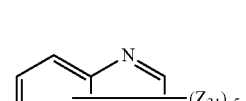
Formula 5-37
Formula 5-38
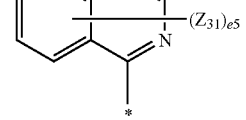
Formula 5-39
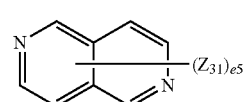
Formula 5-40

-continued

Formula 5-41
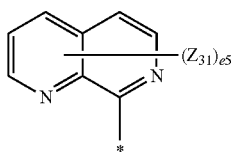

Formula 5-42
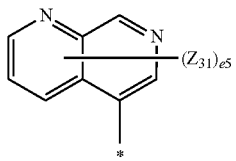

Formula 5-43
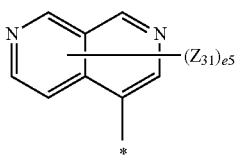

Formula 5-44
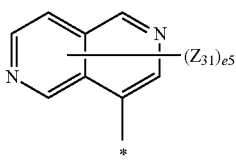

Formula 5-45
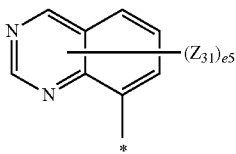

Formula 5-46
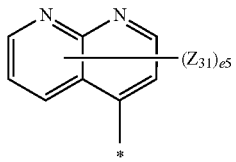

Formula 5-47
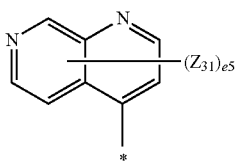

Formula 5-48
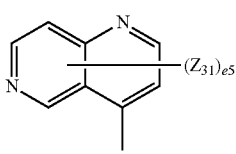

Formula 5-49
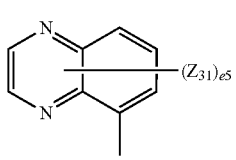

Formula 5-50
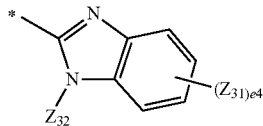

Formula 5-51
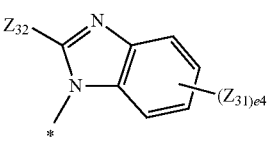

Formula 5-52
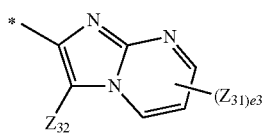

Formula 5-53
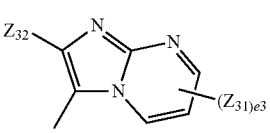

Formula 5-54
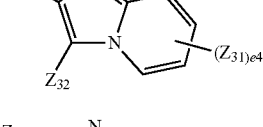

Formula 5-55
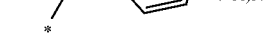

wherein, in Formulae 5-1 to 5-55, $Z_{31}$ to $Z_{33}$ are each independently selected from hydrogen, deuterium, —$CD_3$, —$CD_2H$, —$CDH_2$, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a biphenyl group, and a terphenyl group, e2 is an integer selected from 0 to 2, e3 is an integer selected from 0 to 3, e4 is an integer selected from 0 to 4, and

* indicates a binding site to a neighboring atom.

8. The condensed cyclic compound of claim 1, wherein $R_1$ to $R_8$, $R_{12}$ to $R_{15}$, $R_{20}$ to $R_{24}$, and $R_{31}$ to $R_{33}$ are each independently selected from:

hydrogen, deuterium, a cyano group, a $C_1$-$C_{10}$ alkyl group, a $C_1$-$C_{10}$ alkoxy group, a phenyl group, a biphenyl group, a terphenyl group and a pyridinyl group;

a $C_1$-$C_{10}$ alkyl group and a $C_1$-$C_{10}$ alkoxy group, each substituted with at least one of deuterium and a cyano group; and a phenyl group, a biphenyl group, a terphenyl group, and a pyridinyl group, each substituted with at least one selected from deuterium, a cyano group, a $C_1$-$C_{10}$ alkyl group, a $C_1$-$C_{10}$ alkoxy group, a phenyl group, a biphenyl group, a terphenyl group, and a pyridinyl group.

9. The condensed cyclic compound of claim 1, wherein at least one of $X_3$ and $X_6$ in Formulae 1-1A, 1-1C to 1-1D, 1-2A to 1-2D and 1-3A to 1-3D is C(CN) or N.

10. The condensed cyclic compound of claim 1, wherein $L_1$ and $L_2$ are each independently selected from:

a phenylene group, a fluorenylene group, a spiro-bifluorenylene group, a pyridinylene group, a carbazolylene group, a dibenzofuranylene group, and a dibenzothiophenylene group; and a phenylene group, a fluorenylene group, a spiro-bifluorenylene group, a pyridinylene group, a carbazolylene group, a dibenzofuranylene group, and a dibenzothiophenylene group, each substituted with at least one selected from deuterium, a cyano group, a $C_1$-$C_{10}$ alkyl group, a phenyl group, a biphenyl group, and a terphenyl group.

11. The condensed cyclic compound of claim 1, wherein $L_1$ and $L_2$ are each independently selected from groups represented by Formulae 3-1 to 3-15:

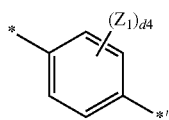
Formula 3-1

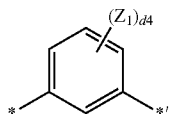
Formula 3-2

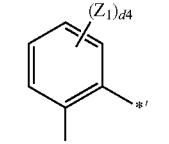
Formula 3-3

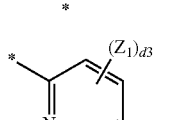
Formula 3-4

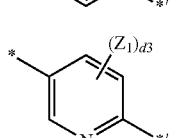
Formula 3-5

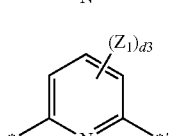
Formula 3-6

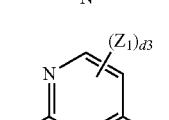
Formula 3-7

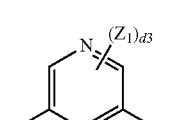
Formula 3-8

-continued

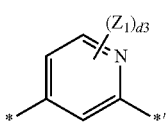
Formula 3-9

Formula 3-10

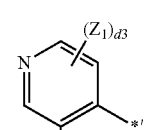
Formula 3-11

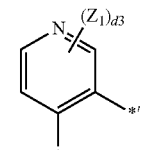
Formula 3-12

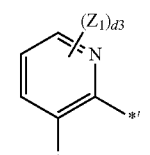
Formula 3-13

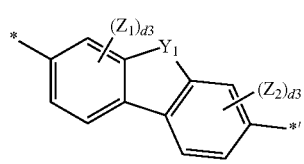
Formula 3-14

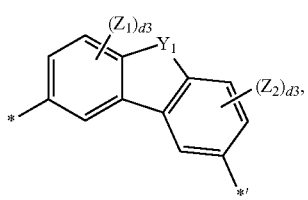
Formula 3-15 wherein, in Formulae 3-1 to 3-15, $Y_1$ is O, S, $N(Z_3)$, $C(Z_4)(Z_5)$, or $Si(Z_4)(Z_5)$, $Z_1$ to $Z_5$ are each independently selected from hydrogen, deuterium, a cyano group, a $C_1$-$C_{10}$ alkyl group, a phenyl group, a biphenyl group, and a terphenyl group, d3 is an integer selected from 0 to 3, d4 is an integer selected from 0 to 4, and

* and *' each indicate a binding site to a neighboring atom.

12. The condensed cyclic compound of claim 1, wherein, in the condensed cyclic compound represented by Formulae 1-1A, 1-1C to 1-1D, 1-2A to 1-2D and 1-3A to 1-3D, the number of cyano group(s) is 0, 1, 2, 3, or 4.

13. An organic light-emitting device comprising:
a first electrode;
second electrode; and
an organic layer disposed between the first electrode and the second electrode, wherein the organic layer comprises an emission layer, and wherein the organic layer comprises at least one condensed cyclic compound represented by one of Formulae 1-1A, 1-1C to 1-1D, 1-2A to 1-2D, and 1-3A to 1-3D of claim 1.

14. The organic light-emitting device of claim 13, wherein the first electrode is an anode, the second electrode is a cathode, and the organic layer comprises a hole transport region disposed between the first electrode and the emission layer and an electron transport region disposed between the emission layer and the second electrode, wherein the hole transport region comprises a hole injection layer, a hole transport layer, an electron blocking layer, or a combination thereof, and the electron transport region comprises a hole blocking layer, an electron transport layer, an electron injection layer, or a combination thereof.

15. The organic light-emitting device of claim 14, wherein the hole transport region comprises the hole transport layer, and the hole transport layer comprises the condensed cyclic compound represented by one of Formulae 1-1A, 1-1C to 1-1D, 1-2A to 1-2D, and 1-3A to 1-3D.

16. The organic light-emitting device of claim 14, wherein the hole transport region comprises the electron blocking layer, and the electron blocking layer comprises the condensed cyclic compound represented by one of Formulae 1-1A, 1-1C to 1-1D, 1-2A to 1-2D, and 1-3A to 1-3D.

17. The organic light-emitting device of claim 13, wherein the emission layer comprises the condensed cyclic compound represented by one of Formulae 1-1A, 1-1C to 1-1D, 1-2A to 1-2D, and 1-3A to 1-3D.

18. A condensed compound represented by Formula 1-1B

Formula 1-1B

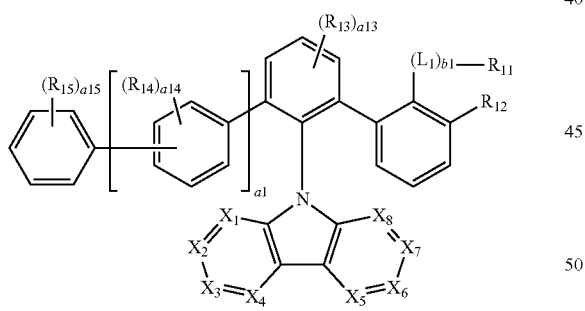

Formula 2-1

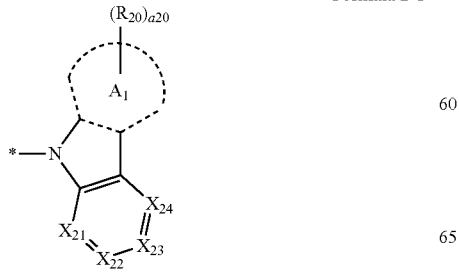

Formula 2-2

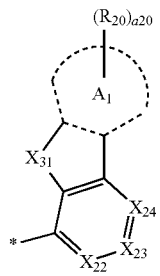

Formula 2-3

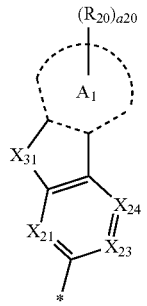

Formula 2-4

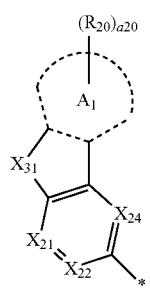

Formula 2-5

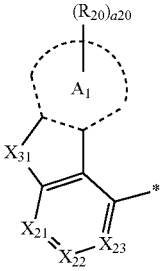

wherein, in Formula 1-1B, $X_1$ is N or $C(R_1)$, $X_2$ is N or $C(R_2)$, $X_3$ is N or $C(R_3)$, $X_4$ is N or $C(R_4)$, $X_5$ is N or $C(R_5)$, $X_6$ is N or $C(R_6)$, $X_7$ is N or $C(R_7)$, and $X_8$ is N or $C(R_8)$, wherein at least one selected from $X_1$ to $X_8$ is not N, in Formula 1-1B, a1 is an integer selected from 0 to 3, in Formulae 2-1 to 2-5, $X_{21}$ is N or $C(R_{21})$, $X_{22}$ is N or $C(R_{22})$, $X_{23}$ is N or $C(R_{23})$, and $X_{24}$ is N or $C(R_{24})$, wherein at least one selected from $X_{21}$ to $X_{24}$ in Formulae 2-1 is not N, in Formulae 2-1 to 2-5, ring $A_1$ is a benzene group, a pyridine group, a pyrimidine group, a pyridazine group, a pyrazine group, a triazine group, a fluorene group, a carbazole group, a dibenzofuran group, a dibenzothiophene group, a dibenzosilol group, an azafluorene group, an azacarbazole group, an azadibenzofuran group, an azadibenzothiophene group, or an azadibenzosilol group, in Formulae 2-2 to 2-5, $X_{31}$ is O, S, $N(R_{31})$, $C(R_{32})(R_{33})$, or $Si(R_{32})(R_{33})$, in Formulae 2-2 to 2-5, $X_{31}$ is $N(R_{31})$, or ring $A_1$ is a carbazole group or an azacarbazole group, in Formula 1-1B, $R_{11}$ is selected from:
- a group represented by one selected from Formulae 2-1 to 2-5;
- an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an indazolyl group, a quinolinyl group, an isoquinolinyl group, a benzoquinolinyl group, a phthalazinyl group, a naphthyridinyl group, a quinoxalinyl group, a quinazolinyl group, a cinnolinyl group, a phenanthridinyl group, an acridinyl group, a phenanthrolinyl group, a phenazinyl group, a benzimidazolyl group, an isobenzothiazolyl group, a benzoxazolyl group, an isobenzoxazolyl group, a triazolyl group, a tetrazolyl group, an oxadiazolyl group, a triazinyl group, a thiadiazolyl group, an imidazopyridinyl group, and an imidazopyrimidinyl group; and
- an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an indazolyl group, a quinolinyl group, an isoquinolinyl group, a benzoquinolinyl group, a phthalazinyl group, a naphthyridinyl group, a quinoxalinyl group, a quinazolinyl group, a cinnolinyl group, a phenanthridinyl group, an acridinyl group, a phenanthrolinyl group, a phenazinyl group, a benzimidazolyl group, an isobenzothiazolyl group, a benzoxazolyl group, an isobenzoxazolyl group, a triazolyl group, a tetrazolyl group, an oxadiazolyl group, a triazinyl group, a thiadiazolyl group, an imidazopyridinyl group, and an imidazopyrimidinyl group, each substituted with at least one selected from deuterium, —$CD_3$, —$CD_2H$, —$CDH_2$, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, a biphenyl group, and a terphenyl group, provided that, when $R_{11}$ in Formula 1-1B is a group represented by Formula 2-1, at least one of $X_{21}$ to $X_{24}$ in Formula 2-1 is N, in Formulae 1-1B when a1 is 0, the phenyl group substituted with $(R_{15})_{a15}$ is attached to the phenyl group substituted with $(R_{13})_{a13}$ and when b1 is 0, then $R_{11}$ is attached to the phenyl group substituted with $(R_{13})_{a13}$, in Formula 1-1B, $R_{12}$ is selected from deuterium, —F, —Cl, —Br, —I, a hydroxyl group, a nitro group, an amino group, an amidino group, a hydrazine group, a hydrazone group, a carboxylic acid group or a salt thereof, a sulfonic acid group or a salt thereof, a phosphoric acid group or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted alkoxy group, a substituted or unsubstituted $C_3$-$C_{10}$ cycloalkyl group, a substituted or unsubstituted heterocycloalkyl group, a substituted or unsubstituted $C_3$-$C_{10}$ cycloalkenyl group, a substituted or unsubstituted heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, a substituted or unsubstituted monovalent non-aromatic condensed heteropolycyclic group, —$Si(Q_1)(Q_2)(Q_3)$, —$N(Q_4)(Q_5)$, and —$B(Q_6)(Q_7)$, wherein $R_{12}$ does not include a cyano group, in Formulae 1-1B and 2-1 to 2-5, $R_1$ to $R_8$, $R_{13}$ to $R_{15}$, $R_{20}$ to $R_{24}$, and $R_{31}$ to $R_{33}$ are each independently selected from:
- hydrogen, deuterium, a cyano group, a $C_1$-$C_{20}$ alkyl group, a $C_1$-$C_{20}$ alkoxy group, a phenyl group, a biphenyl group, a terphenyl group, a naphthyl group, a fluorenyl group, a pyridinyl group, a pyrimidinyl group, a pyrazinyl group, a pyridazinyl group, a triazinyl group, a dibenzofuranyl group, a dibenzothiophenyl group, and a dibenzosilolyl group;
- a $C_1$-$C_{20}$ alkyl group and a $C_1$-$C_{20}$ alkoxy group, each substituted with at least one of deuterium and a cyano group; and
- a phenyl group, a biphenyl group, a terphenyl group, a naphthyl group, a fluorenyl group, a pyridinyl group, a pyrimidinyl group, a pyrazinyl group, a pyridazinyl group, a triazinyl group, a dibenzofuranyl group, a dibenzothiophenyl group, and a dibenzosilolyl group, each substituted with at least one selected from deuterium, a cyano group, a $C_1$-$C_{20}$ alkyl group, a $C_1$-$C_{20}$ alkoxy group, a phenyl group, a biphenyl group, a terphenyl group, a naphthyl group, a fluorenyl group, a pyridinyl group, a pyrimidinyl group, a pyrazinyl group, a pyridazinyl group, a triazinyl group, a dibenzofuranyl group, a dibenzothiophenyl group, and a dibenzosilolyl group, wherein $R_{13}$ does not include a cyano group, in Formula 1-1B, a13 is an integer selected from 0 to 3, wherein, when a13 is 2 or more, 2 or more groups $R_{13}$ are identical to or different from each other, in Formula 1-1B, a14 is an integer selected from 0 to 4, wherein, when a14 is 2 or more, 2 or more groups $R_{14}$ are identical to or different from each other, in Formula 1-1B, a15 is an integer selected from 0 to 5, wherein, when a15 is 2 or more, 2 or more groups $R_{15}$ are identical to or different from each other, in Formulae 2-1 to 2-5, a20 is an integer selected from 0 to 8, wherein, when a20 is 2 or more, 2 or more groups $R_{20}$ are identical to or different from each other, in Formula 1-1B, $L_1$ is selected from a substituted or unsubstituted $C_3$-$C_{10}$ cycloalkylene group, a substituted or unsubstituted $C_1$-$C_{10}$ heterocycloalkylene group, a substituted or unsubstituted $C_3$-$C_{10}$ cycloalkenylene group, a substituted or unsubstituted $C_1$-$C_{10}$ heterocycloalkenylene group, a substituted or unsubstituted $C_6$-$C_{60}$ arylene group, a substituted or unsubstituted $C_1$-$C_{60}$ heteroarylene group, a substituted or unsubstituted divalent non-aromatic condensed polycyclic group, and a substituted or unsubstituted divalent non-aromatic condensed heteropolycyclic group, wherein $L_2$ does not include a cyano group, in Formula 1-1B, b1 is an integer selected from 0 to 5, wherein, when b1 is 2 or more, 2 or more groups $L_1(s)$ are identical to or different from each other, and when b2 is 2 or more, 2 or more groups $L_2$ are identical to or different from each other, in the condensed cyclic compound represented by Formula 1-1B, the number of carbazole ring(s) is 0, 1, or 2, the condensed cyclic compound represented by Formula 1-1B has an asymmetrical structure, in Formulae 2-1 to 2-5, * indicates a binding site to a neighboring atom, at least one substituent selected from substituent(s) of the substituted $C_3$-$C_{10}$ cycloalkylene group, the substituted $C_1$-$C_{10}$ heterocycloalkylene group, the substituted $C_3$-$C_{10}$ cycloalkenylene group, the substituted $C_1$-$C_{10}$ heterocycloalkenylene group, the substituted $C_6$-$C_{60}$ arylene group, the substituted $C_1$-$C_{60}$ heteroarylene group, the substituted divalent non-aromatic condensed polycyclic group, the substituted divalent non-aromatic condensed heteropolycyclic group, the substituted $C_1$-$C_{60}$ alkyl group, the substituted $C_2$-$C_{60}$ alkenyl group, the substituted $C_2$-$C_{60}$ alkynyl group, the substituted $C_3$-$C_{10}$ cycloalkyl group, the substituted $C_1$-$C_{10}$ heterocycloalkyl group, the substituted $C_3$-$C_{10}$ cycloalkenyl group, the substituted $C_1$-$C_{10}$ heterocycloalkenyl group, the substituted $C_6$-$C_{60}$ aryl group, the substituted $C_6$-$C_{60}$ aryloxy group, the substituted $C_6$-$C_{60}$ arylthio group, the substituted $C_1$-$C_{60}$ heteroaryl group, the substituted monovalent non-aromatic condensed polycyclic group, and the substituted monovalent non-aromatic condensed heteropolycyclic group is selected from:

deuterium, —F, —Cl, —Br, —I, —CD$_3$, —CD$_2$H, —CDH$_2$, —CF$_3$, —CF$_2$H, —CFH$_2$, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, and $C_1$-$C_{60}$ alkoxy group;

a $C_1$-$C_{60}$ alkyl group, a $C_2$-$C_{60}$ alkenyl group, a $C_2$-$C_{60}$ alkynyl group, and a $C_1$-$C_{60}$ alkoxy group, each substituted with at least one selected from deuterium, —F, —Cl, —Br, —I, —CD$_3$, —CD$_2$H, —CDH$_2$, —CF$_3$, —CF$_2$H, —CFH$_2$, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —Si(Q$_{11}$)(Q$_{12}$)(Q$_{13}$), —N(Q$_{14}$)(Q$_{15}$), and —B(Q$_{16}$)(Q$_{17}$);

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group;

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group, each substituted with at least one selected from deuterium, —F, —Cl, —Br, —I, —CD$_3$, —CD$_2$H, —CDH$_2$, —CF$_3$, —CF$_2$H, —CFH$_2$, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —Si(Q$_{21}$)(Q$_{22}$)(Q$_{23}$), —N(Q$_{24}$)(Q$_{25}$), and —B(Q$_{26}$)(Q$_{27}$); and —Si(Q$_{31}$)(Q$_{32}$)(Q$_{33}$), —N(Q$_{34}$)(Q$_{35}$), and —B(Q$_{36}$)(Q$_{37}$), and $Q_1$ to $Q_7$, $Q_{11}$ to $Q_{17}$, $Q_{21}$ to $Q_{27}$, and $Q_{31}$ to $Q_{37}$ are each independently selected from hydrogen, deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, and a substituted or unsubstituted monovalent non-aromatic condensed heteropolycyclic group.

19. A condensed cyclic compound being one selected from Compounds 1 to 135:

-continued
1
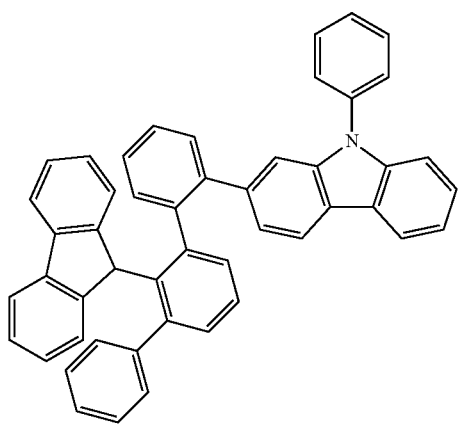
2
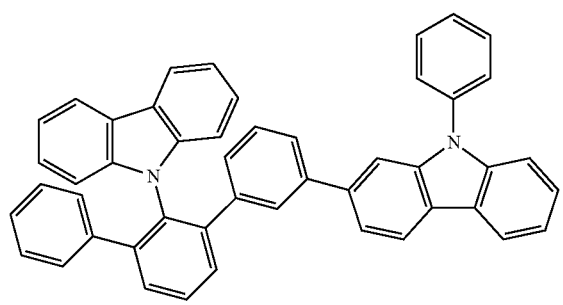
3
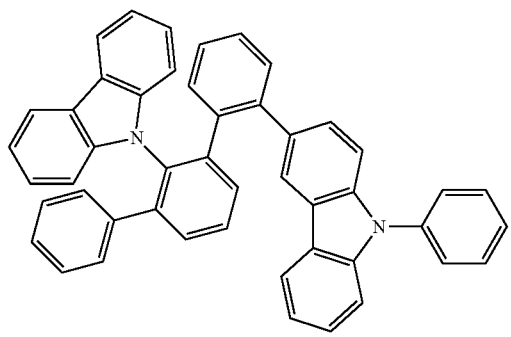
4
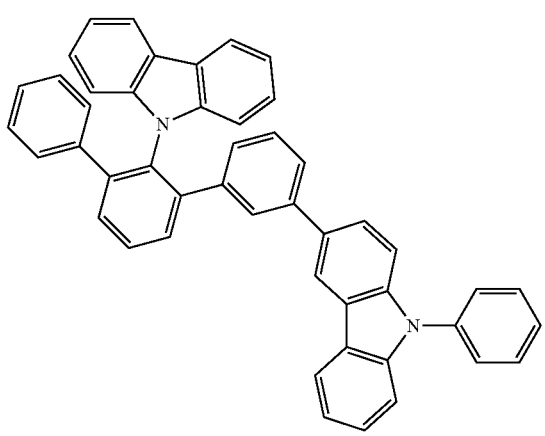
5
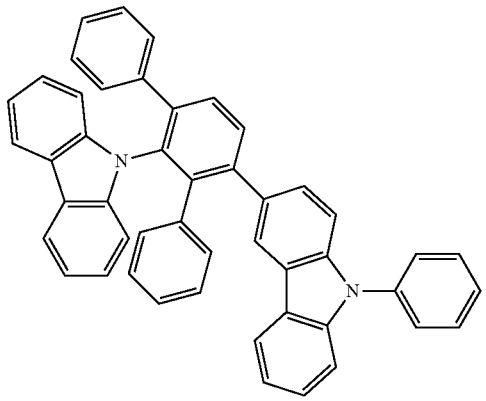
6
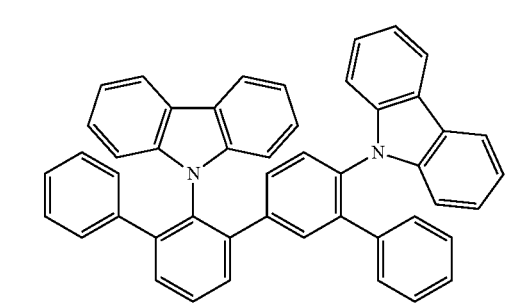
7
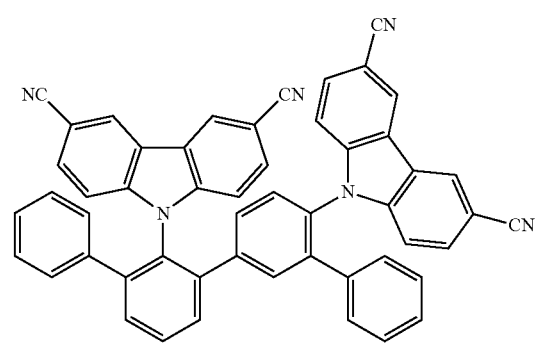
8

9
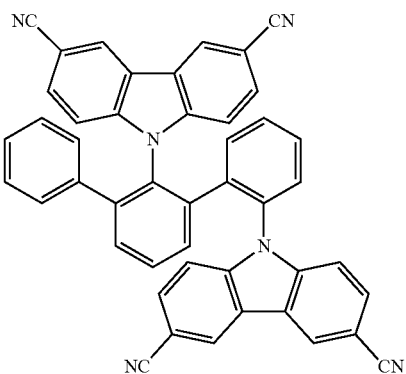
10
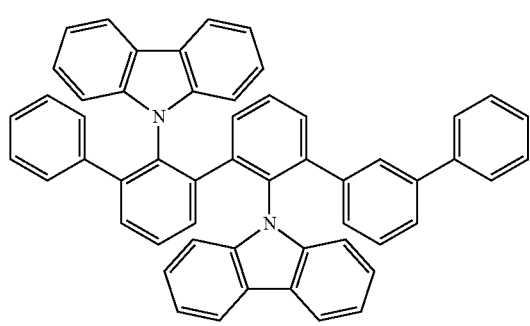
11
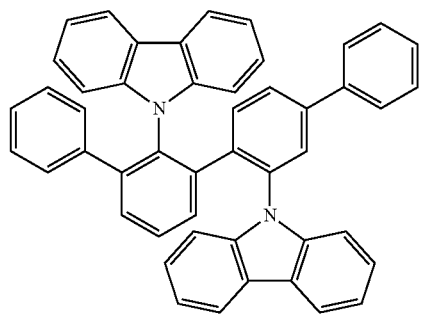
12
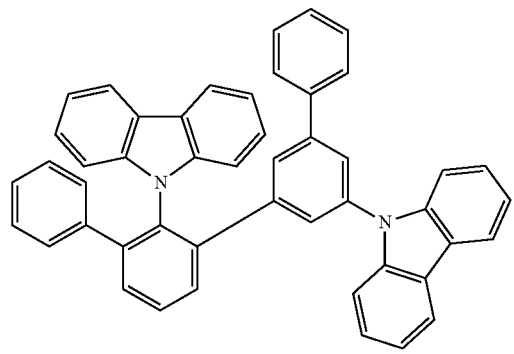
13
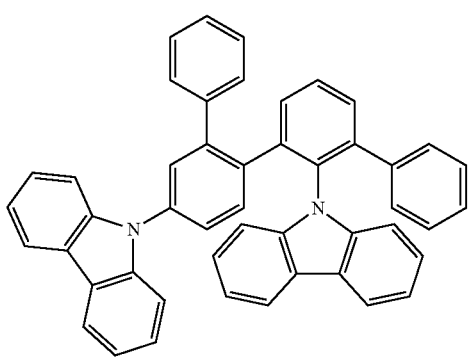
14
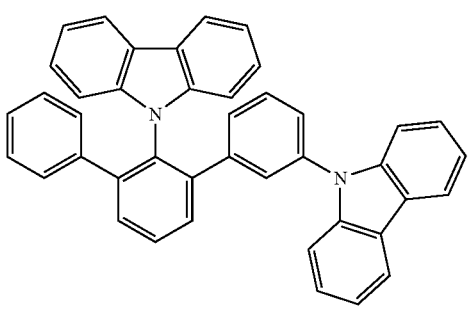
15
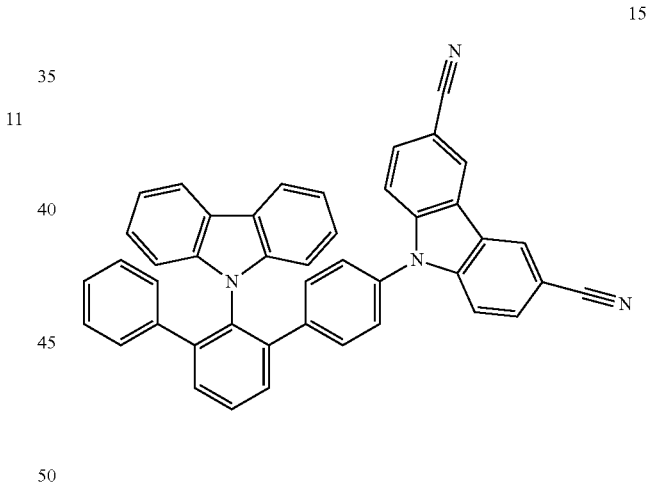
16
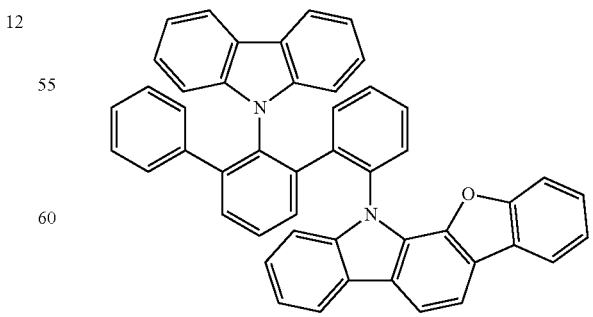

17
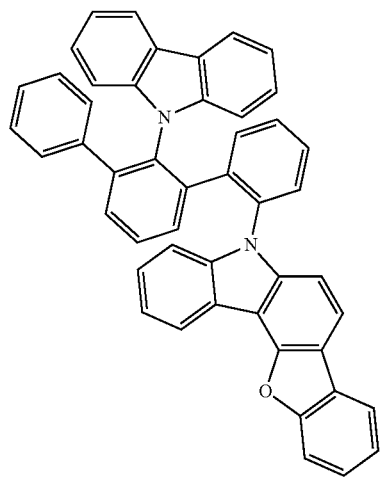
18
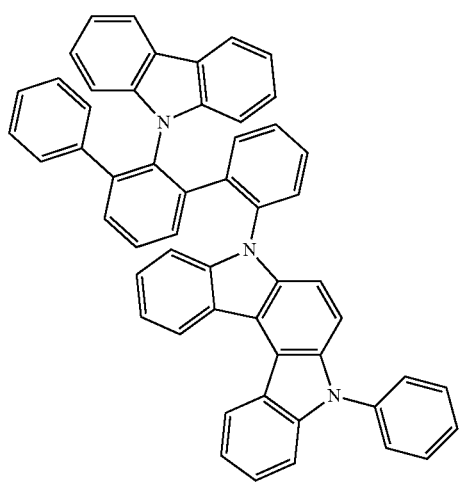
19
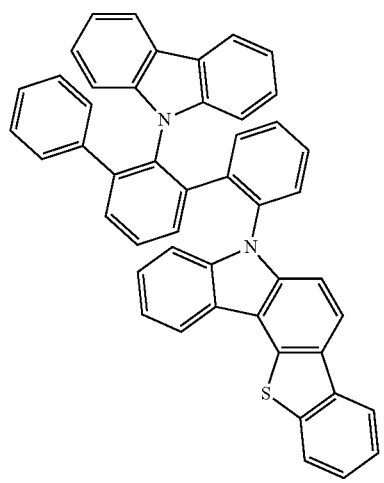
20
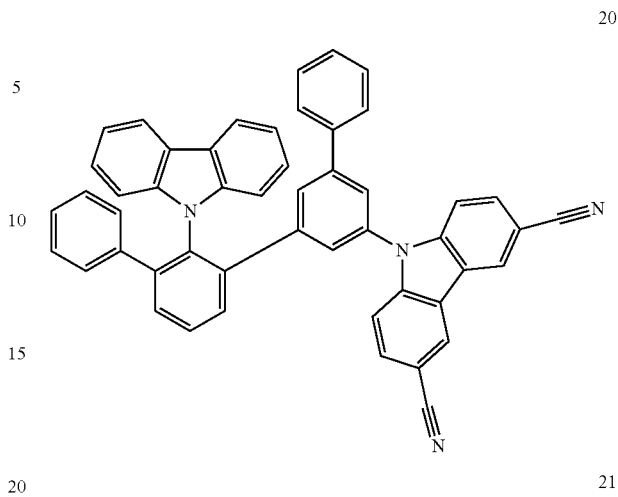
21
22
23

24
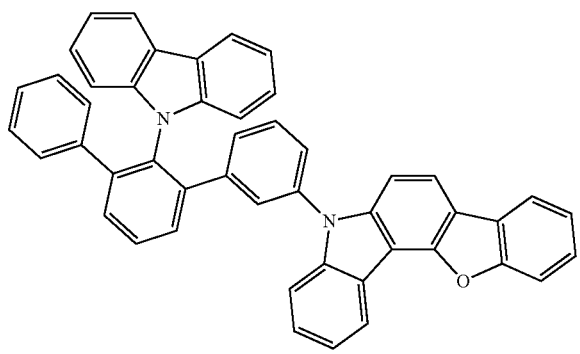
25
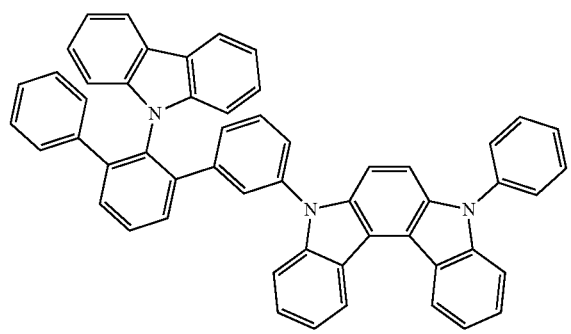
26
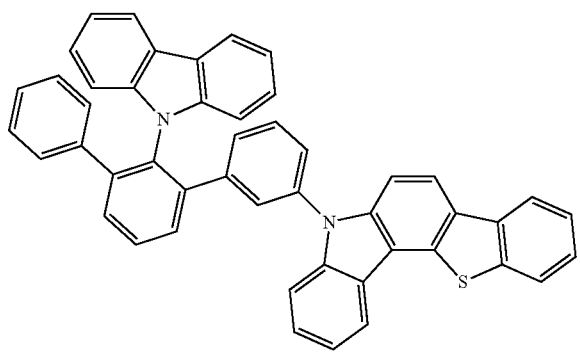
27
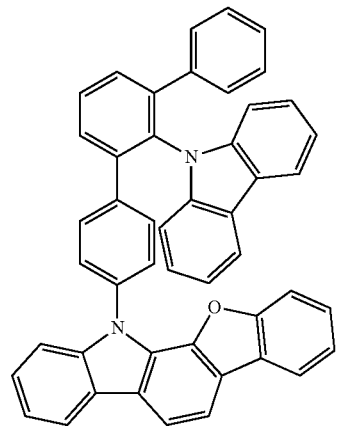
28
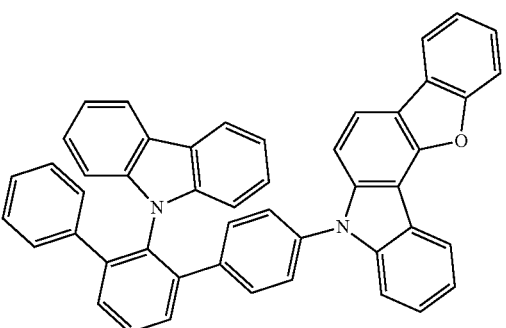
29
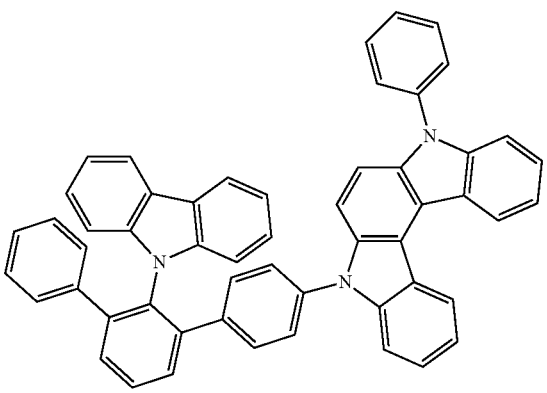
30
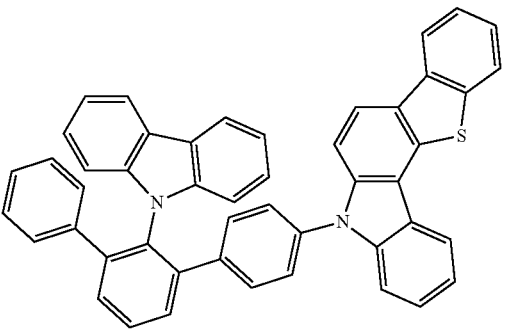
31
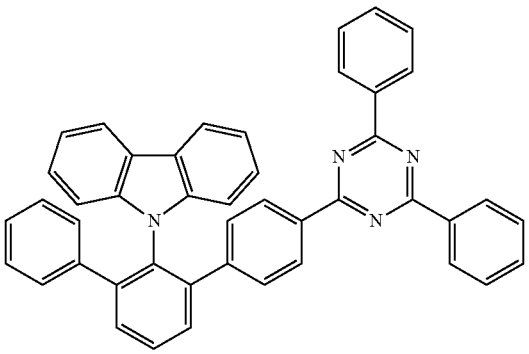

32
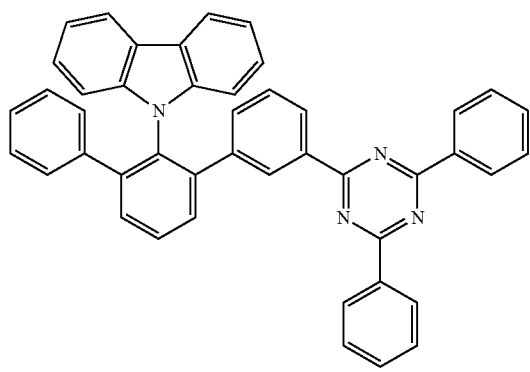
33
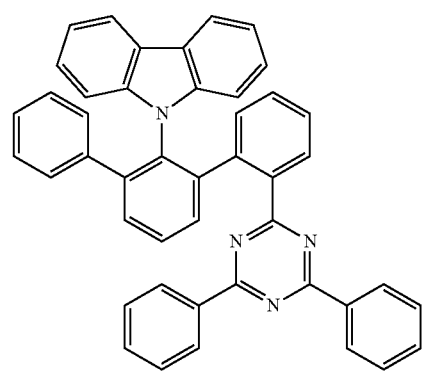
34
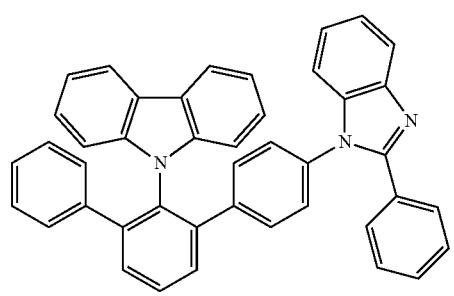
35
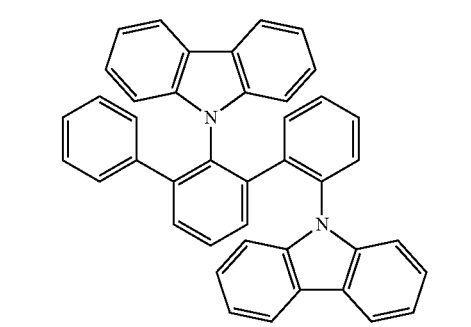
36
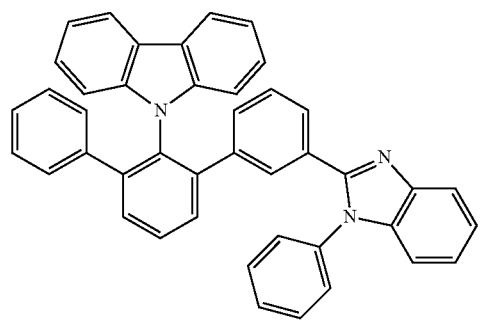
37
38
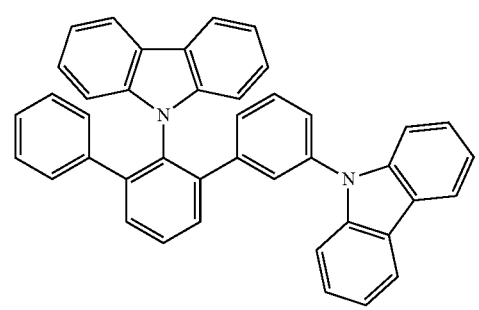
39

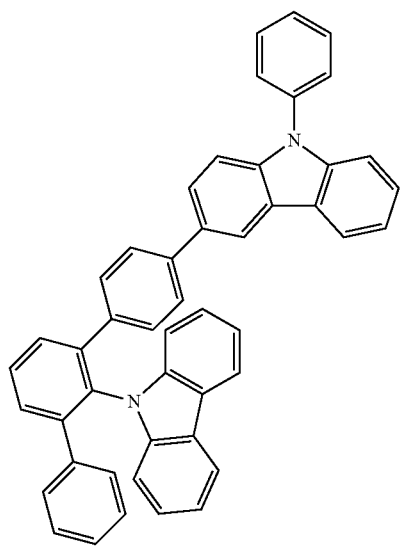
40
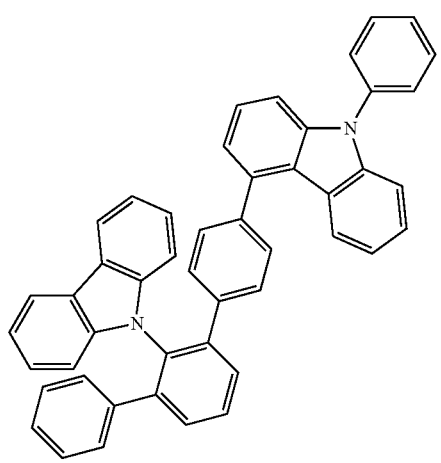
41
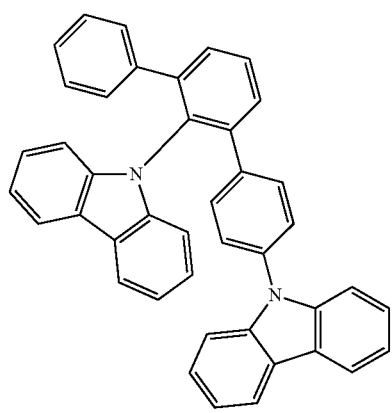
42
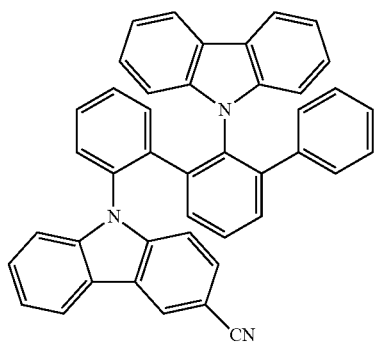
43
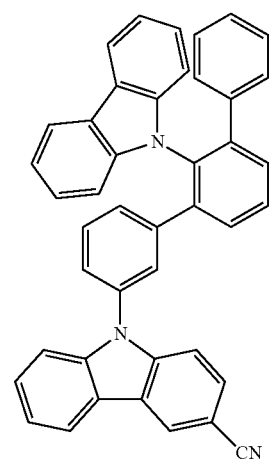
44
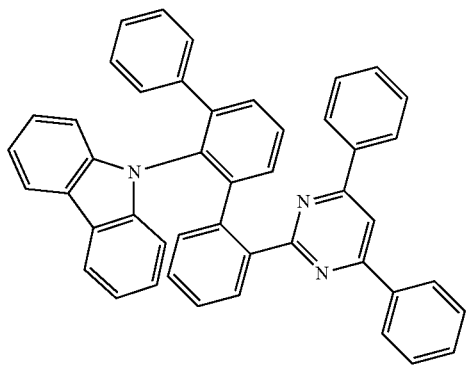
45

46
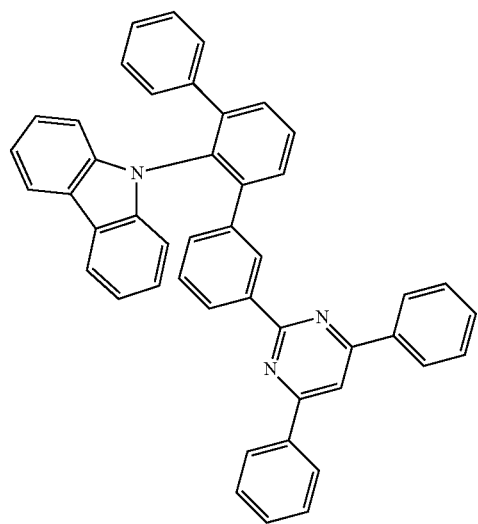
47
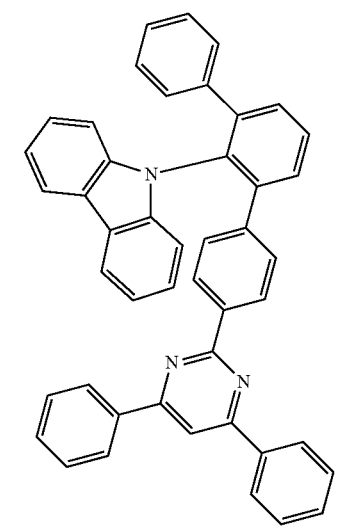
48
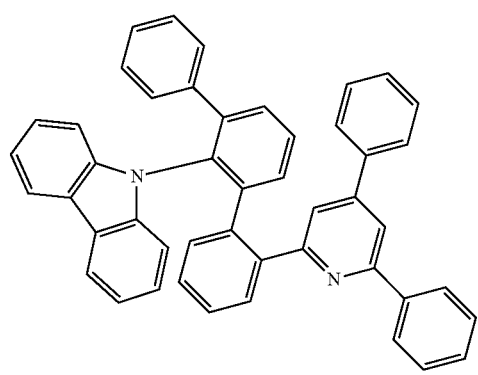
49
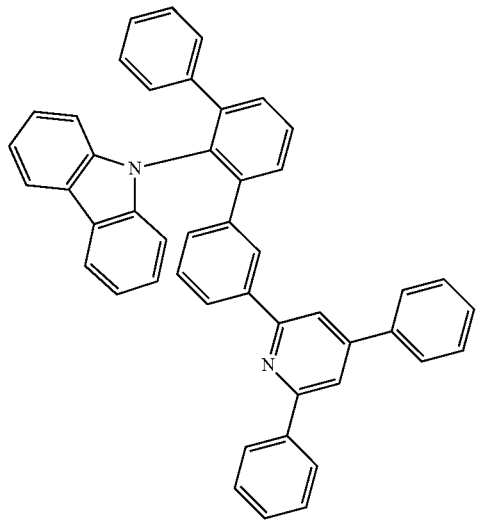
50
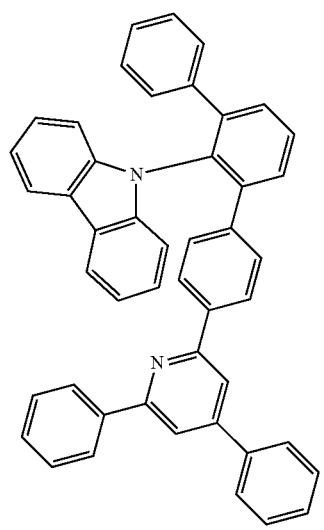
51
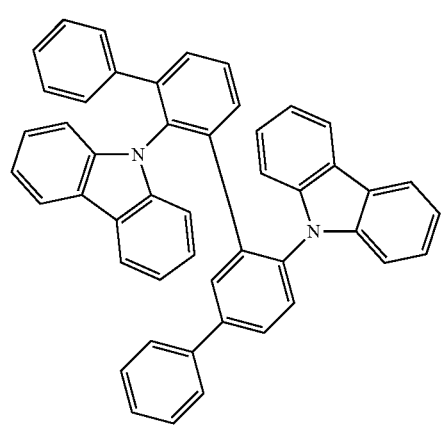

52
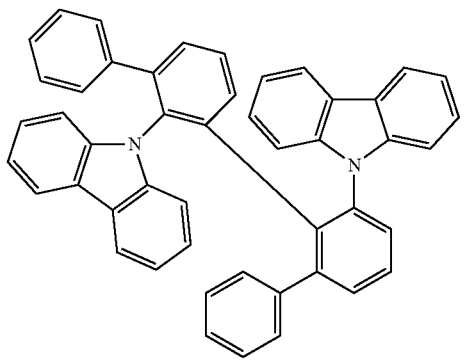
53
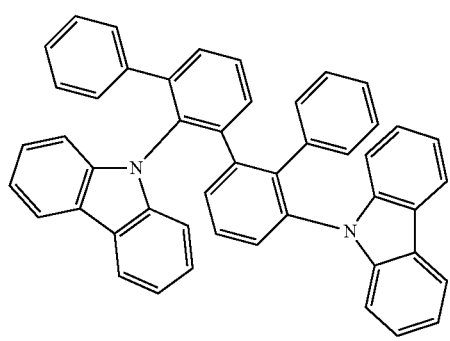
54
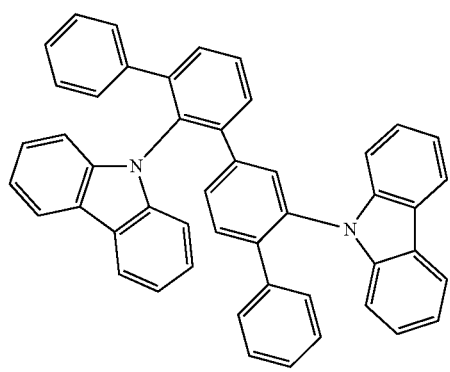
55
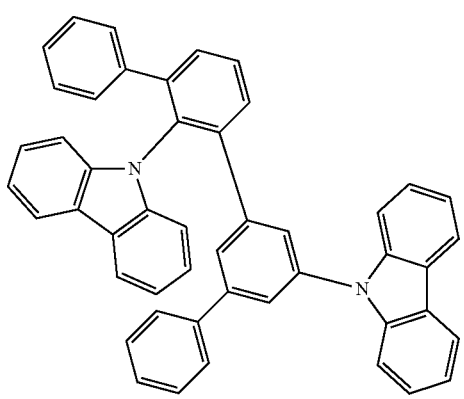
56
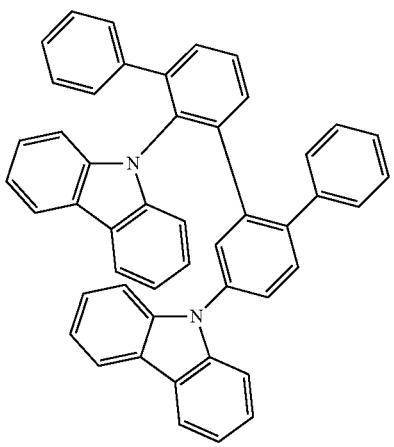
57
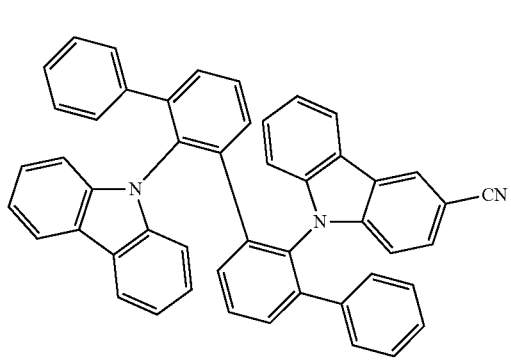
58
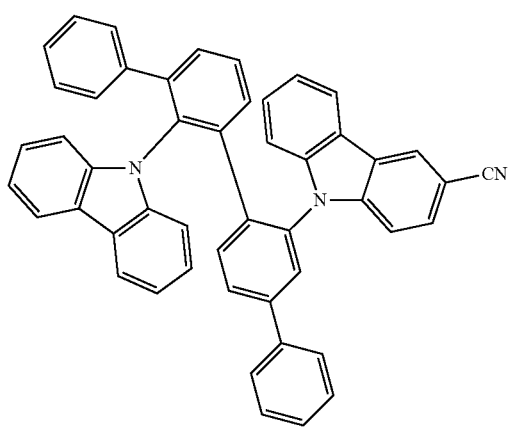
59
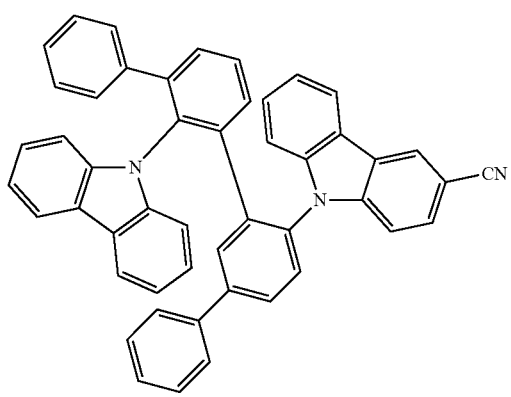

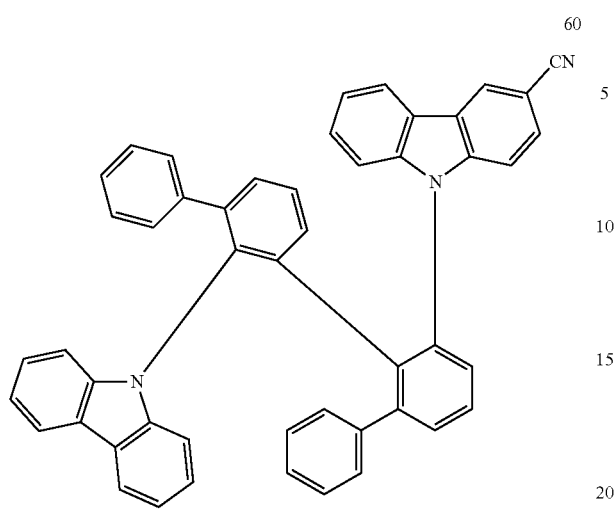
60
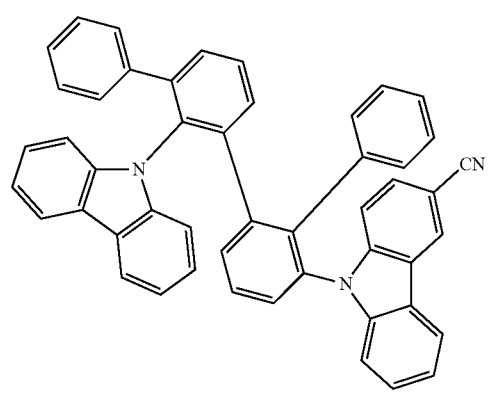
61
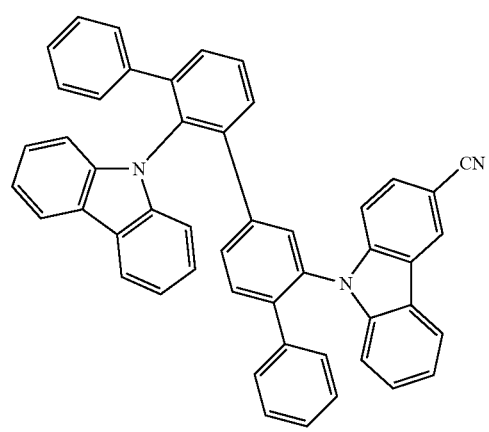
62
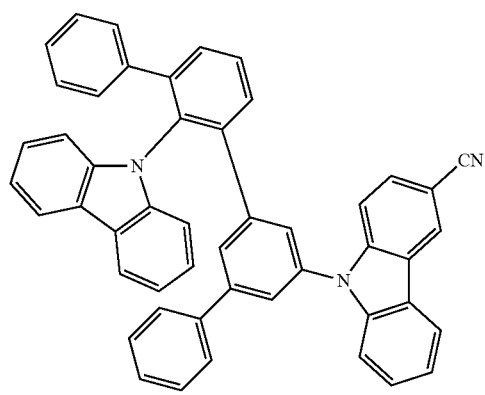
63
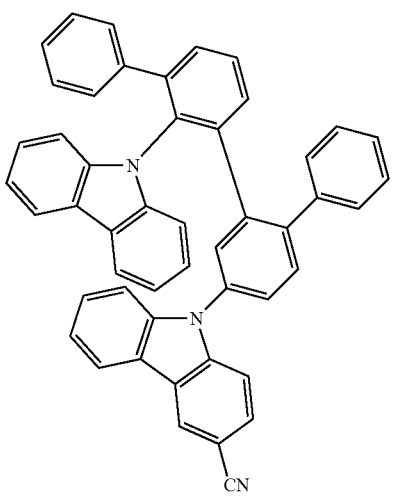
64
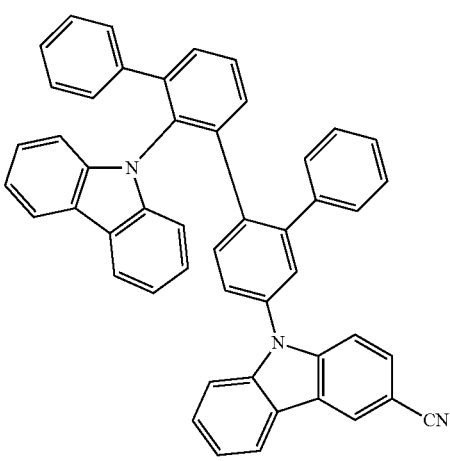
65

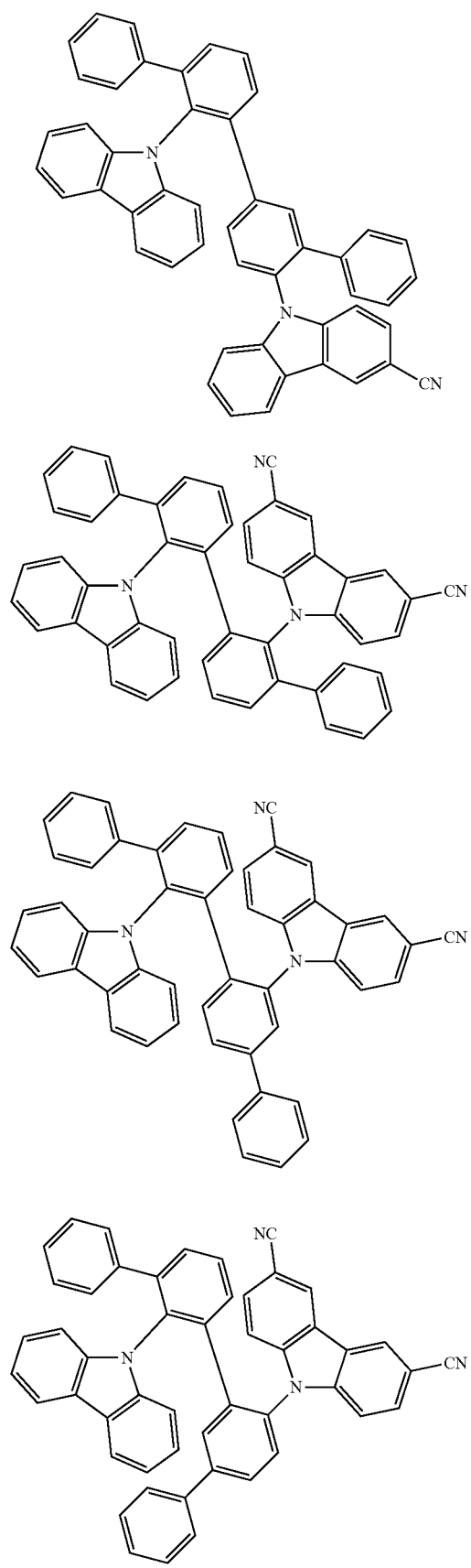
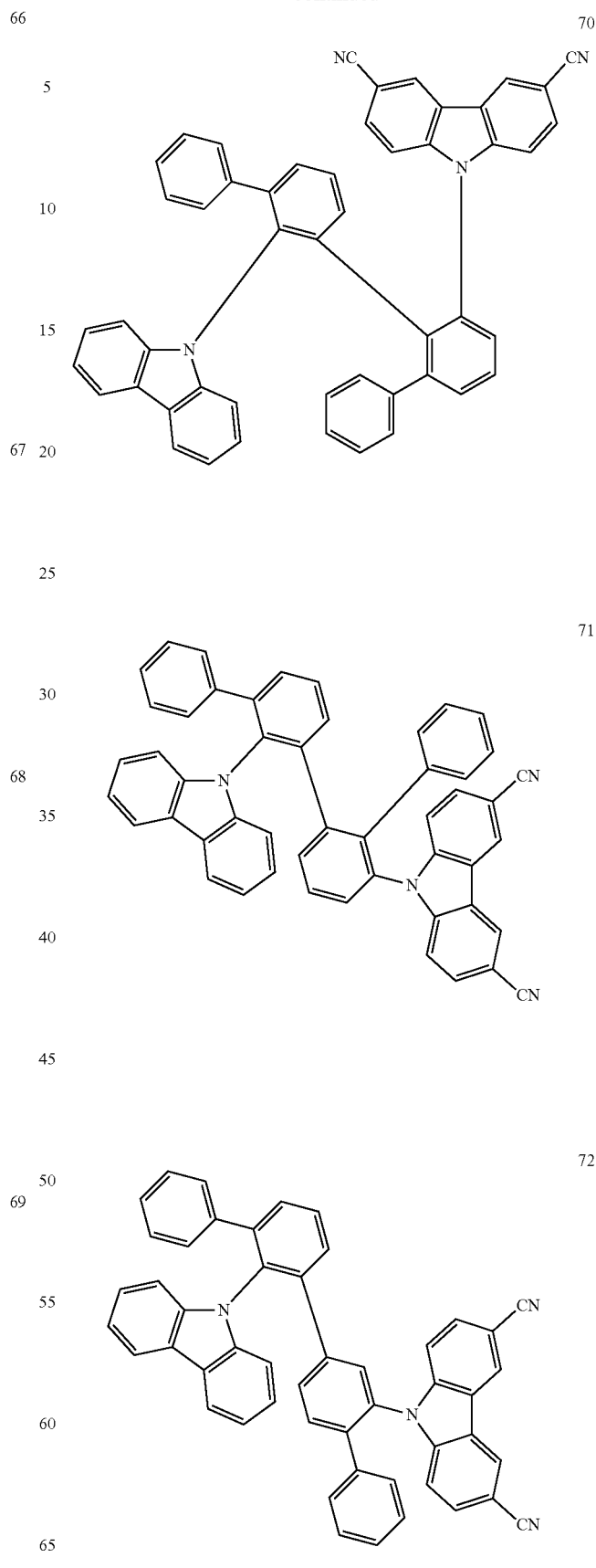

169
-continued
73
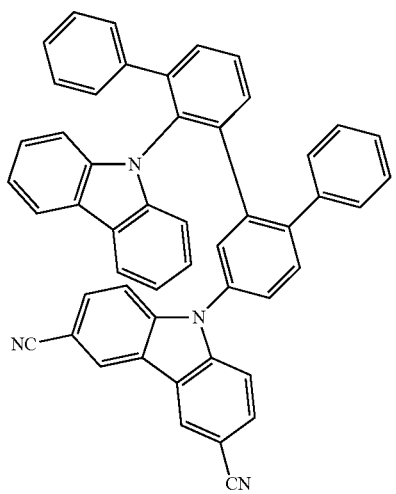
74
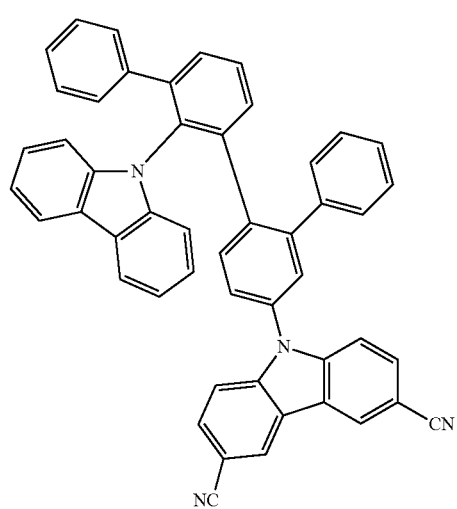
75
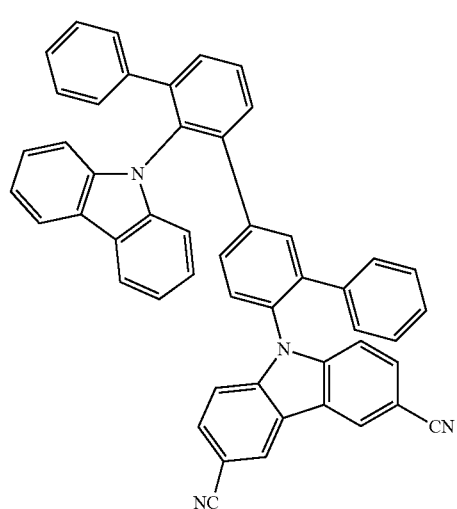
170
-continued
76
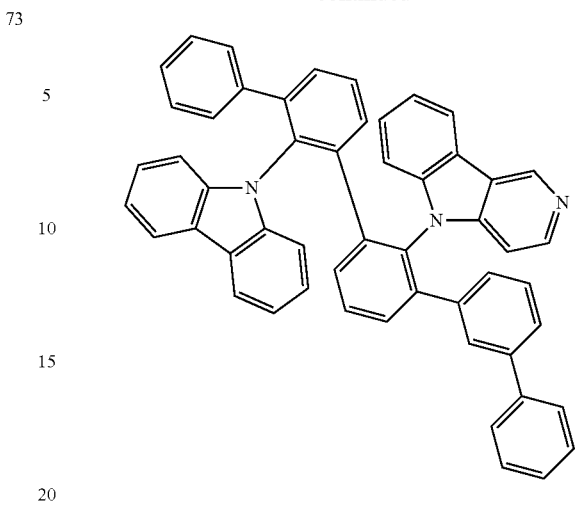
77
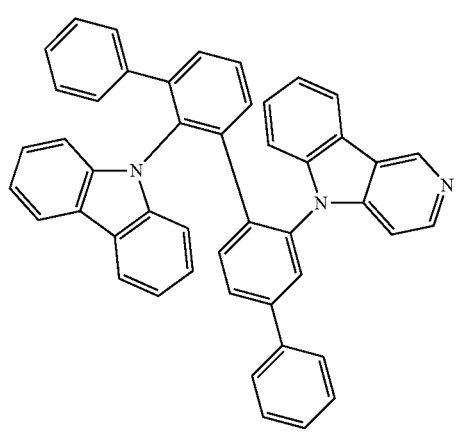
78
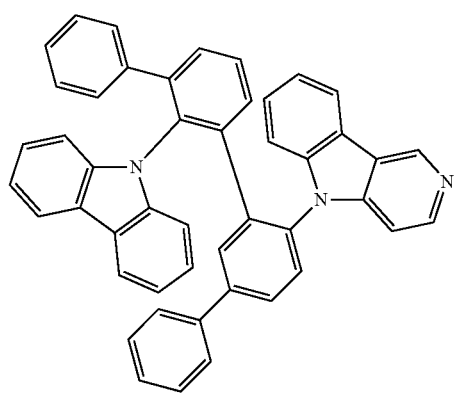

79
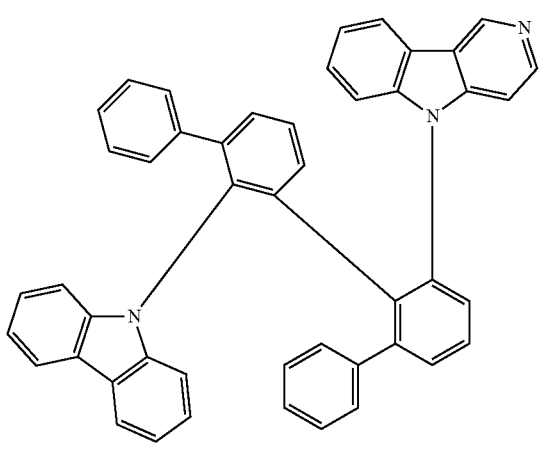
80
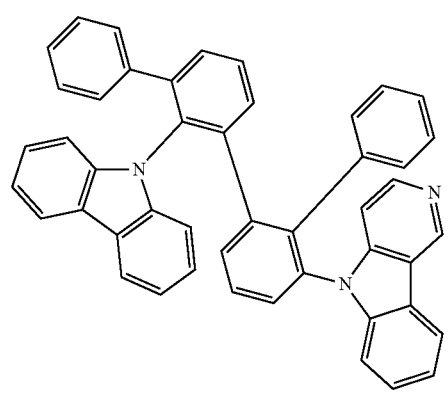
81
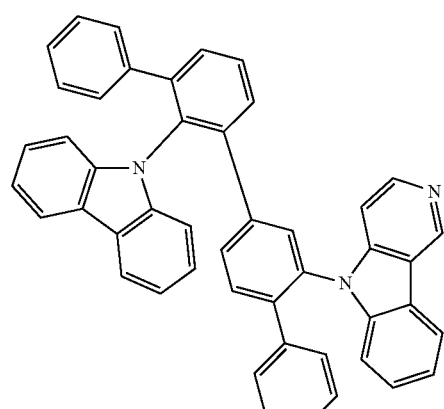
82
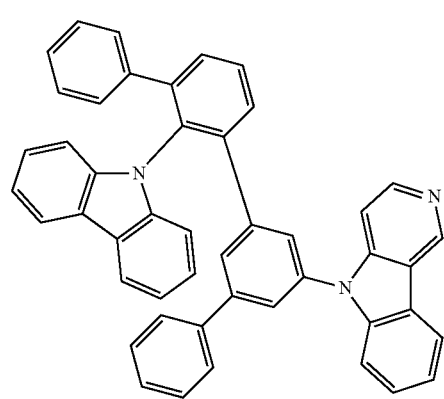
83
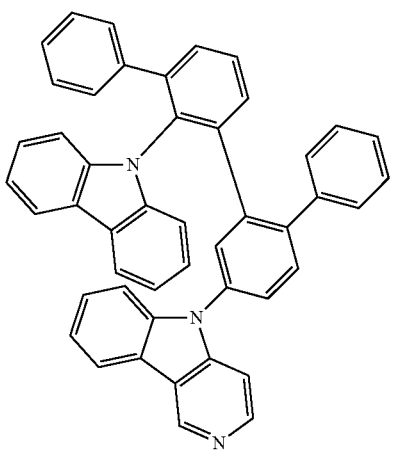
84
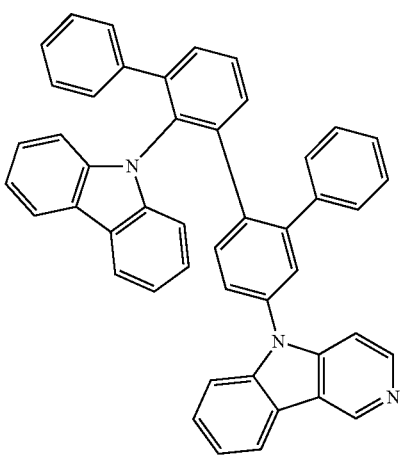
85
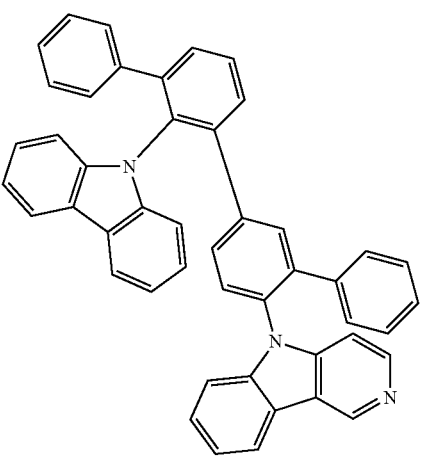

86
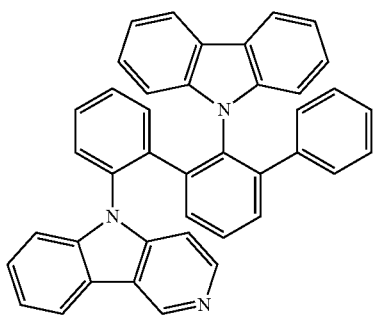
87
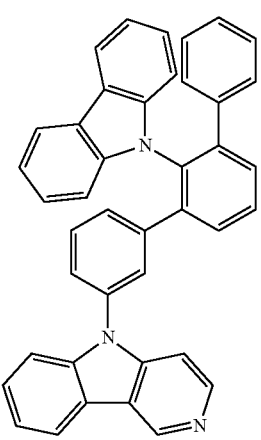
88
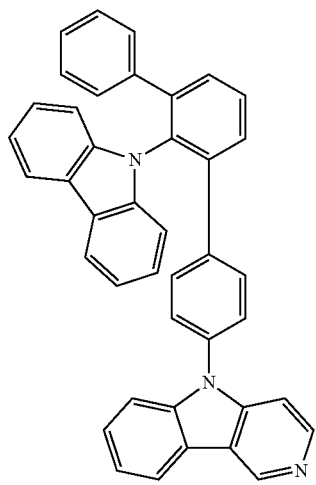
89
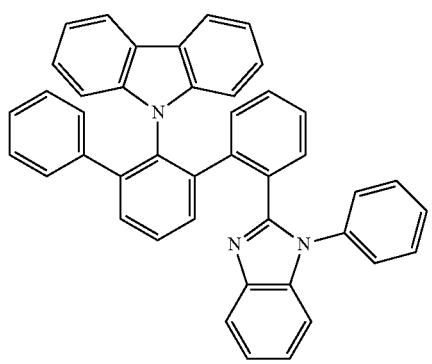
90
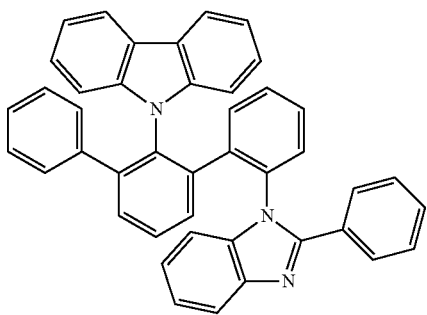
91
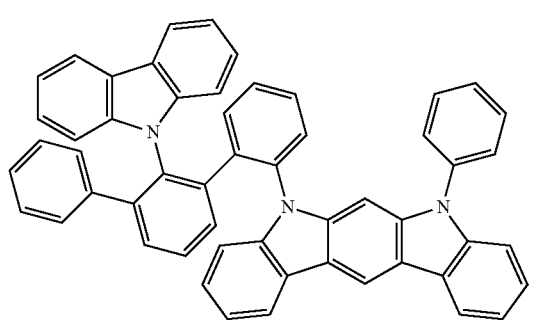
92
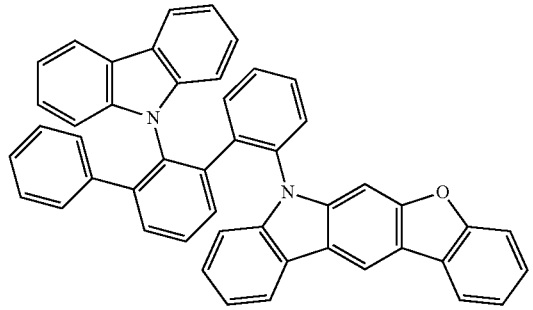
93
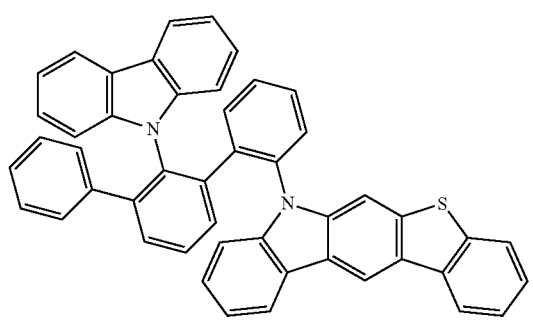

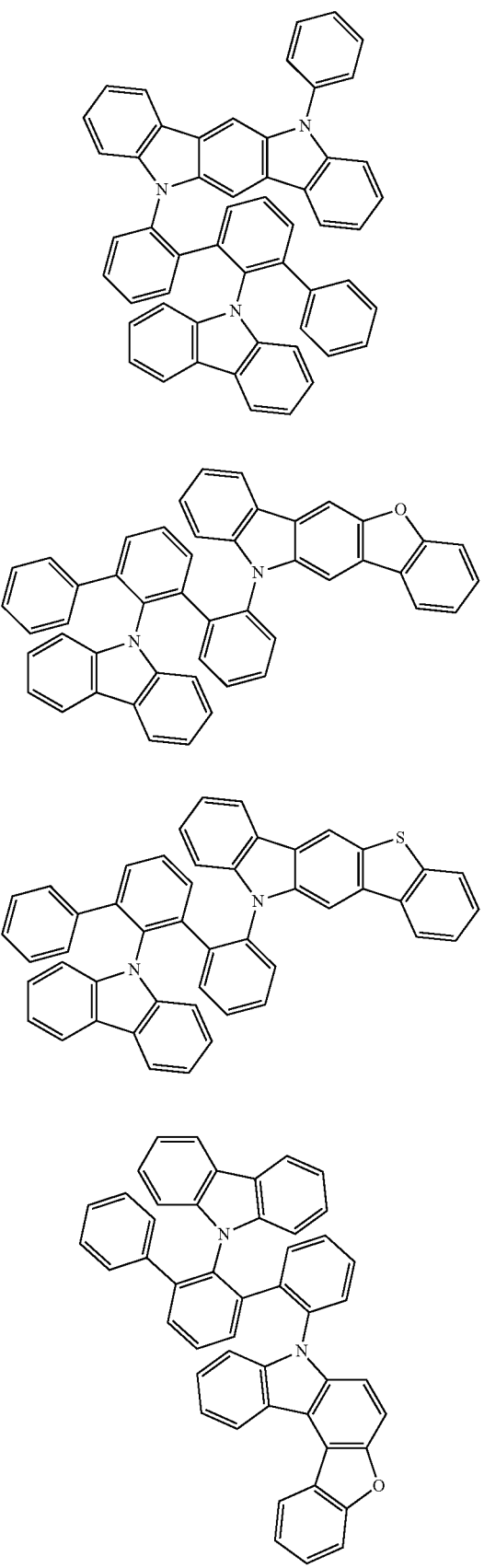
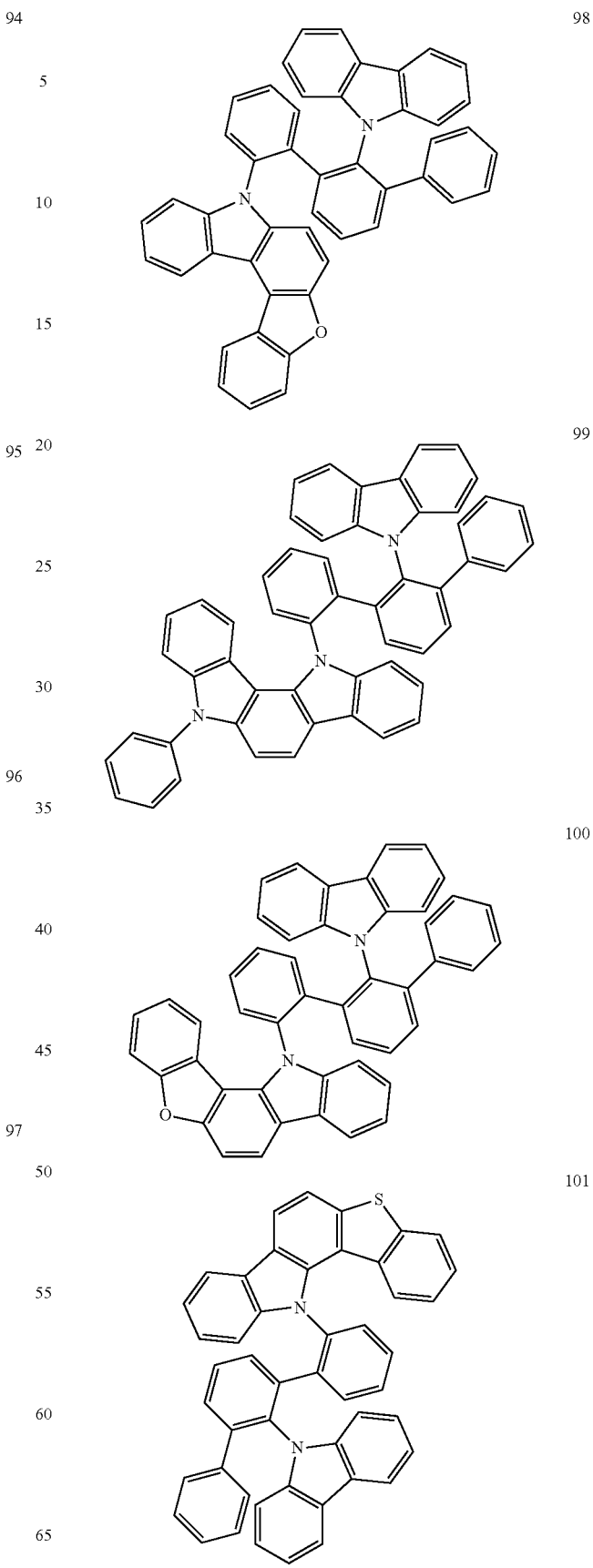

102
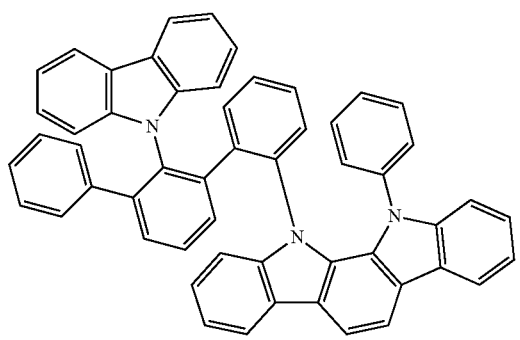
103
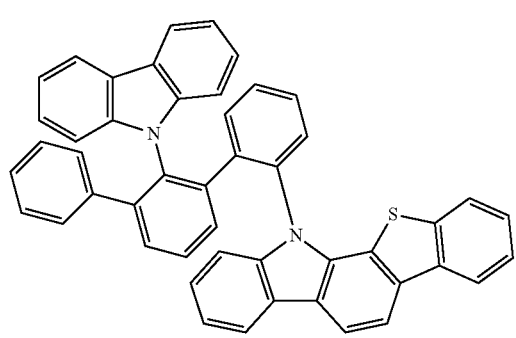
104
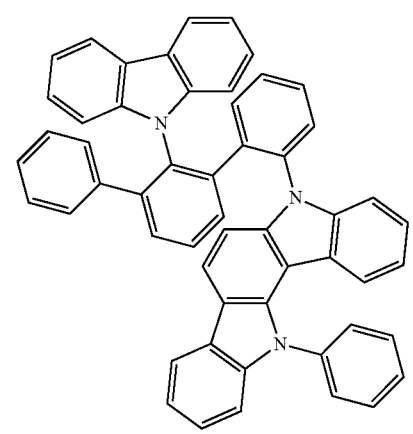
105
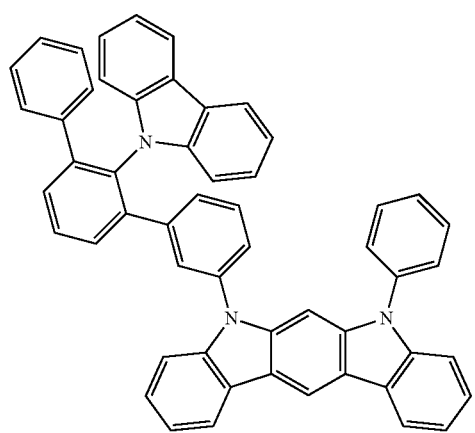
106
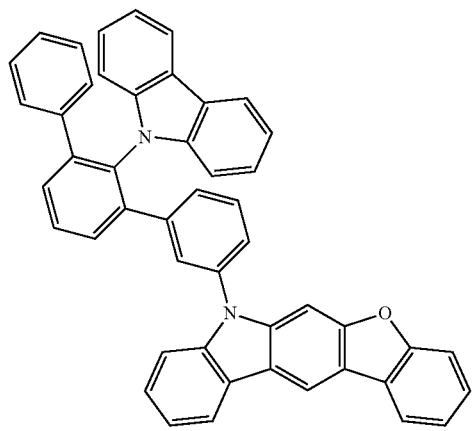
107
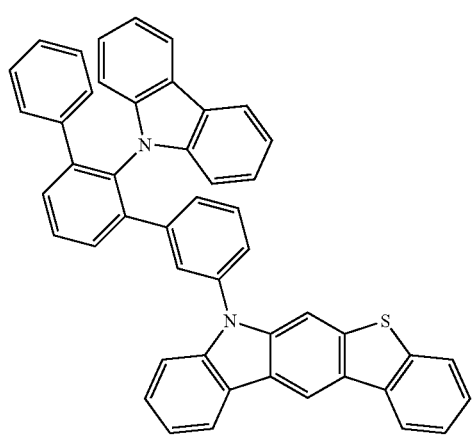
108
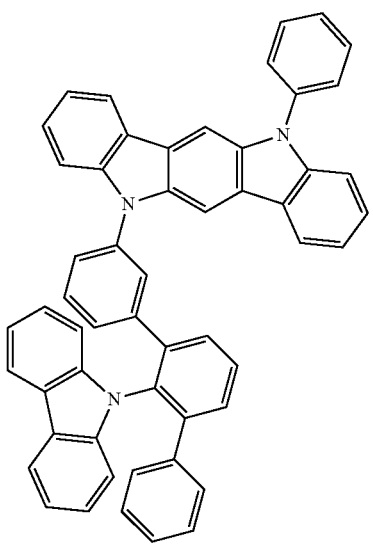

109
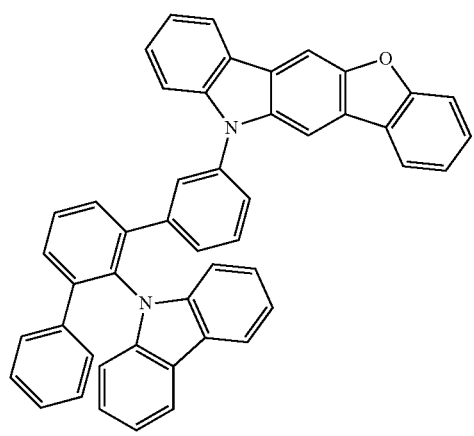
110
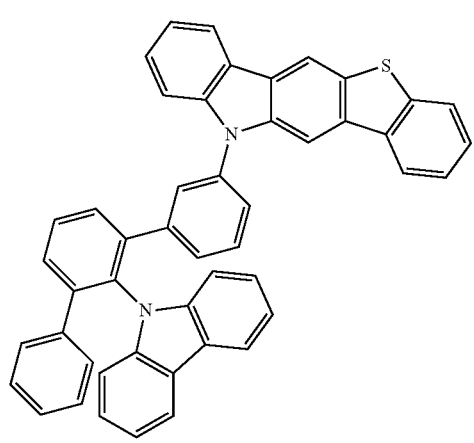
111
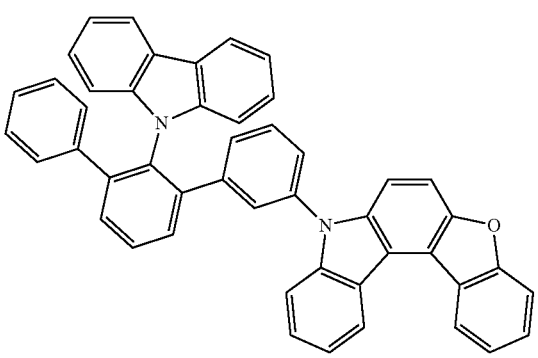
112
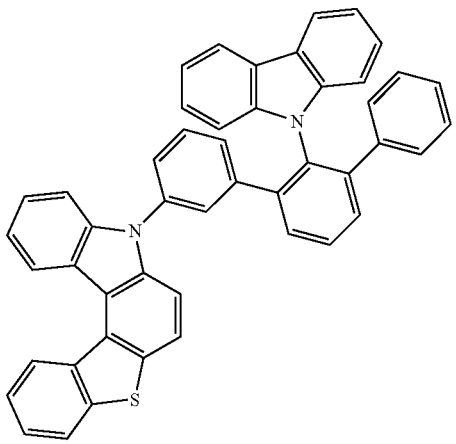
113
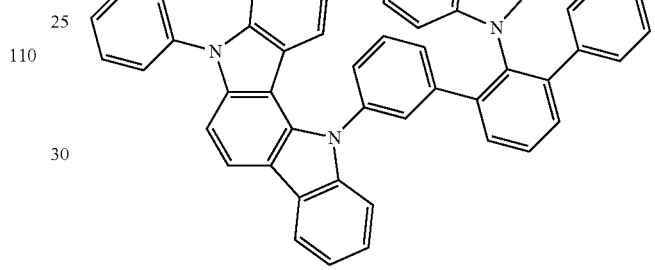
114
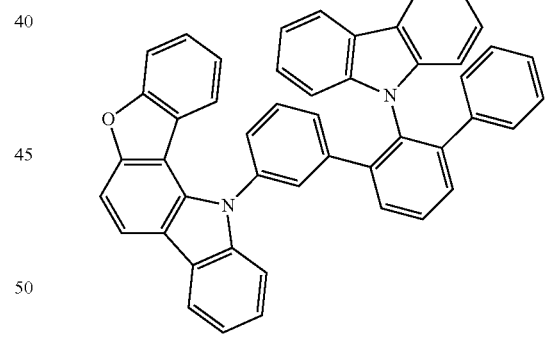
115
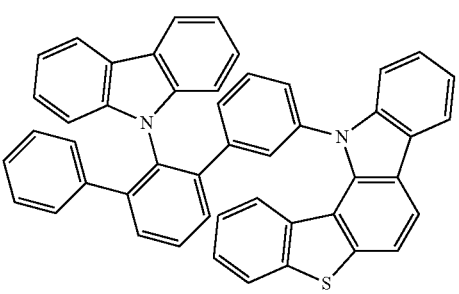

-continued
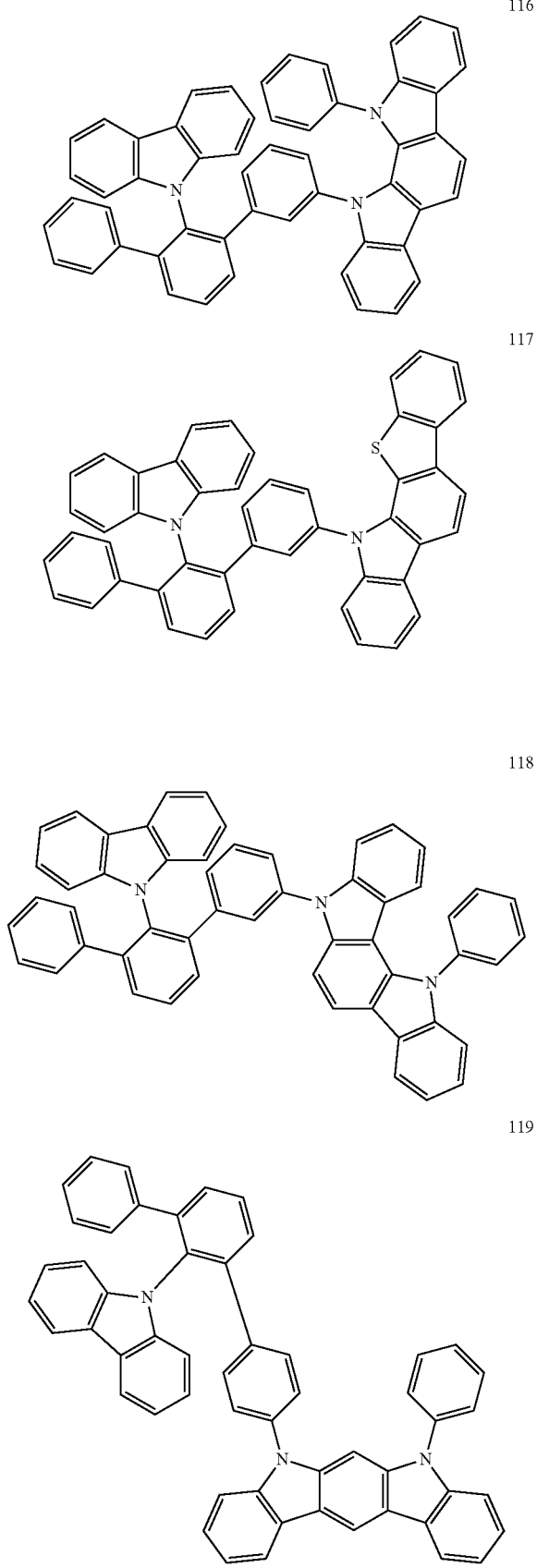
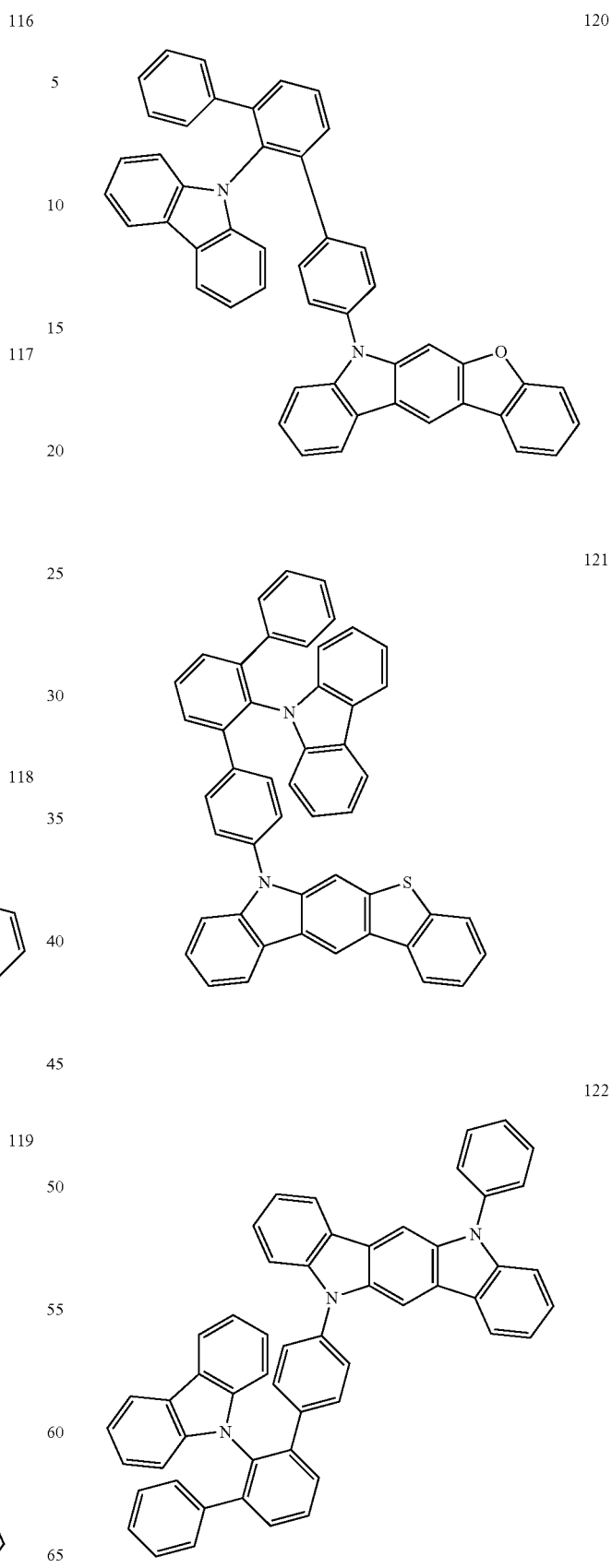

-continued
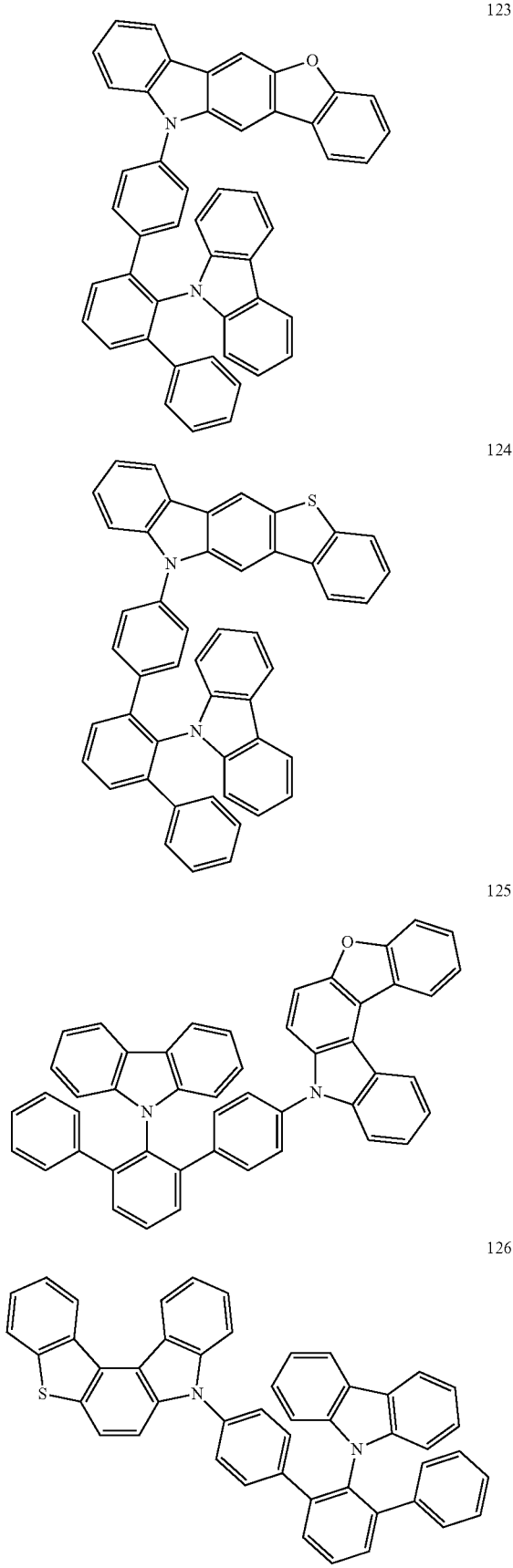
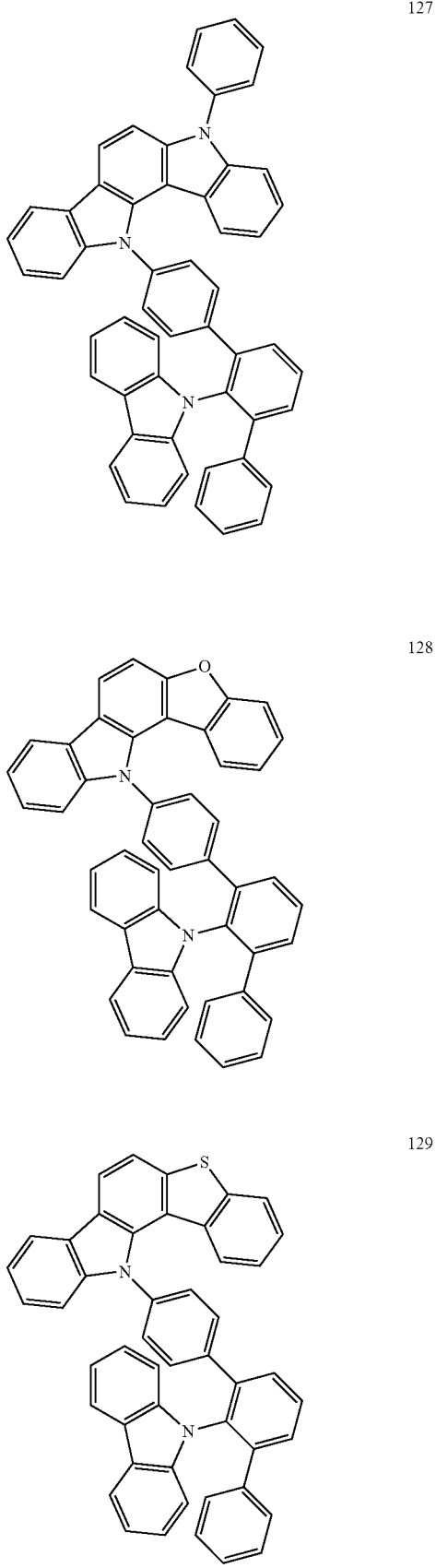

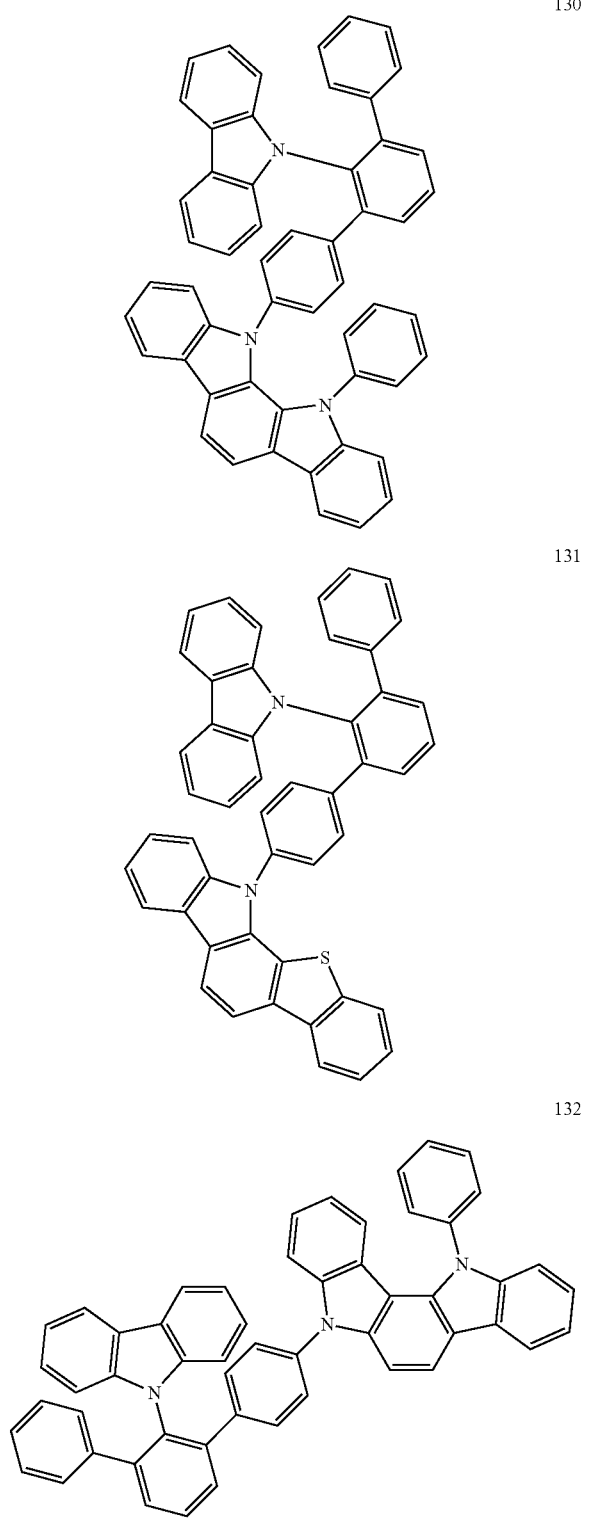
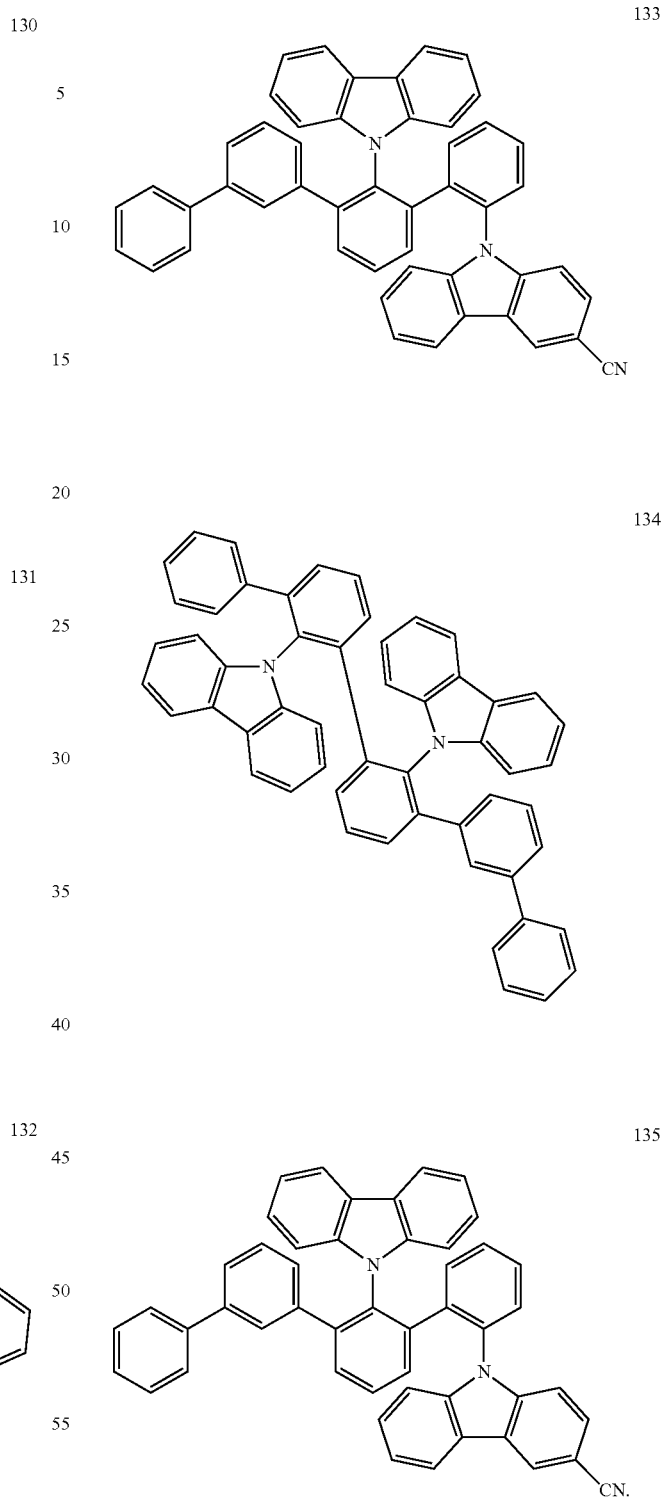
* * * * *